US006593348B2

(12) United States Patent
Carroll et al.

(10) Patent No.: US 6,593,348 B2
(45) Date of Patent: Jul. 15, 2003

(54) OPIATE COMPOUNDS, METHODS OF MAKING AND METHODS OF USE

(75) Inventors: Frank I. Carroll, Durham; James B. Thomas, Efland; S. Wayne Mascarella, Hillsborough, all of NC (US)

(73) Assignee: Research Triangle Institute, Research Triangle Park, NC (US)

(*) Notice: Subject to any disclaimer, the term of this patent is extended or adjusted under 35 U.S.C. 154(b) by 0 days.

(21) Appl. No.: 10/100,096

(22) Filed: Mar. 19, 2002

(65) Prior Publication Data

US 2002/0169324 A1 Nov. 14, 2002

Related U.S. Application Data

(62) Division of application No. 09/623,872, filed as application No. PCT/US99/05131 on Mar. 9, 1999.
(60) Provisional application No. 60/107,902, filed on Nov. 10, 1998, and provisional application No. 60/077,402, filed on Mar. 10, 1998.

(51) Int. Cl.[7] ..................... A61K 31/451; C07D 211/06
(52) U.S. Cl. ..................... 514/331; 546/234; 546/233; 546/229
(58) Field of Search .................. 514/331; 546/234, 546/233, 229

(56) References Cited

U.S. PATENT DOCUMENTS

| 2,683,714 A | 7/1954 | Kallischnigg |
| 2,683,715 A | 7/1954 | Kallischnigg |
| 3,531,487 A | 9/1970 | Berger et al. |
| 3,678,057 A | 7/1972 | Ebnother et al. |
| 3,821,231 A | 6/1974 | Lavrinovich et al. |
| 3,978,222 A | 8/1976 | Enders et al. |
| 4,022,792 A | 5/1977 | Albertson et al. |
| 4,278,797 A | 7/1981 | Zimmerman |
| 4,289,882 A | 9/1981 | Rapoport et al. |
| 4,372,975 A | 2/1983 | Mouzin et al. |
| 4,419,517 A | 12/1983 | Brittelli et al. |
| 4,678,791 A | 7/1987 | Napier et al. |
| 4,816,586 A | 3/1989 | Portoghese |
| RE33,495 E | 12/1990 | Kudzma et al. |
| 5,039,681 A | 8/1991 | Sugimoto et al. |
| 5,091,393 A | 2/1992 | Den Hartog et al. |
| 5,128,118 A | 7/1992 | Carroll et al. |
| 5,141,959 A | 8/1992 | Carroll et al. |
| 5,159,081 A | 10/1992 | Cantrell et al. |
| 5,162,335 A | 11/1992 | Vandewalle et al. |
| 5,214,148 A | 5/1993 | Feldman et al. |
| 5,250,542 A | 10/1993 | Cantrell et al. |
| 5,270,328 A | 12/1993 | Cantrell et al. |
| 5,298,499 A | 3/1994 | Carroll et al. |
| 5,319,084 A | 6/1994 | Cook et al. |
| 5,319,087 A | 6/1994 | Zimmerman et al. |
| 5,380,848 A | 1/1995 | Kuhar et al. |
| 5,413,779 A | 5/1995 | Kuhar et al. |
| 5,457,208 A | 10/1995 | Portoghese et al. |
| 5,496,953 A | 3/1996 | Kuhar et al. |
| 5,637,701 A | 6/1997 | Ashwell |
| 5,736,123 A | 4/1998 | Carroll |
| 5,831,095 A | 11/1998 | Gonzalez et al. |
| 5,854,249 A | 12/1998 | Chang et al. |
| 5,935,953 A | 8/1999 | Kuhar et al. |
| 6,046,200 A | 4/2000 | Tortella et al. |
| 6,123,917 A | 9/2000 | Carroll |

FOREIGN PATENT DOCUMENTS

| EP | 0 018 077 | 10/1980 |
| JP | 4-275288 | 9/1992 |
| WO | WO 93/15062 | 8/1993 |
| WO | WO 98/28269 | 7/1998 |
| WO | WO 98/28270 | 7/1998 |
| WO | WO 99/33806 | 7/1999 |
| WO | WO 99/45925 | 9/1999 |

OTHER PUBLICATIONS

Thomas, J.B. et al.: Identification of an opioid κ receptor subtype–selective N–substituent for (+)–(3R,4R)–dimethyl–4–(3–hydroxyphenyl)piperidine. J. Med. Chem. vol. 41, pp. 5188–5197, 1998.*

Thomas, J.B.; Mascarella, S.W.; Rothman, R.B.; Partilla, J.S.; Xu, H.; McCullough, K.B.; Dersch, C.M.; Cantrell, B.E.; Zimmerman, D.M.; Carroll, F.I. *Investigation of the N–Substituent Conformation Governing Potency and M Receptor Subtype–Selectivity In (+)–(3R,4R)–Dimethyl–4–(3–Hydroxyphenyl)Piperidine Opioid Antagonists*, J. Med. Chem. 1998, 41(11), 1980–1990.

Thomas, J.B.; Zheng, X.; Brieaddy, L.E.; Burgess, J.P.; Mascarella, S.W.; Fix, S.E.; Cantrell, B.E.; Zimmerman, D.M.; Carroll, F.I., *Synthesis of 9B–Methyl–2–Alkyl–7–Oxo–5–Arylmorphans*, Tetrahedron Letters, V. 39, 7001–7004 (1998).

Thomas, J.B.; Zheng, X.; Mascarella, S.W.; Rothman, R.B.; Dersch, C.M.; Partilla, J.S.; Flippen–Anderson, J.L.; George, C.F.; Cantrell, B.E.; Zimmerman, D.M.; Carroll, F.I., *N–Substituted 9B–Methyl–5–3(Hydroxyphenyl)Morphans Are Opioid Receptor Pure Antagonists*, J. Med. Chem. 1998, 41(21), 4143–4149.

Thomas, J.B.; Mascarella, S.W.; Burgess, J.P.; Xu, H.; McCullough, K.B.; Rothman, R.B.; Flippen–Anderson, J.L.; George, C.F.; Cantrell, B.E.; Zimmerman, D.M.; Carroll, F.I., *N–Substituted Octahydro–4A–(3–Hydroxyphenyl)–10A–Methylbenzo[G]isoquinolines are Opioid Receptor Pure Antagonists*, Bioorganic & Medicinal Chemistry Letters 8 (1998) 3149–3152.

Thomas, J.B.; Gigstad, K.M.; Fix, S.E.; Burgess, J.P.; Cooper, J.B.; Mascarella, S.W.; Cantrell, B.E.; Zimmerman, D.M.; Carroll, F.I., *A Stereoselective Synthetic Approach to N–Alkyl–4–B–Methyl–5–Phenylmorphans*, Tetrahedron Letters, V. 40, 403–406 (1999).

(List continued on next page.)

*Primary Examiner*—C. S. Aulakh
(74) *Attorney, Agent, or Firm*—Oblon, Spivak, McClelland, Maier & Neustadt, P.C.

(57) ABSTRACT

The present application relates to novel opioid receptor antagonists and agonists, methods of making these compounds, and methods of use thereof.

6 Claims, 19 Drawing Sheets

OTHER PUBLICATIONS

Thomas, J.B.; Fall, M.J.; Cooper, J.B.; Rothman, R.B.; Mascarella, S.W.; Xu, Heng; Partilla, J.S.; Dersch, C.M.; McCullough, K.B.; Cantrell, B.E.; Zimmerman, D.M.; Carroll, F.I.; *Identification of an Opioid Receptor Subtype–Selective N–Substituent for (+)–(3R,4R)–Dimethyl–4–(3–Hydroxyphenyl)Piperidine, J. Med. Chem.* 1998, 41(26), 5188–5197.

Thomas, J.B.; Atkinson, R.N.; Herault, X.M.; Rothman, R.B.; Mascarella, S.W.; Dersche, C.M.; Xu, H.; Burgess, J.P.; Carroll F.I., *(+)–4–[(N–Allyl–Cis–3–Methyl–4–Piperidinyl)Phenylamino]–N,N–Diethylbenzamide Displays Selective Binding for the Delta Opioid Receptor, Bioorganic & Medicinal Chemistry Letters,* 1999, 9, 3053–3056.

Thomas, J.B.; Atkinson, R. N.; Herault, X. M.; Rothman, R. B.; Mascarella, S. W.; Dersch, C. M.; Xu, H.; Horel, R. B.; Caroll, F. I., *Optically Pure (-)–4–[(N–Allyl–3–Methyl–4–Piperidinyl)Phenyl–Amino]–N,N–Diethylbenzamide Displays Selective Binding and Full Agonist Activity for the δ Opioid Receptor, Bioorg. Med. Chem. Lett.* 1999, 9, 3347–3350.

Thomas, J.B.; Atkinson, R.N.; Rothman, R.B.; Burgess, J.P.; Mascarella, S.W.; Dersch, C.M.; Xu, H.; Carroll, F.I.; *4–8–[Alkyl–8–Azabicyclo[3.2.1]Octyl–3–yl)–3–Arylanilino]–N, N–Diethylbenzamides; High Affinity Selective Ligands for the Delta Opioid Receptor Illustrate Factors Important to Antagonist Activity, Bioorganic & Medicincal Chemistry Letters* 10 (2000) 1281–1284.

Partilla, J.S.; Carroll, F. I.; Thomas, J.B.; Rice, K.C.; Zimmerman, D.M.; Rothman, R.B.; *Opioid Peptide Receptor Studies. 13. Characterization of Opioid Antagonists with the [$^{35}$S]GTPγ–S Binding Assay, Analgesia,* vol. 4, pp. 27–32, 1999.

Chang, K. J.; Rigdon, G. C.; Howard, J. L.; McNutt, R. W. *A Novel, Potent and Selective Nonpeptidic Delta Opioid Receptor Agonist BW373U86, J. Pharm. Exp. Ther.* 1993, 267, 852–857.

Calderon, S. N.; Rothman, R. B.; Porreca, F.; Flippen–Anderson, J. L.; McNutt, R. W.; Xu, H.; Smith, L. E.; Bilsky, E. J.; Davis, P.; Rice, K. C., *Probes for Narcotic Receptor Mediated Phenomena. 19.[1] Sysnthesis of (+)–4–[(AR)–A–((2S, 5R)–4–Allyl–2,5–Dimethyl–1–Piperazinyl)–3–Methoxybenzyl]–N,N–Diethylbenzamide (SNC 80): A Highly Selective, Nonpeptide δ Opioid Receptor Agonist, J. Med. Chem.* 1994, 37, 2125–2128.

Dondio, G.; Ronzoni, S.; Petrillo, P., *Non–Peptide δ Opioid Agonists and Antagonists (Part II), Exp. Opin. Ther. Patents* 1999, 9, 353.

Zhang, X.; Rice, K. C.; Calderson, S., N.; Kayakiri, H.; Smith, L., Coop, Andrew; Jacobson, A. E.; Rothman, R. B.; Davis, P.; Dersch, C. M.; Porreca, F., *Probes for Narcotic Receptor Mediated Phenomena. 26.[1-3] Synthesis and Biological Evaluation of Diarylmethylpiperazines and Diarylmethylpiperidines as Novel, Nonpetidic δ Opioid Receptor Ligands, J. Med. Chem.* 1999, 42, 5455–5463.

Dondio, G.; Ronzoni, S.; Eggleston, D. S.; Artico, M.; Petrillo, P.; Petrone, G.; Visentin, L.; Farina, C.; Vecchietti, V.; Clarke, G. D., *Discovery of a Novel Class of Substituted Pyrrolooctahydroisoquinolines as Potent and Selective δ Opioid Agonists, Based on an Extension of the Message–Address Concept, J. Med. Chem.* 1997, 40, 3192–3198.

Su, Y.–F.; McNutt, R. W.; Chang, K.–J., *Delta–Opioid Ligands Reverse Alfentanil–Induced Respiratory Depression But Not Antiociception[1] J. Pharmacol. Exp. Ther.* 1998, 287, No. 3, 815–823.

Mattson, R. J.; Pham, K. M.; Leuck, D. J.; Cowen, *An Improved Method for Reductive Alkylation of Amines Using Titanium (IV) Isopropoxide and Sodium Cyanoborohydride, J. Org. Chem.* 1990, 55, 2552–2554.

Abdel–Magid, A. F.; Carson, K. G.; Harris, B. D.; Maryanoff, C. A.; Shah, R. D., *Reductive Amination of Aldehydes and Ketones with Sodium Triacetoxyborohydride. Studies on Direct and Indirect Reductive Amination Procedures, J. Org. Chem.* 1996, 61, 3849–3862.

Hattori, T.; Satoh, T.; Miyano,, *Convenient Synthesis of Triarylamines Via Ester–Mediated Nucleophilic Aromatic Substitution,* S. *Synthesis* 1996, 514–518.

Aldrich, J. V., *Analgesics, Burger's Medicinal Chemistry and Drug Discovery;* M. E. Wolff, Ed.; John Wiley & Sons: New York, 1996; vol. 3. 321–441.

Dhawan, B.N.; Cesselin, F.; Raghubir, R.; Reisine, T.; Bradley, P.B.; Portoghese, P.S.; Hamon, *International Union of Pharmacology. XII. Classification of Opioid Receptors, Pharmacol. Rev.* 1996, 48, 567–592.

Martin, W.R., *The Evolution of Concepts of Opioid Receptors, The Opiate Receptors,* Pasternak, G.W. Eds.; Human Press Inc.; New Jersey, 1988, pp. 3–22.

Portoghese, P.S.; Nagase, H.; Lipkowski, A.W.; Larson, D.L.; Takemori, A.E., *Binaltorphimine–Related Bivalent Ligands and Their κ Opioid Receptor Antagonist Selectivity,* [published erratum appears in *J. Med. Chem.* Oct. 31, 1998 (1): 2056]. *J. Med. Chem.* 1988, 31, 836–841.

Portoghese, P.S., *An Approach to the Design of Receptor–Type–Selective Non–Peptide Antagonists of Peptidergic Receptors: δ Opioid Antagonists, J. Med. Chem.* 1991, vol. 34, No. 6, 1757–1762.

Zimmerman, D.M.; Nickander, R.; Horng, J.S.; Wong, D.T., *New Structural Concepts for Narcotic Antagonists Defined In A 4–Phenylpiperidine Series, Nature,* 1978, 275, 332–334.

Zimmerman, D.M.; Leander, J.D.; *Perspective, Selective Opioid Receptor Agonists and Antagonists: Research Tools and Potential Therapeutic Agents, J. Med. Chem.,* 1990, 33, 895–902.

Rothman, R.B.; Gorelick, D.A.; Eichmiller, P.R.; Hill, B.H.; Norbeck, J.; Liberto, J.G., *An Open–Label Study of a Functional Opioid k Antagonist in the Treatment of Opioid Dependence, Problems of Drug Dependence, 1997: Proceedings of the 59th Annual Scientific Meeting, The College on Problems of Drug Dependence, Inc.,* Harris, L.S. Eds.; U. S. Department of Health and Human Services: Rockville, MD, 1997; vol. 178, pp. 309.,.

Mitch, C.H.; Leander, J.D.; Mendelsohn, L.G.; Shaw, W.N.; Wong, D.T.; Cantrell, B.E.; Johnson, B.G.; Reel, J.K.; Snoody, J.D.; Takemori, A.E.; Zimmerman, D.M., *3,4–Dimethyl–4–(3–Hydroxyphenyl)Piperidines: Opioid Antagonists with Potent Anorectant Activity, J. Med. Chem.,* 1993, 36 (20), 2842–2850.

Zimmerman, D.M.; Smits, S.E.; Hynes, M.D.; Cantrell, B.E.; Leaner, J.D.; Mendelsohn, L.G.; Nickander, R.; *Picenadol, Drug and Alcohol Dependence,* 1985, 14, 381–402.

Zimmerman, D.M.; Gidda, J.S.; Cantrell, B.E.; Schoepp, D.D.; Johnson, B.G.; Leander, J.D., *Discovery of a Potent, Peripherally Selective Trans–3,4–Dimethyl–4–(3–Hydroxyphenyl)Piperidine Opioid Antagonist for the Treatment of Gastrointestinal Motility Disorders*, J. Med. Chem, 1994, 37(15), 2262–2265.

Evans, D.A.; Mitch, C.H.; Thomas, R.C.; Zimmerman, D.M.; Robey, R.L., *Application of Metalated Enamines to Alkaloid Synthesis. An Expedient Approach to the Synthesis of Morphine–Based Analgesics*, J. Am. Chem. Soc., 1980, 102, 5955–5956.

Awaya, H.; May, E.L.; Aceto, M.D.; Merz, H.; Rogers, M.E.; Harris, L.S., *Racemic and Optically Active 2,9–Dimethyl–5–(m–Hydroxyphenyl)Morphans and Pharmacological Comparison with the 9–Dimethyl–Homologues*, J. Med. Chem., 1984, 27, 536–539.

Van Bever, W.F.; Niemegeers, C.J.E.; Janssen, P.A.J.; *Synthetic Analgesics. Synthesis and Pharmacology of the Diastereoisomers of N–(3–Methyl–1–(2–Phenylethyl)–4–Piperidyl)–N–Phenylpropanamide and N–(3–Methyl–1–Methyl–1–(1–Methyl–2–Phenylethyl)–N–Phenylpropanamide*, J. Med. Chem., 1974, 17(10), 1047–1051.

Xu, H.; Kim, C.–H.; Zhu, Y.C.; Weber, R.J.; Jacobson, A.E., Rice, K.C.; Rothman, R.B., (+)–*Cis–Methylfentanyl and Its Analogs Bind Pseudoirreversibly to the Mu Opioid Binding Site; Evidence for Pseudoallosteric Modulation*, Neuropharmacology 1991, 30, 455–462.

Xu, H.; Lu, Y.–F; Partilla, J.S.; Brine, G.A.; Carroll, F.I.; Rice, K.C.; Lai, J.; Porreca, F.; Rothman, R.B., *Opioid Peptide Receptor Studies. 6. The 3–Methylfentanyl Congeners RTI–4614–4 and Its Enantiomers Differ in Efficacy, Potency, and Intrinsic Efficacy as Measured by Stimulation of [$^{35}$S]GTP–γ–S Binding Using Clonded M–Opioid receptors*, Anagelsia, 1997, vol. 3, 35–42.

Rothman, R.B.; Xu, H.; Seggel, M.; Jacobson, A.E.; Rice, K.C.; Brine, G.A.; Carroll, F.I.; *RTI–4614–4: An Analog of (+)–Cis–3–Methylfentanyl with A 27,000–Fold Binding Selectivity for Mu Versus Delta Opioid Binding Sites*, Life Sci., 1991, vol. 48, PL111–PL–116.

Rothman, R.B.; Bykov, V.; de Costa, B.R.; Jacobson, A.E.; Rice, K.C.; Brady, L.S., *Interaction of Endogenous Opioid Peptides and Other Drugs with Four Kappa Opioid Binding Sites in Guinea Pig Brain*, Peptides, 1990, vol. 11, 311–331.

Rodbard, D.; Lenox, R.H.; Wray, H.L.; Ramseth, D., *Statistical Characterization of the Random Errors in the Radioimmunoassay Dose–Response Variable*, Clin. Chem., 1976, vol. 22, 350–58.

Takemori, A.E.; Begonia, Y.H.; Naeseth, J.S.; Portoghese, P.S., *Nor–Binal Torphimine, A Highly Selective Kappa–Opioid Antagonist in Analgesic and Receptor Binding Assays*, J. Pharm. Exp. Ther., 246 (1), 255–258.

Zimmerman, D.M.; Leander, J.D.; Cantrell, B.E.; Reel, J.K.; Snoddy, J.; Mendelsohn, L.G.; Johnson, B.G.; Mitch, C.H.; *Structure–Activity Relationships of the Trans–3, 4–Dimethyl–4–(3–Hydroxyphenyl)Piperidine Antagonists for µ and κ Opioid Receptors*, J. Med. Chem., 1993, 36(2), 2833–2841.

Casy, A.F.; Dewar, G.H.; Al–Deeb, O.A.A., *Stereochemical Influences Upon the Opioid Ligand Activites of 4–Alkyl–4–Arypiperidine Derivatives*, Chirality 1989, 1: 202–208.

Casy, A.F.; Dewart, G.H.; Al–Deeb, O.A.A., *Stererochemical Studies of the 4–Alkyl–4–Arylpiperidine Class of Opioid Ligand*, Magn. Reson. Chem., 1989, 27, 964–972.

Zimmerman, D.M.; Cantrell, B.E.; Reel, J.K.; Hemrick––Luecke, S.K.; Fuller, R.W., *Characterization of the Neurotoxic Potential of M–Methoxy–MPTP and the use of its N–Ethyl Analogue as a Means of Avoiding Exposure to a Possible Parkinsonism–Causing Agent*, J. Med. Chem., 1986; 29:1517–1520.

Fries, D.S.; de Vries, J.; Hazelhoff, B.; Horn, A.S.; *Synthesis and Toxicity Toward Nigrostriatal Dopamine Neurons of 1–Methyl–4–Phenyl–1,2,3,6–Tertrahydropyridine (MPTP) Analogues*, J. Med. Chem., 1986, 29:424.

Barnett, C.J.; Copley–Merriman, C.R.; Maki, J., *Synthesis of Picenadol via Metalloenamine Alkylation Methodology*, J. Chem., 1989; 54:4795–4800.

Werner, J.A.; Cerbone, L.R.; Frank, S.A.; Ward, J.A.; Labib, P.; Tharp–Taylor, R.W.; Ryan, C.W., *Synthesis of Trans 3,4–Dimethyl–4–(3–Hydroxyphenyl)Piperidine Opioid Antagonists: Application of the Cis– Thermal Elimination of Carbonates to Alkaloid Synthesis*, J. Org. Chem., 1996, 61: 587–597.

Gu, X–P.; Nishida, N.; Ikeda, I.; Okahara, M.; *2–(Chloromethyl)–3,5–Dioxahex–1–Ene, An Effective Acetonylating Reagent*, J. Org. Chem., 1987, 52: 3192–3196.

Bosch, J.; Bonjoch, J., *Synthesis of 2–Azabicyclo[3.3.1] Nonanes*, Heterocycles, 1980, 14, 505.

Rice, K.C., *A Rapid, High–Yield Conversion of Codeine to Morphine*, J. Med. Chem., 1977, 20, 164–165.

Bertha, C.M.; Flippen–Anderson, J.L.; Rothman, R.B.; Porreca, F.; Davis, P.; Xu, H.; Becketts, K.; Cha, X.–Y.; Rice, K.C., *Probes for Narcotic Receptor–Mediated Phenomena. 20. Alteration of Opioid Receptor Subtype Selectivity fo the 5–(3–Hydroxyphenyl)Morphans by Application of the Message—Address Concept: Preparation of Δ–Opioid Receptor Ligands*, J. Med. Chem., 1995, 38, 1523–1537.

Bertha, C.M.; Ellis, M.; Flippen–Anderson, J.L.; Porreca, F.; Rothman, R.B.; Davis, P.; Xu, H.; Becketts, K.; Rice, K.C., *Probes for Narcotic Receptor–Mediated Phenomena. 21. Novel Derivatives of 3–(1,2,3,4,5,11–Hexahydro–3–Methyl–2,6–Methano–6H–Azocino[4, 5–b–Indol–6–yl)–Phenols with Improved δ Opioid Receptor Selectivity*, J. Med. Chem., 1996, 39, 2081–2086.

Kreek, M.J., *Opiates, Opioids and Addiction*, Molecular Psychiatry (1996), 1: 232–254.

Bonjoch, J., *Stereocontrolled Synthesis of 4– and 9–Ethyl–2–Azabicyclo[3.3.1]Nonan–7–Ones via 2–Cyanopiperidines*, Tetrahedron Letters, vol. 30, No. 41, pp. 5655–5658, 1989.

Kirk–Othmer Encyclopedia of Chemical Technology, vol. 17, Fourth Edition, 1996, pp. 858–881.

Zadina, J.E.; Hackler, L.; Ge, L.; Kastin, A.J., *A Potent and Selective Endogenous Agonist for the M–Opiate Receptor*, Nature, 1997, 386, 499–502.

Portoghese, et al., *Additions and Corrections*, J. Med. Chem., 1988, 31(10), 2056.

Michne, W.F.; Lewis, T.R.; Michalec, S.J.; Pierson, A.K.; Gillan, M.G.C.; Paterson, S.J.; Robson, L.E.; Kosterlitz, H.W., *Novel Developments of N–Methylbenzomorphan Narcotic Antagonists*, Elsevier Amsterdam, 1978, pp. 197–206.

Wood, P.L.; Piplapil, C.; Thakur, M.; Richard, J.W., *Win 44.441: A Stereospecific and Long–Acting Narcotic Antagonist*, Pharmaceutical Research, 1984, 46–48.

Zimmerman, D.M.; Smiths, S.; Nickander, R., *Further Investigation of Novel 3–Methyl–4–Phenylpiperidine Narcotic Angagonists*, in Proceedings of the 40<sup>th</sup> Annual Scientific Meeting of the Committee on Problems of Drug Dependence, 1978, pp. 237–247.

Fries, D.S.; Portoghese, P.S., *Stereochemical Studies on Medicinal Agents. 20. Absolute Configuration and Analgetic Potency of A–Promedol Enantiomers, The Role of the C–4 Chiral Center in Conferring Stereoselectivity in Axial– and Equatorial–Phenyl Prodine Congeners, J. Med. Chem.*, 1976, 19(9), 1155–1158.

Kamei, J.; Saitoh, A,; Ohsawa, M.; Suzuki, T.; Misawa, M.; Nagase, H.; Kasuya, Y. *Antinociceptive Effect of the Non–Peptidic Δ–Opioid Receptor Agonist Tan–67 In Diabetic Mice, European Journal of Pharmacology*, 1995, 276, 131–135.

Froimowitz et al., *Absolute Configuration and Conformation of the Pure Opioid Antagonist (+)–2, 9α–Dimethyl–5–)m–Hydroxyphenyl)Morphan, Chirality*, vol. 4, 1992, 377–383.

Di Meglio et al., *Conformational Analysis of the Opioid Phenylmorphan and its use 9α–Methyl Analogue in Solution Using High–Resolution Nuclear Magnetic Resonance Spectroscopy, Pharmaceutical Research*, 1993, vol. 10, No. 8, 1200–1205.

Froimowitz et al., *Phenylmorphans and Analogues: Opioid Receptor Subtype Selectivity and Effect of Conformation of Activity, J. Med. Chem.*, 1992, 35, 1521–1525.

Thomas et al., *Factors Influencing Agonist Potency and Selectivity for the Opioid Δ Receptor are Revealed in Structure–Activity Relationship Studies of the 4–[(N–Substituted–4–Piperidinyl)Arylamino]–N,N–Diethylbenzamides, J. Med. Chem.*, 44(6), 2001, pp. 972–987.

Robert E. Boyd, et al., *Synthesis and Binding Affinities of 4–Diarylaminotropanes, A New Class of Delta Opioid Agonists, Bioorganic & Medicinal Chemistry Letters*, 10(2000) 1109–1111.

Froimowitz et al., "Phenylmorphans and Analogues: Opioid Receptor Subtype Selectivity and Effect of Conformation on Activity", Journal of Medicinal Chemistry, vol. 35, No. 9, 1992, pp. 1521–1525.

Bertha et al., "Probes for arcotic Receptor–Mediated Phenomena. 20. Alteration of Opioid Receptor Subtype Selectivity of the t–(3–Hydroxyphenyl)morphans by Application of the Message–Address Concept: Preparation of .delta.–Opioid Receptor Ligands", Journal of Medicinal Chemistry, vol. 38, No. 9, 1995, pp. 1523–1537.

Bertha et al., "A Marked Change of Receptor Affinity of the 2–Methyl–5–(e–hydroxyphenyl)morphans upon Attachment of an (E)–8–Benzylidene Moiety: Synthesis and Evaulation of a New Class of .sigma. Receptor Ligands", Journal of Medicinal Chemistry, vol. 37, No. 19, 1994, pp. 3163–3170.

Ong, et al., "Phenylmorphan Agonists–Antagonists" Journal of Medicinal Chemistry, vol. 17, No. 1, 1974, pp. 133–134.

Thomas et al., "A Stereoselective Syynthetic Approach to N–Alkyl–4beta–methyl–5–phenyl morphans" Tetrahedron Letters, Elsevier Science Publishers, Amsterdam, NL, vol. 40, No. 3, Jan. 15, 1999 (Jan. 15, 1999), pp. 403–406.

Thomas et al., "N–substituted 9.beta.–Methyl–5–(3–hydroxyphenyl)morphans Are Opioid Receptor Pure Antagonists", Journal of Medicinal Chemistry, vo. 41, No. 21, 1998, pp. 4143–4149.

Calderon et al., "Probes for narcotic receptor Mediated Phenomena. 19, Synthesis of (1)–4[[(.alpha.R)–.alpha.((2S, 5R)–4–Allyl–2,5–dimethyl–1–piperazinyl)–3–methoxybenzyl]–N,N–diethylbenzamide (SNC 80): A Highly Selective Nonpeptide .delta. Opioid Receptor Agonist", Journal of Medicinal Chemistry, vol. 37, No. 14, 1994, pp. 2125–2128.

Thomas et al., "Optically Pure (0)–4–[(N–Allyl–3–Methyl–4–Piperidinyl)Phenylamino]–N,N–Diethylbenzamide Displays for the delta Opioid Receptor", Bioorganic & Medicinal Chemistry Letters, Oxford, GB, vol. 9, No. 23, Dec. 6, 1999 (199–12–06), pp. 3347–3350.

* cited by examiner

R₁ = ALKyl

R₁ = ArALKyl

Reagents: (a) s-BuLi, THF; AND (b) NaI, CH₃CN;

(c) NaBH₄, EtOH;

(d) HBr, HOAc;

(e) PhOCOCl, toluene;

(f) aryl-alkyl-COOH, BOP, triethylamine, THF;

(g) borane/THF

Reagents: (a) s-BuLi, allyl-Br;

(b) H$_3$PO$_4$, HCO$_2$H;

(c) NaHB(OAc)$_3$;

(d) HOAc, HBr;

(e) PhOCOCl, then KOH, H$_2$O;

(f) BOP, aryl-alkyl-COOH;

(g) borane/THF

Reagents: (A) Ti(O-i-Pr)$_4$, :NH—◯—(Z)$_y$ (b) NaBH$_4$, EtOH;

(c) n-BuLi, THF, HMPA then 1-(2,6-di-tert-butyl-4-methoxy)-4-fluorobenzoate;

(d) N-methylpyrrolidinone, NaOCH$_3$, toluene;   (e) EtOH, H$_2$O;

(f) R$_a$R$_b$NH, BOP, Et$_3$N;   (g) PhOCOCl;

(h) KOH, i-PrOH, H$_2$O;   (i) R$_5$-Br, EtOH, K$_2$CO$_3$

|     | R₁    | R₂   |
|-----|-------|------|
| 6a, | H     | H    |
| b,  | H     | CH₃  |
| c,  | CH₃   | H    |
| d,  | CH₃   | CH₃  |
| e,  | i-Pr  | H    |
| f,  | i-Pr  | H    |
| g,  | i-Bu  | H    |
| h,  | s-Bu  | H    |
| i,  | c-Hex | H    |
| j,  | Ph    | CH₃  |
| k,  | Bn    | H    |

7

R₃

X=OH, OMe, OEt, OBn,
OnBu, OPh, Me, iPr, Bu,
Ph, NMe₂, CONH₂, F, Cl, Br.

*Reagents: (a) Boc-amino acid, BOP, TEA, THF;

(b) TFA, CH₂Cl₂;

(c) borane/dimethyl sulfide;

(d) R₃CO₂H, BOP, TEA, THF.

(a) s-BuLi, THF; α,α'-dichloroxylene;
(b) NaI, CH₃CN;
(c) NaBH₄, EtOH;
(d) HBr, HOAc;
(e) PhOCOCl, toluene;
(f) Phenyl Acetic Acid, BOP, TEA, THF;
(g) Borane/THF;

Naltrexone
(phenylaxial/piperidine chair)

3,4-Dimethyl-4-(3-hydroxyphenyl)piperidine
(phenylequatorial/piperidine chair)

8a-Methyl-4a-(3-hydroxyphenyl)octahydrobenzo[e]isoquinoline
(phenylequatorial/piperidine chair)

a (a) s-BuLi, allyl-Br;

(b) H₃PO₄, HCO₂H;

(c) NaHB(OAc)₃;

(d) HOAc, HBr;

(e) PhOCOCl, then KOH, H₂O;

(f) (benzotriazol-1-yloxy)tris(dimethylamino) phosphonium hexafluorophosphate, PhCH₂CO₂H;

(g) borane-dimethyl sulfide, THF.

Naltrexone (1b)

3-hydroxphenyl axial piperidine chair 3,4-Dimethyl-4-(3-hydroxyphenyl)-piperidine (4)

3-hydroxyphenyl equatorial piperidine chair ⇌ 3-hydroxyphenyl axial piperidine chair 2-Alkyl-9β-methyl-5-(3-hydroxphenyl)-morphan (5)

3-hydroxyphenyl equatorial piperidine chair

Reagents: (a) Ti(O-i-Pr)$_4$, aniline; (b) NaBH$_4$, EtOH; (c) n-BuLi, THF, HMPA then 1-(2,6-di-tert-butyl-4-methoxy)-4-fluorobenzonate; (d) N-methylpyrrolidinone, NaOCH$_3$, toluene; (e) EtOH, H$_2$O; (f) Et$_2$NH, BOP, Et$_3$N; (g) PhOCOCl; (h) KOH, i-PrOH, H$_2$O; (i) allyl-Br, EtOH, K$_2$CO$_3$

OPIATE COMPOUNDS, METHODS OF MAKING AND METHODS OF USE

This application is a Divisional of U.S. Ser. No. 09/623,872, filed Nov. 27, 2000, now allowed, which is a National Stage of International Application PCT/US99/05131, filed on Mar. 9, 1999, which claims benefit to U.S. Provisional Application Ser. No. 60/077,402, filed on Mar. 10, 1998 and U.S. Provisional Application Ser. No. 60/107,902, filed on Nov. 10, 1998.

BACKGROUND OF THE INVENTION

1. Field of the Invention

The present invention relates to novel opioid receptor antagonists and agonists, methods of making these compounds, and methods of use.

2. Description of the Background

The opioid receptor system has been extensively studied over the past eight decades, driven primarily by a search for analgesics that do not possess the abuse potential associated with morphine. While these studies were unsuccessful, our understanding of the opioid system has increased tremendously. A significant breakthrough in our understanding of this system came about as a realization that the pharmacology of opioids is receptor based. From this vantage point, the focus of research turned to identifying receptor subtypes with the ultimate goal of assigning specific physiological function to individual receptors. Today, the receptor system is known to be composed of the three distinct subtypes $OP_1$, $OP_2$, and $OP_3$ (delta, kappa and mu), as each of these have been cloned and been shown to derive from three different chromosomes. For a discussion of opioid receptors, see Kirk-Othmer Encyclopedia of Chemical Technology, Volume 17, Fourth Edition, 1996, pp. 858–881. There is however less however as to the number of subtypes within each of the main branches and while much has been learned along these lines, the process of assigning function to subtypes is still an area of active investigation.

The opioid receptor system has been extensively studied over the past eight decades driven primarily by a search for analgesics that do not possess the abuse potential associated with morphine. While this effort has been unsuccessful to date, recent studies have highlighted the delta opioid receptor system as holding the greatest potential for success. Principally, agonists acting through the delta opioid receptor have been shown to modulate pain while minimizing many of the side-effects associated with morphine which acts primarily at the mu opioid receptor. These unwanted side-effects include physical dependence, respiratory depression, and gastrointestinal motility problems. These findings have led to a dramatic increase in the research efforts directed toward the production of potent, highly delta receptor selective agonists. The bulk of this effort has been in discovering small molecules as opposed to peptides due to their enhanced stability in vivo and their ability to penetrate the central nervous system.

I

The discovery of potent, highly receptor-selective opioid pure antagonists has been a goal of medicinal chemists for many years.[1,2] As molecular probes, antagonists have served as useful tools in the study of both the structure as well as the physiological functions of the highly complex opioid receptor system. Much has been accomplished as evidenced by the elegant work of Portoghese and coworkers over the past decade which ultimately has led to the discovery of the naltrexone-based kappa and delta receptor subtype-selective antagonists norbinaltorphimine[3] (1, nor-BNI) and naltrindole[4] (2, NTI), respectively. Following Portoghese's lead, workers at SmithKline Beecham recently reported that the octahydroisoquinoline (3, SB 205588) was a second-generation, highly potent and selective delta antagonist formally derived from naltrindole fragmentation.[5] One specific research aim has been the discovery of opioid receptor selective reversibly binding ligands from the N-substituted (+)-(3R,4R)-dimethyl-4-(3-hydroxyphenyl)piperidine (4a) class of compounds that display pure antagonist activity.[6] These compounds will be useful as molecular probes for the opioid receptor as well as potential drug candidates for the treatment of substance abuse and other CNS disorders.[7] While mu antagonists have for years been used in drug abuse therapy, recent findings suggest that kappa antagonists could provide a more effective, long-lasting treatment strategy.[8] A great variety of N-substituted derivatives of 4a has been prepared, but until the recent demonstration of mu selectivity for 5a,[9] none had shown selectivity between the opioid receptor subtypes. Since the pure antagonist activity of these compounds is not dependent on the N-substituent, multiple changes to this part of the molecule would be expected to affect binding affinity and possibly receptor selectivity but not alter its fundamental antagonist character. This feature distinguishes this class of antagonist from the morphone-based compounds, which display pure antagonist behavior only with N-substituents such as allyl or cyclopropylmethyl but not methyl, ethyl, or phenethyl.[10] It is currently believed that the N-substituent in 4a interacts with a lipophilic binding domain which has been described as either very large or quite malleable since a multitude of different types of N-substituent changes provided ligands displaying high binding affinity.[11] It has also been determined that maximum potency and selectivity for the mu opioid receptor is achieved when the N-substituent incorporates a lipophilic entity (phenyl or cyclohexyl ring) separated from the piperidine nitrogen by three atoms as illustrated by compounds 5a–d.[9,11] The synthesis of κ-selective compounds remains an important goal.

II

Derivatives of N-substituted (±)-trans-3,4-dimethyl-4-(3-hydroxyphenyl)piperidine, such as 6 and 7, are known to posses nonselective potent opioid pure antagonist activity.[12-16] Early investigations of the phenylpiperidine class of opioid antagonists identified the 3-methyl substituent and its trans relative relationship to the 4-substituent as being both necessary and sufficient to impart antagonist activity to the agonist 4-(3-hydroxyphenyl)piperidine.[12] This feature distinguished the phenylpiperidines from the oxymorphones which rely on particular N-substituents (i.e. allyl, cyclopropylmethyl) for expression of opioid antagonist activity.[17] Further studies demonstrated that the N-substituent in the phenylpiperidine antagonists controls their potency and efficacy.[15] Accordingly, there remains a need for compounds which have similar therapeutic effects as the trans-3,4-dimethyl-4-(3-hydroxyphenyl)piperidines, but are based on different structural elements.

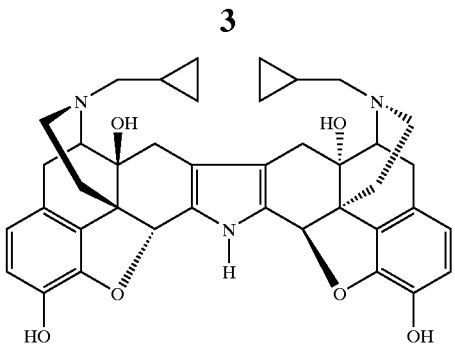

1

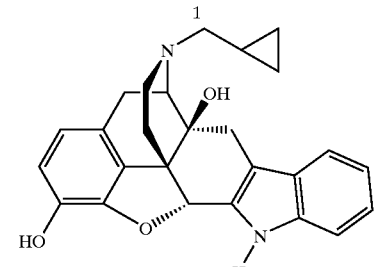

2

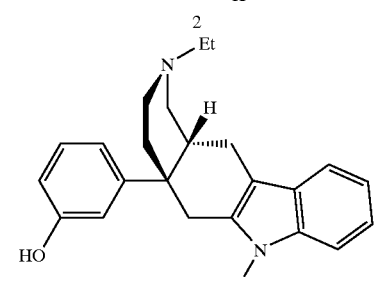

3

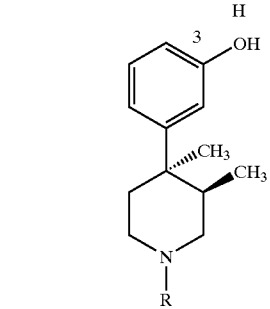

4a, R = substituent
4b, R = H (LY272922)

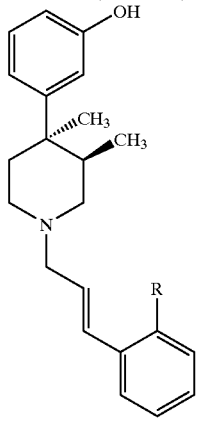

5a, R = H
5b, R = CH₃
5c, R = Cl

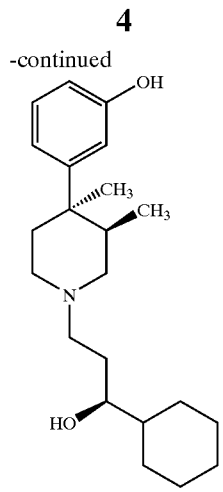

5d

6, R = CH₃
7, R = CH₂CH₂Ph

III

Numerous structural types of opioid agonists have been discovered, and several such as methadone, meperidine, fentanyl, and pentazocine as well as others have become important drugs for the treatment of pain.[10] However, there are only a few structural types that show potent, opioid pure antagonist activity.[10,7] A resurgence in heroin use in recent years coupled with the demonstrated effectiveness of opioid antagonists for the treatment of other substances of abuse has spurred new interest in the development of novel antagonists for opioid receptors.[16]

The oxymorphone-related compounds such as naloxone (8a) and naltrexone (8b), where the antagonist activity is dependent upon the N-substituent, have received considerable attention over the past few decades.[10] For example, pioneering studies by Portoghese and coworkers lead to the development of the prototypical kappa and delta opioid receptor antagonists, norbinaltorphimine (1, nor-BNI) and naltrindole (2, NTI). In contrast, the N-substituted trans-3, 4-dimethyl-(3-hydroxyphenyl)piperidine (9a–d) class of pure antagonist has received relatively little attention. Studies with the N-methyl analog 9a as well as many other N-substituted analogs such as 9b, 9c (LY255582), and 9d showed that the pure antagonist activity was dependent on the 3-methyl substituent and its trans relative relationship to the 4-methyl substituent on the piperidine ring and, unlike the oxymorphone class, was independent of the nature of the N-substituent.[7,16,17,6,13,14] Interestingly, the 3,4-dimethyl cis isomer 9e was found to be a mixed agonist-antagonist. May and coworkers[18] reported that 2,9α-dimethyl-5-(3-hydroxyphenyl)morphan (10a), which has the 9-methyl group in a configuration comparable to the cis-3,4-dimethyl-4-(3-hydroxyphenyl)piperidine (9e) with the 5-(3- hydroxyphenyl) group locked in an equatorial conformation relative to the piperidine ring in the morphan structure, was a weak but pure antagonist.

Neither 2,9β-dimethyl-5-(3-hydroxyphenyl)morphan (10b) nor 2,4β-dimethyl-5-(3-hydroxyphenyl)morphan (10g) have not been reported, due to a lack of synthetic accessibility to these structural isomers. Accordingly, the successful synthetic preparation of 2,9β-morphans and 2,4β-morphans remains an important goal of in the field opioid receptor-binding compounds.

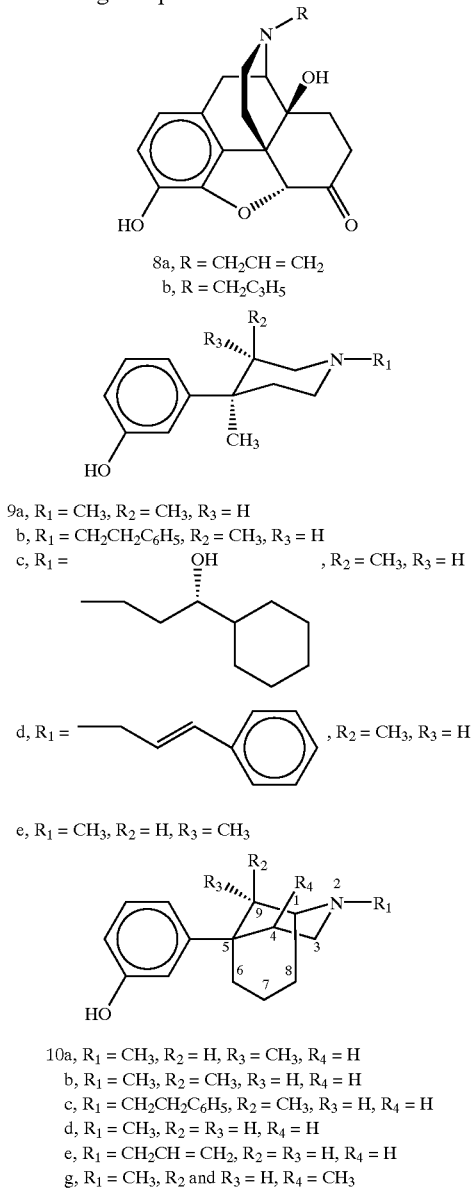

IV

In search of analgesics possessing a reduced side-effect profile relative to morphine, much effort has been expended towards finding opioids which operate via δ or κ opioid receptors as opposed to the μ opioid receptor which meditates the actions of morphine and its congeners.[10] BW373U86 (11)[19] and SNC-80 (12)[20] represent one class of opioid agonists discovered to be selective for the δ opioid receptor. Due to the lack of a clear opioid message substructure (i.e., a tyramine component similar to the enkephalins), compounds 11 and 12 have been referred to as non-classical opioid ligands.[5] The piperazine subunit of 11 and 12 is not commonly found in compounds showing activity at the opioid receptors. In contrast, piperidine ring compounds are found in many different classes of opioids.[27] If the internal nitrogen atom in compounds 11 or 12 is transposed with the benzylic carbon, piperidine ring analogs such as 13 would be obtained. Even though there are common structural elements between structures 11 or 12 and 13, the expected difference between in basicity between the piperidinyl amino group of 11 or 12 and the di-phenyl substituted amine of 13 is sufficient such that it cannot be predicted whether similarity to suggest that 13 would interact with opioid receptors similar to 11 or 12. It is also interesting to note that compound 13 has some structural elements in common with cis-3-methylfentanyl (14),[21,22] a non-classical opioid ligand selective for the mu opioid receptor. Accordingly, the preparation of compound 13 and related structures remains an important goal.

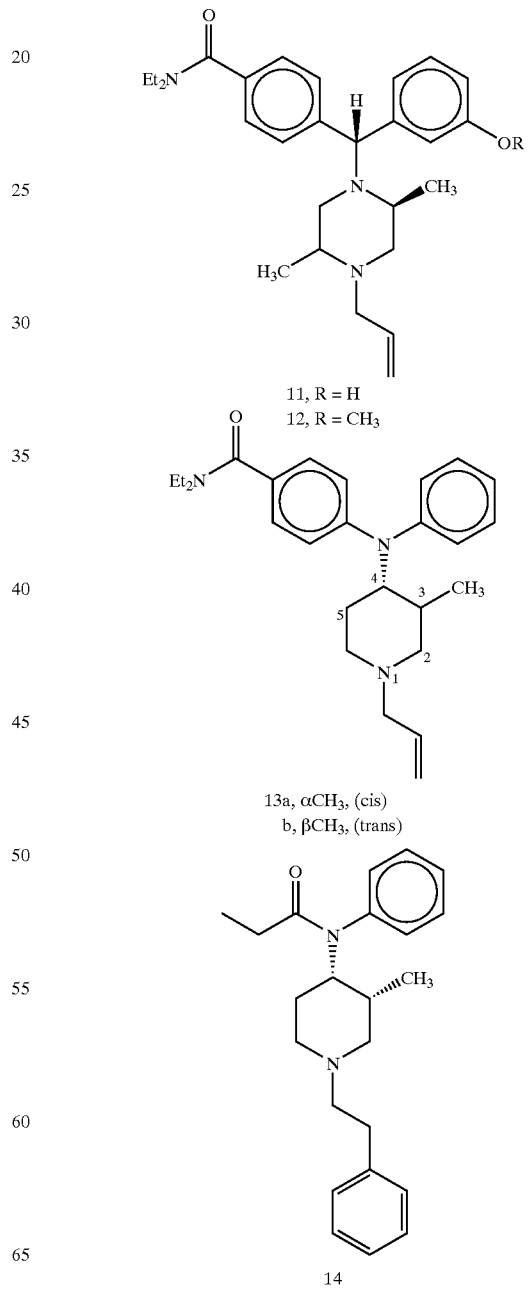

REFERENCES (1) Dhawan, B. N.; Cesselin, F.; Raghubir, R.; Reisine, T.; Bradley, P. B.; Portoghese, P. S.; Hamon, M. International Union of Pharmacology. XII. Classification of opioid receptors. *Pharmacol. Rev.* 1996, 48, 567–592.

(2) Martin, W. R. The evolution of concepts of opioid receptors. In *The Opiate Receptors*, Pasternak, G. W. Eds.; Humana Press Inc.: New Jersey, 1988, pp. 3–22.

(3) Portoghese, P. S.; Nagase, H.; Lipkowski, A. W.; Larson, D. L.; Takemori, A. E. Binaltorphimine-related bivalent ligands and their kappa opioid receptor antagonist selectivity [published erratum appears in J. Med. Chem. 1988 October;31(10):2056]. *J. Med. Chem.* 1988, 31, 836–841.

(4) Portoghese, P. S. An approach to the design of receptor-type-selective non-peptide antagonists of peptidergic receptors: δ opioid antagonists. *J. Med. Chem.* 1991, 34(6), 1757–1762.

(5) Dondio, G.; Ronzoni, S.; Eggleston, D. S.; Artico, M.; Petrillo, P.; Petrone, G.; Visentin, L.; Farina, C.; Vecchietti, V.; Clarke, G. D. Discovery of a novel class of substituted pyrrolooctahydroisoquinolines as potent and selective δ opioid agonists, based on an extension of the message-address concept. *J. Med. Chem.* 1997, 40, 3192–3198.

(6) Zimmerman, D. M.; Nickander, R.; Horng, J. S.; Wong, D. T. New structural concepts for narcotic antagonists defined in a 4-phenylpiperidine series. *Nature* 1978, 275, 332–334.

(7) Zimmerman, D. M.; Leander, J. D. Invited perspective, selective opioid receptor agonists and antagonists: Research tools and potential therapeutic agents. *J. Med. Chem.* 1990, 33, 895–902.

(8) Rothman, R. B.; Gorelick, D. A.; Eichmiller, P. R.; Hill, B. H.; Norbeck, J.; Liberto, J. G. An open-label study of a functional opioid kappa antagonist in the treatment of opioid dependence. In *Problems of Drug Dependence*, 1997. Proceedings of the 59th Annual Scientific Meeting, The College on Problems of Drug Dependence, Inc., Harris, L. S. Eds.; U. S. Department of Health and Human Services: Rockville, Md., 1997; Vol. 178, pp. 309.

(9) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and μ receptor subtype-selectivity in (+)-(3R, 4R)-dimethyl-4-(3-hydroxyphenyl)piperidine opioid antagonists. *J. Med. Chem.* 1998, 41(11), 1980–1990.

(10) Aldrich, J. V. Analgesics. In *Burger's Medicinal Chemistry and Drug Discovery*, Wolff, M. E. Eds.; John Wiley & Sons, Inc.: 1996; Vol. 3: Therapeutic Agents.

(11) Mitch, C. H.; Leander, J. D.; Mendelsohn, L. G.; Shaw, W. N.; Wong, D. T.; Cantrell, B. E.; Johnson, B. G.; Reel, J. K.; Snoddy, J. D.; Takemori, A. E.; Zimmerman, D. M. 3,4-Dimethyl-4-(3-hydroxyphenyl)piperidines: Opioid antagonists with potent anorectant activity. *J. Med. Chem.* 1993, 36(20), 2842–2850.

(12) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence*, 1978, pp. 237–247.

(13) Zimmerman, D. M.; Smits, S. E.; Hynes, M. D.; Cantrell, B. E.; Leander, J. D.; Mendelsohn, L. G.; Nickander, R. *Drug Alcohol Depend.* 1985, 14, 381–402.

(14) Mitch, C. H.; Leander, J. D.; Mendelsohn, L. G.; Shaw, W. N.; Wong, D. T.; Zimmerman, D. M.; Gidda, S. J.; Cantrell, B. E.; Scoepp, D. D.; Johnson, B. G.; Leander, J. D. *J. Med. Chem.* 1994, 37, 2262–2265.

(15) Evans, D. A.; Mitch, C. H.; Thomas, R. C.; Zimmerman, D. M.; Robey, R. L. Application of metalated enamines to alkaloid synthesis. An expedient approach to the synthesis of morphine-based analgesics. *J. Am. Chem. Soc.* 1980, 102, 5955–5956.

(16) Kreek, M. J. Opiates, opioids and addiction. *Mol. Psychiatry* 1996, 1(3), 232–254.

(17) Zimmerman, D. M.; Gidda, J. S.; Cantrell, B. E.; Schoepp, D. D.; Johnson, B. G.; Leander, J. D. Discovery of a potent, peripherally selective trans-3,4-dimethyl-4-(3-hydroxyphenyl)piperidine opioid antagonist for the treatment of gastrointestinal motility disorders. *J. Med. Chem.* 1994, 37(15), 2262–2265.

(18) Awaya, H.; May, E. L.; Aceto, M. D.; Merz, H.; Rogers, M. E.; Harris, L. S. Racemic and optically active 2,9-dimethyl-5-(m-hydroxyphenyl)morphans and pharmacological comparison with the 9-demethyl homologues. *J. Med. Chem.* 1984, 27, 536–539.

(19) Chang, K. J.; Rigdon, G. C.; Howard, J. L.; McNutt, R. W. A novel potent and selective nonpeptidic delta opioid receptor agonist, BW373U86. *J. Pharm. Exp. Ther.* 1993, 267, 852–857.

(20) Calderon, S. N.; Rothman, R. B.; Porreca, F.; Flippen-Anderson, J. L.; McNutt, R. W.; Xu, H.; Smith, L. E.; Bilsky, E. J.; Davis, P.; Rice, K. C. Probes for narcotic receptor mediated phenomena. 19. Synthesis of (+)-4-[(αR)-α-(2S,5R)-4-allyl-2,5-dimethyl-1-piperazinyl)-3-methoxybenzyl]-N,N-diethylbenzamide (SNC-80): A highly selective, nonpeptide δ opioid receptor agonist. *J. Med. Chem.* 1994, 37, 2125–2128.

(21) Van Bever, W. F.; Niemegeers, C. J. E.; Janssen, P. A. J. Synthetic analgesics. Synthesis and pharmacology of the diastereoisomers of N-(3-methyl-1-(2-phenylethyl)-4-piperidyl)-N-phenylpropanamide and N-(3-methyl-1-(1-methyl-2-phenylethyl)-4-piperidyl)-N-phenylpropanamide. *J. Med. Chem.* 1974, 17(10), 1047–1051.

(22) Xu, H.; Kim, C.-H.; Zhu, Y. C.; Weber, R. J.; Rice, K. C.; Rothman, R. B. (+)-cis-Methylfentanyl and its analogs bind pseudoirreversibly to the mu opioid binding site: Evidence for pseudoallosteric modulation. *Neuropharmacology* 1991, 30, 455–462.

SUMMARY OF THE INVENTION

It is an object of the present invention to provide novel compounds which bind to opioid receptors.

It is another object of the present invention to provide novel compounds which are opioid receptors antagonists that bind with high affinity.

It is another object of the present invention to provide novel opiates that are selective for the kappa receptor as compared to the delta and mu receptors.

It is another object of the present invention to provide novel opiates that are selective for the mu and kappa receptors as compared to the delta receptor.

It is another object of the present invention to provide novel opiates that are selective for the delta receptor as compared to the mu and kappa receptors.

It is another object of the present invention to provide novel opiates that are pure antagonists at the mu, delta and kappa receptors.

It is another object of the present invention to provide methods of making the novel compounds.

It is another object of the present invention to provide methods of treating a variety of disease states with the novel opiate compounds of the present invention.

The objects of the present invention may be accomplished with compounds represented by formula (I), or pharmaceutically acceptable salts thereof:

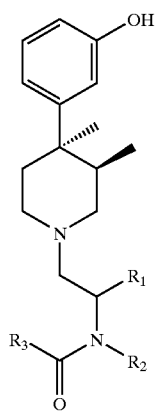
(I)

where
R$_1$ is hydrogen, an alkyl group, an aryl group, or an aralkyl group;
R$_2$ is hydrogen, an alkyl group, an aryl group, or an alkaryl group; and
R$_3$ is

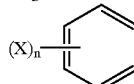 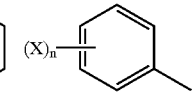 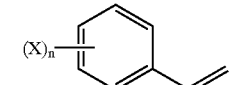

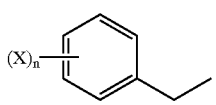

each X is, independently, halogen, —OH, —OR, an alkyl group, an aryl group, —NH$_2$, —NHR, —N(R)$_2$, —CF$_3$, —CN or —C(O)NH$_2$, —C(O)NHR, or —C(O)N(R)$_2$;
each R is, independently, an alkyl group, an aryl group or an alkaryl group;
n is 0 or an integer from 1 to 5; and
R$_a$ is hydrogen or an alkyl group.

The objects above may also be accomplished with compounds represented by formula

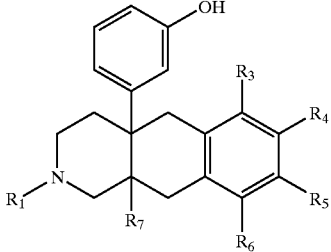
(II)

(II): or pharmaceutically acceptable salts thereof, where
R$_1$ is an alkyl group or aralkyl group; and
R$_3$, R$_4$, R$_5$, R$_6$ are each, independently, hydrogen, an alkyl group, —OH, —NH$_2$, —NHR, —N(R)$_2$, halogen, —OR, —CF$_3$, —CN, —NO$_2$, or —NHC(O)R;
each R is, independently, an alkyl group, an aryl group, or an alkaryl group; and
R$_7$ is hydrogen or an alkyl group.

The objects of the present invention may be also accomplished with compounds represented by formula (III), or pharmaceutically acceptable salts thereof:

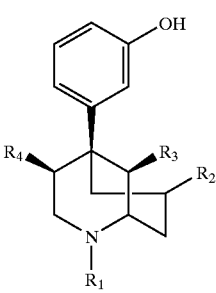
(III)

where
R$_1$ is an alkyl group or an aralkyl group;
R$_2$ is hydrogen, an alkyl group, an aralkyl group, =O, —NH$_2$, —NHR, —N(R)$_2$, —NHC(O)R, —NRC(O)R, —NHC(O)R$_5$, or —NRC(O)R$_5$;
R$_3$ and R$_4$ may be hydrogen or methyl, with the proviso that when R$_3$ is methyl then R$_4$ is hydrogen and when R$_3$ is hydrogen then R$_4$ is methyl;
each R is, independently, an alkyl group, an aryl group, or an alkaryl group; and
R$_5$ is

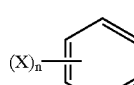 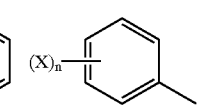 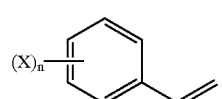

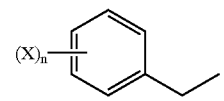

each X is, independently, halogen, —OH, —OR, an alkyl group, an aryl group, —NH$_2$, —NHR, —N(R)$_2$, —CF$_3$, —CN, —C(O)NH$_2$, —C(O)NHR, or —C(O)N(R)$_2$;
each R is, independently, an alkyl group, an aryl group, or an alkaryl group;
n is 0 or an integer from 1 to 5; and
R$_a$ is hydrogen or an alkyl group.

The objects above may be accomplished with compounds represented by formula (IV), or pharmaceutically acceptable salts thereof:

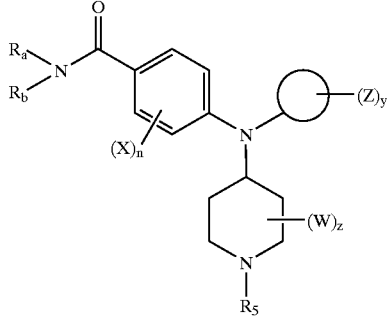
(IV)

where
R$_a$ and R$_b$ are each, independently, hydrogen or an alkyl group, or R$_a$ and R$_b$, together, form a cycloalkyl group;

each X is, independently, an alkyl group;

O is a five- or six-membered aryl or heteroaryl group;

each Z is, independently, an alkyl group, —OH, —OR, halogen, —CF$_3$, —CN, —NH$_2$, —NHR, or —N(R)$_2$;

each R is, independently, an alkyl group, an aryl group, or an alkaryl group;

each W is an alkyl group;

n is 0 or an integer from 1 to 4;

y is 0 or an integer from 1 to 5;

z is 0 an integer from 1 to 8; and

R$_5$ is an alkyl group, alkenyl group, or aralkyl group.

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

Figure 1:
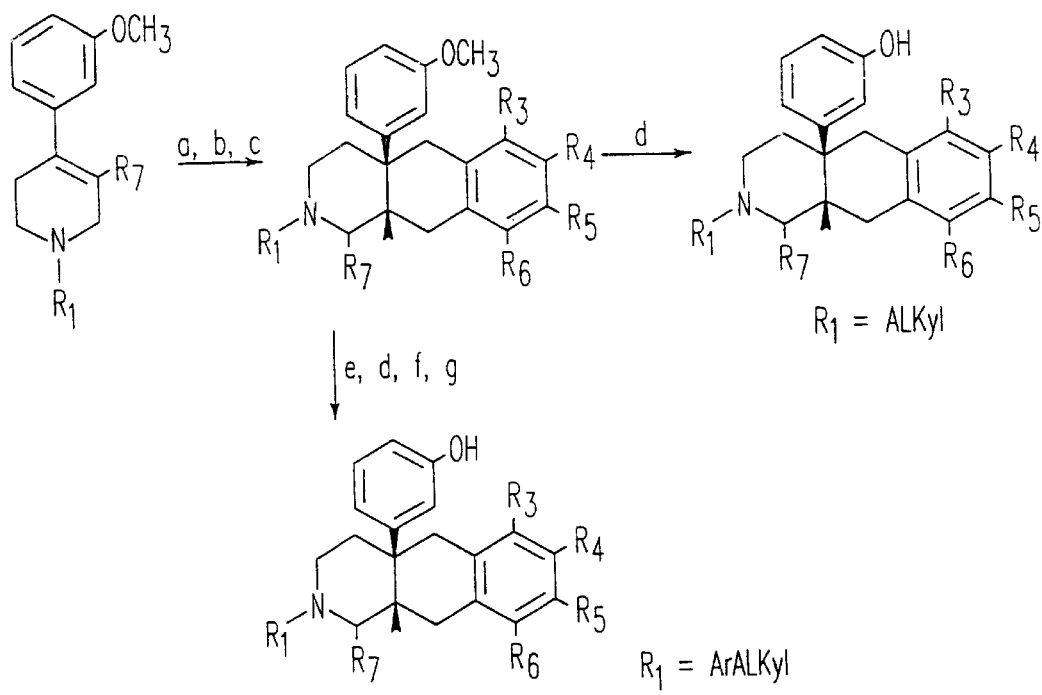
FIG. 1: Synthesis of compounds represented by formula (II).
Figure 1:
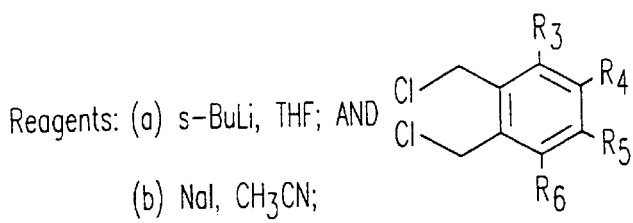

The present invention relates to a group of compounds that contain a piperidinyl, or a bridged piperidinyl group. The inventive compounds have been found to have a variety of different activities when bound to opioid receptors.

Compounds of Formula (I)

In formula (I), R$_1$ is hydrogen, an alkyl group or an aralkyl group. As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms. As used herein, the term "aralkyl group" refers to an aryl moiety bonded to an alkyl radical. The aryl moiety may have 6 to 20 carbon atoms. The aryl moiety may contain only carbon and hydrogen atoms. Alternatively, the aryl moiety may contain heteroatoms, for example 1, 2, or 3 heteroatoms (e.g., oxygen, nitrogen, and sulfur). A particularly preferred aryl moiety is phenyl-. The alkyl radical of the aralkyl group may as described above when R$_1$ is an alkyl group. The alkyl group or moiety and/or the aryl moiety may be substituted. Suitable substituents include halogens (F, Cl, Br and I), alkyl groups (e.g., C$_1$–C$_8$), alkoxy groups (e.g., C$_1$–C$_8$ alkoxy groups), —CF$_3$, —CN, —NH$_2$, —NHR, or —N(R)$_2$. The R groups are, independently, an alkyl group (such as described for R$_1$ in formula (I) above), an aryl group (such as phenyl) or an aralkyl group group (such as benzyl). In groups in compounds of formula (I)–(IV) where two R groups are bonded to the same atom, i.e., —N(R)$_2$, the R groups may, together, form a cyclic alkyl group. Such a cyclic alkyl group may, preferably, contain 2 to 8 carbon atoms, with 4 or 5 carbon atoms particularly preferred.

Preferably, R$_1$ is unsubstituted. In a preferred embodiment, R$_1$ is a C$_1$–C$_8$ alkyl group or a C$_6$–C$_{10}$ aryl-C$_1$–C$_8$-alkyl group. In a more preferred embodiment, R$_1$ is a C$_1$–C$_4$ alkyl group or a phenyl-C$_1$–C$_4$-alkyl group. Even more preferably, R$_1$ is a C$_1$–C$_3$ alkyl group or a phenyl-C$_1$–C$_3$-alkyl group. Most preferably, R$_1$ is a methyl group, an isopropyl group, or a phenethyl group.

R$_2$ in formula (I) may be hydrogen, an alkyl group, an aryl group or an alkaryl group. Suitable alkyl and alkaryl groups are as described for R$_1$ above. The aryl group may be as described for the aryl moiety of R$_1$ above. Preferably, R$_2$ is hydrogen.

R$_3$ in formula (I) is one of the following groups:

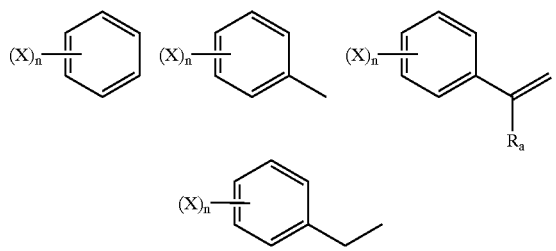

In these groups, the phenyl ring may be unsubstituted (n is 0) or substituted with 1, 2, 3, 4, or 5 X groups. each X is, independently, halogen (e.g., chlorine or fluorine), —OH, —OR, an alkyl group (such as described for $R_1$ in formula (I) above), an aryl group (such as phenyl), —$NH_2$, —NHR, —$N(R)_2$, —$CF_3$, —CN, —$C(O)NH_2$, —C(O)NHR, or —$C(O)N(R)_2$. The R groups are, independently, an alkyl group (such as described for $R_1$ in formula (I) above), an aryl group (such as phenyl) or an aralkyl group group (such as benzyl). Preferred X groups are chlorine, fluorine, —OH, —$OCH_3$ and —$NH_2$. Preferably, n is 1. The X group(s) may be located at the ortho, meta and para positions. The para position is preferred, especially when X is —OH.

$R^a$ in the formulas above may be hydrogen or an alkyl group. Suitable alkyls are as described for $R_1$ in formula (I) above. Preferably, $R_a$ is hydrogen or methyl.

The absolute configuration of the carbon atom to which $R_1$ is bonded may be (R) or (S). The (S) configuration is preferred.

The compounds of formula (I) are preferably opiates with preferential affinity for the $\mu/\kappa$ opioid receptors and comparably less affinity for $\delta$ receptors. In a preferred embodiment, these compounds are pure antagonists. The ratio of affinity for the $\delta$ receptor to the $\kappa$ receptor ($\delta/\kappa$) may be at least 1.5, preferably at least 2.0, more preferably at least 20, still more preferably at least 100, even still more preferably at least 750 and most preferably at least 800. The $\mu/\kappa$ ratio may be 0.002 to 500.

The compounds of formula (I) may be prepared using well-known synthetic techniques by condensing an acid of the formula $R_3$—$CO_2H$ with an amine represented by the formula:

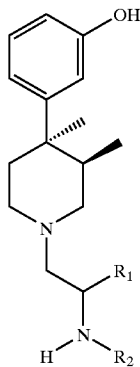

The acid is preferably converted into an activated ester in order to couple with the amine. A BOP ester is preferred. In a particularly preferred embodiment, a variety of compounds within the scope of formula (I) may be simultaneously synthesized and evaluated using well-established combinatorial synthesis techniques, for example, as described in Example 1.

Compounds of Formula (II)

In formula (II), $R_1$ is an alkyl group or an aralkyl group. These groups may be as defined for $R_1$ in formula (I). In a preferred embodiment, $R_1$ is a $C_1$-$C_8$ alkyl group or a $C_6$-$C_{10}$ aryl-$C_1$-$C_8$-alkyl group. In a more preferred embodiment, $R_1$ is a $C_1$-$C_4$ alkyl group or a phenyl-$C_1$-$C_4$-alkyl group. Even more preferably, $R_1$ is a $C_1$-$C_2$ alkyl group or a phenyl-$C_1$-$C_3$-alkyl group. Most preferably, $R_1$ is a methyl group or a phenethyl group.

$R_7$ is hydrogen or an alkyl group, preferably an alkyl group. Suitable alkyl groups are as described above for $R_1$. Preferably, $R_7$ is methyl.

The substituents $R_3$, $R_4$, $R_5$ and $R_6$ on the fused aromatic ring may be, independently, hydrogen, an alkyl group, —OH, —$NH_2$, —NHR, —$N(R)_2$, halogen (e.g., fluorine and chlorine), —OR, —$CF_3$, —CN, —$NO_2$, or —NHC(O)R. The R groups are, independently, an alkyl group (such as described for $R_1$ in formula (I) above), an aryl group (such as phenyl) or an aralkyl group group (such as benzyl). Methyl and ethyl are the more preferred alkyl groups, and methyl is most preferred. Methoxy is a preferred —OR group. In one embodiment, $R_3$, $R_4$, $R_5$ and $R_6$ are each hydrogen. In another embodiment, at most three of $R_3$, $R_4$, $R_5$ and $R_6$ are other than hydrogen. In another embodiment, at most two of $R_3$, $R_4$, $R_5$ and $R_6$ are other than hydrogen. In yet another embodiment, only one of $R_3$, $R_4$, $R_5$ and $R_6$ is other than hydrogen. In an embodiment where the fused aromatic ring contains alkyl groups, one, two or three of $R_3$, $R_4$, $R_5$ and $R_6$ are alkyl groups.

The stereochemical relationship between $R_7$ and the hydroxyphenyl group may be cis or trans. The cis stereochemistry is preferred. All optical isomers of these compounds are within the scope of the present invention.

The compounds of formula (II) are opiates which are preferably pure opioid receptor antagonists. In a particularly preferred embodiment, the opiates are selective for the mu and/or kappa receptor as compared to delta receptors. The $\delta/\kappa$ selectivity may be at least 2:1, but is preferably higher, such as at least 5:1, 10:1, 20:1, 25:1, 30:1 or 50:1. The $\delta/\kappa$ selectivity may be at least 2:1, but is preferably higher, such as at least 5:1, 10:1,15:1, 20:1, 25:1, 30:1, or 50:1.

The compounds of formula (II) may be prepared, for example, as shown FIG. 1. These compounds may also be prepared as described in Examples 2 and 3 with appropriate modification of the various R groups.

Compounds of Formula (III)

In formula (III), $R_1$ may be an alkyl group or an aralkyl group. These groups may be as defined for $R_1$ in formula (I). In a preferred embodiment, $R_1$ is a $C_1$-$C_8$ alkyl group or a $C_6$-$C_{10}$ aryl-$C_1$-$C_8$-alkyl group. In a more preferred embodiment, $R_1$ is a $C_1$-$C_4$ alkyl group or a phenyl-$C_1$-$C_4$-alkyl group. Even more preferably, $R_1$ is a $C_1$-$C_2$ alkyl group or a phenyl-$C_1$-$C_3$-alkyl group. Most preferably, $R_1$ is larger than a methyl group, such as a phenethyl group.

$R_2$ in these compounds may be hydrogen, an alkyl group, an aralkyl group, =O, —$NH_2$, —NHR, —$N(R)_2$, —NHC(O)R, —NRC(O)R, —$NHC(O)R_5$., or —$NRC(O)R_5$. The alkyl or aralkyl group may be as described for $R_1$ in formula (I). The R groups are, independently, an alkyl group (such as described for $R_1$ in formula (I) above), an aryl group (such as phenyl) or an aralkyl group group (such as benzyl). The $R_5$ group of formula (III) has the same structure for $R_3$ in formula (I) discussed above. All of the embodiments described for $R_3$ in formula (I) apply to $R_5$ in formulla (III). Preferably, $R_2$ is hydrogen, an alkyl group, or an amido group, i.e., —$NHC(O)R_5$., or —$NRC(O)R_5$. More preferably, $R_2$ is hydrogen or an amido group.

$R_3$ and $R_4$ may be hydrogen or methyl. However, when $R_3$ is methyl then $R_4$ is hydrogen and when $R_3$ is hydrogen then $R_4$ is methyl.

The compounds of formula (III) are preferably opiates which are opioid receptor pure antagonists. When $R_2$ is hydrogen, these compounds have a preferential affinity for the $\mu$ receptors, as compared to $\kappa$ or $\delta$ receptors. In this embodiment, the $\mu/\delta$ selectivity may be at least 2:1, but is preferably higher, e.g., at least 5:1, 10:1, 25:1, 50:1, 100:, 150:1 or 200:1. In this embodiment, the $\mu/\kappa$ selectivity may be at least 2:1, 5:1, 10:1 or 25:1. When $R_2$ is an amido group, the $\delta/\mu$ selectivity may be at least 2:1, but is preferably higher, e.g., at least 5:1, 10:1, 25:1 or 50:1.

Figure 2A:
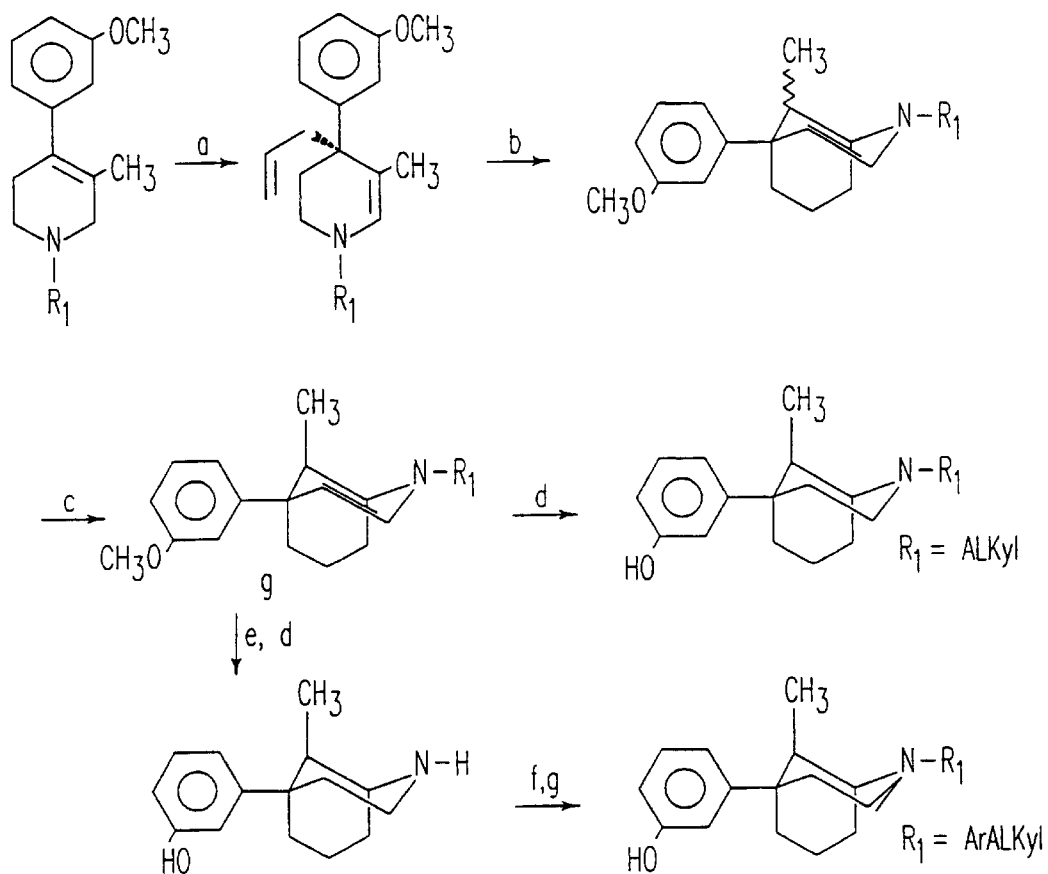
FIG. 2: Synthesis of compounds represented by formula (III). (A) synthesis of compounds in which R$_3$ is methyl (9β-compounds). (B) synthesis of compounds in which R$_4$ is methyl (4β-compounds).
Figure 2B:
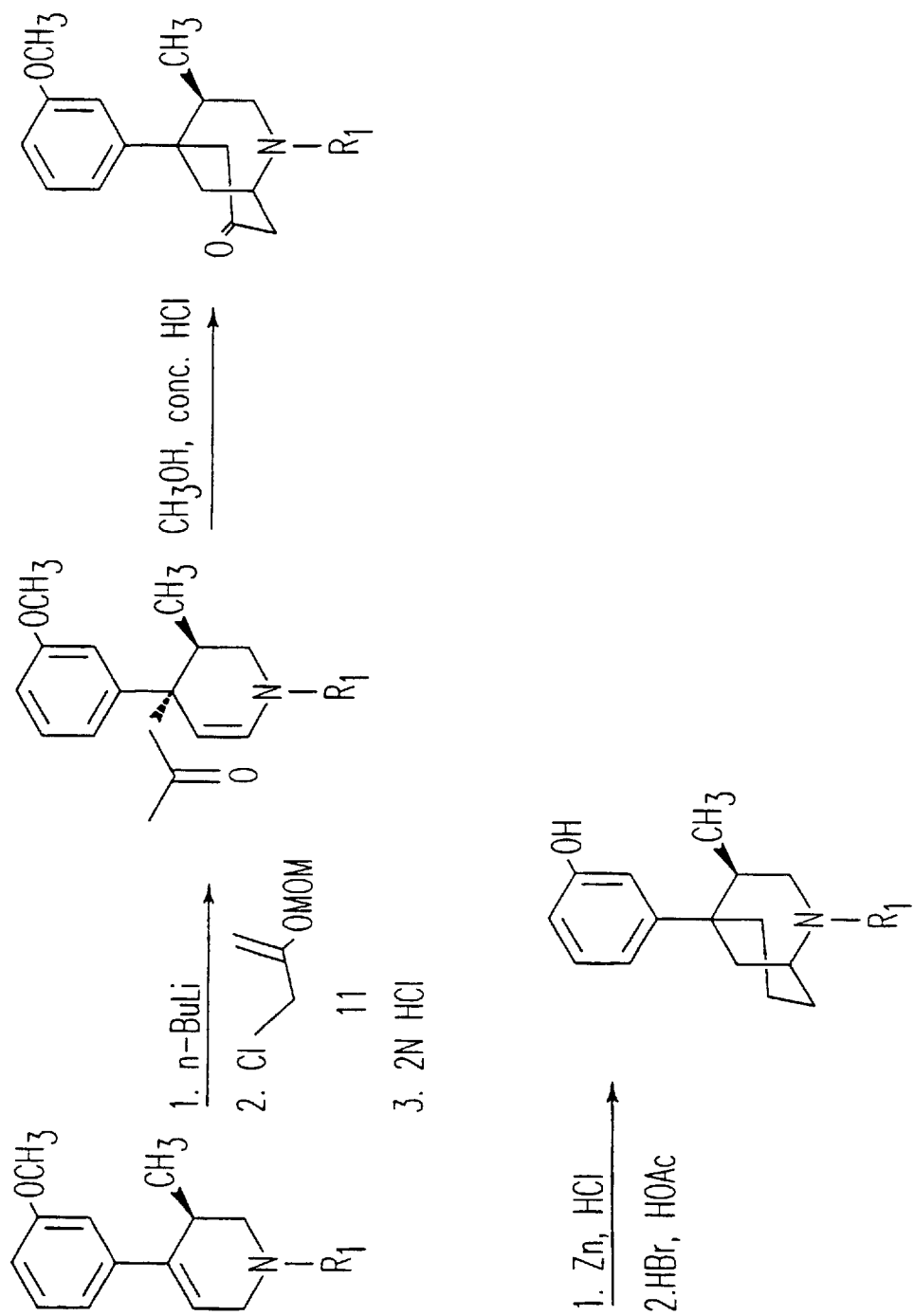

The compounds of formula (III) may be synthesized, for example, as shown in FIG. 2. The synthesis of compounds in which $R_3$ is methyl (9β-compounds) is shown in FIG. 2A. Compounds in which $R_4$ is methyl (4β-compounds) may be synthesized as shown in FIG. 2B. For specific examples of such preparations, see the following Examples 3–5 and 7.

Compounds of Formula (IV)

$R_a$ and $R_b$ are each, independently, hydrogen or an alkyl group. The alkyl group may be as described for $R_1$ in formula (I). Preferably, $R_a$ and $R_b$ are ethyl. Alternatively, $R_a$ and $R_b$, together, form a cycloalkyl group. Suitable cycloalkyl groups include those having 3 to 7 carbon atoms. Cycloalkyl groups having four or five carbon atoms are especially preferred.

Each X, if present, may be an alkyl group. Suitable alkyl groups are as described for $R_1$ in formula (I) above. The number of X groups, determined by the variable n, may be 0, 1, 2, 3 or 4. Preferably, n is 0.

The group o is a five- or six-membered aryl or heteroaryl group. Phenyl is the preferred aryl group. Suitable heteroaryl groups may have one, two, three or four heteroatoms, e.g., nitrogen, oxygen or sulfur. Specific examples of heteroaryl groups include pyridine, pyridazine, pyrimidine, pyrazine, traiazine (e.g., 1,2,3-; 1,2,4-; 1,3,5-), 1,2,4,5-tetrazine, furan, thiophene, oxazole, isothiazole, thiadazole, pyrazole, pyrrole, and imidazole.

Preferably, o is a phenyl group. These compounds are represented by the formula:

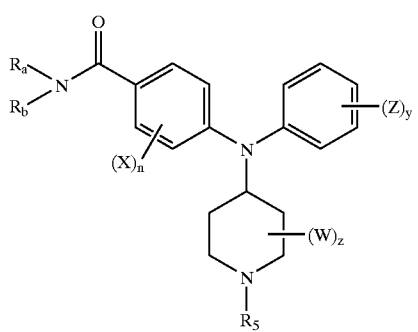

(IVa)

Each Z, if present, is, independently, an alkyl group, —OH, —OR, halogen, —CF$_3$, —CN, —NH$_2$, —NHR, or —N(R)$_2$;. The R groups are, independently, an alkyl group (such as described for $R_1$ in formula (I) above), an aryl group (such as phenyl) or an aralkyl group group (such as benzyl) Suitable alkyl groups are as described for $R_1$ in formula (I) above. The number of Z groups, determined by the variable y, may be 0, 1, 2, 3, 4, or 5. Preferably, y is 1 or 0. More preferably, y is 0.

Each W, if present, is an alkyl group. Suitable alkyl groups are as described for $R_1$ in formula (I) above. Preferably, W is a methyl. The number of alkyl groups on the piperdine ring is determined by z. The variable z may be 0 or an integer from 1 to 8, inclusive of 2, 3, 4, 5, 6, or 7. Preferably, z is 1, 2, or 3. In a preferred embodiment, at least one W group is bonded to a carbon atom adjacent to the carbon atom bearing the diamino substituent. The stereochemical relationship between this W group and the diamino substituent may be cis or trans. When multiple W groups are present on the piperdine ring, the stereochemical relationship between W the groups may be cis or trans.

In formula (IV), $R_5$ is an alkyl group, an alkenyl group, or an aralkyl group. The alkyl group and/or the aralkyl group may be as defined for $R_1$ in formula (I). Preferably, these groups have 1 to 8 carbon atoms, more preferably 1 to 5 carbon atoms. The alkenyl group may have up to three double bonds, more preferably, up to two double bonds, and, most preferably, one double bond. An alkenyl group is preferred. Most preferably, $R_5$ is an allyl group.

The compounds formula (IV) are opiates which are preferably agonists that are selective for the delta receptor. The $\delta/\mu$ selectivity may be at least 2:1, but is preferably higher, e.g., at least 5:1, 10:1, 25:1, 50:1, 100:1 or 200:1. The $\delta/\kappa$ selectivity may be at least 2:1, but is preferably higher, e.g., at least 5:1, 10:1, 25:1, 50:1, 100:1, 200:1, 250:1 or 500:1.

Figure 3:
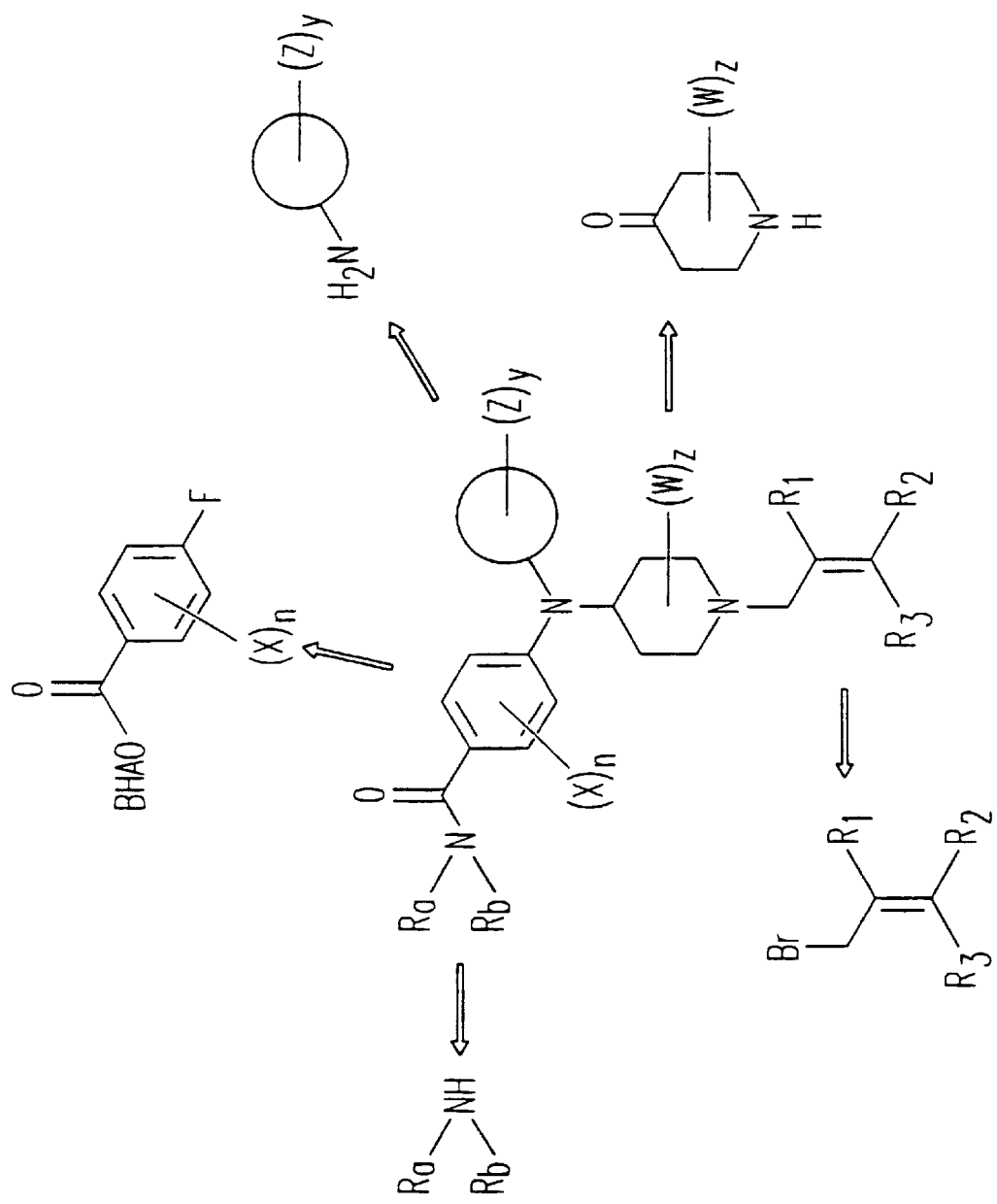
FIG. 3: Retrosynthetic analysis for the synthesis of compounds represented by formula (IV).
Figure 4:
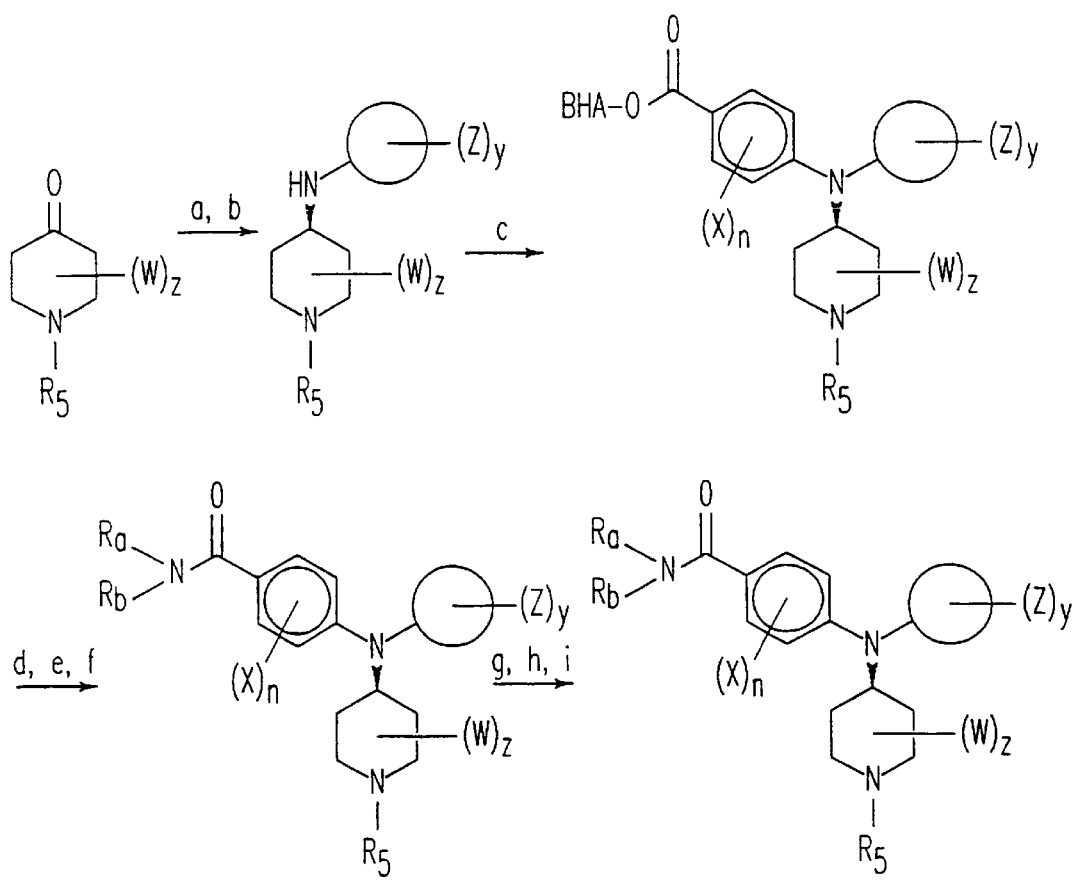
FIG. 4: Synthesis of compounds represented by formula (IV).

The compounds of formula (IV) may be synthesized, for example, in accordance with the retrosynthetic analysis shown in FIG. 3. An example of a reaction sequence to obtain compounds of formula (IV) is shown in FIG. 4. For specific examples of syntheses of compounds of formula (IV), see the Example 6 below.

Compounds (I)–(IV) may be in the form of a pharmaceutically acceptable salt via protonation of the amine with a suitable acid. The acid may be an inorganic acid or an organic acid. Suitable acids include, for example, hydrochloric, hydroiodic, hydrobromic, sulfuric, phosphoric, citric, acetic and formic acids.

The receptor selectivities discussed above are determined based on the binding affinities at the receptors indicated.

The compounds of the present invention may be used to bind opioid receptors. Such binding may be accomplished by contacting the receptor with an effective amount of the inventive compound. Of course, such contacting is preferably conducted in a aqueous medium, preferably at physiologically relevant ionic strength, pH, etc.

The inventive compounds may also be used to treat patients having disease states which are ameliorated by binding opioid receptors. Such diseases states include heroin addiction, pain, i.e., the compounds are used as analgesics. The compounds of the inventive may also be used to reverse mu-induced respiratory depression, as cytostatica agents, as antimigraine agents, as immunomodulators, as immunosuppressives, as antiartiritic agents, as antiallergic agents, as virucides, to treat diarrhea, as antidepressants, as uropathic agents, as antitussives, as antiadditive agents, as anti-smoking agents, to treat alcoholism, as hypotensive agents, or to treat obesity.

The compounds may be administered in an effective amount by any of the conventional techniques well-established in the medical field. For example, the compounds may be administered orally, intraveneously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480–590, incorporated herein by reference. The patient is preferably a mammal, with human patients especially preferred.

Having generally described this invention, a further understanding can be obtained by reference to certain specific examples which are provided herein for purposes of illustration only and are not intended to be limiting unless otherwise specified. In each of the Examples, the numbering of compounds and references cited are specific to each Example.

EXAMPLES

Example 1

Identification of Opiates Selective for the Opioid Receptors

Summary

A three-component library of compounds was prepared in parallel using multiple simultaneous solution phase synthetic methodology. The compounds incorporated a (+)-(3R,4R)-dimethyl-4-(3-hydroxyphenyl)piperidine group as one of the monomers. The other two monomers, which included N-substituted or unsubstituted Boc protected amino acids and a range of substituted aryl carboxylic acids, were selected to add chemical diversity. Screening of these compounds in competitive binding experiments with the kappa opioid receptor selective ligand [$^3$H]U69,593 led to the identification of a κ opioid receptor selective ligand, N-{(2'S)-[3-(4-hydroxyphenyl)propanamido]-3'-methylbutyl}-(3R,4R)-dimethyl-4-(3-hydroxyphenyl)piperidine (8, RTI-5989-29). Additional SAR studies suggested that 8 possesses lipophilic and hydrogen bonding sites that are important to its opioid receptor potency and selectivity. These sites appear to exist predominantly within the kappa receptor since the selectivity arises from a 530-fold loss of affinity of 8 for the mu receptor and an 18-fold increase in affinity for the kappa receptor relative to the mu-selective ligand, (+)-N-[trans-4-phenyl-2-butenyl]-(3R,4R)-dimethyl-4-(3-hydroxyphenyl)piperidine (5a). This degree of selectivity observed in the radioligand binding experiments was not observed in the functional assay. According to its ability to inhibit agonist stimulated binding of [$^{35}$S] GTPγS at all three opioid receptors, compound 8 behaves as a mu/kappa opioid receptor pure antagonist with negligible affinity for the delta receptor.

Chemistry

Figure 5:
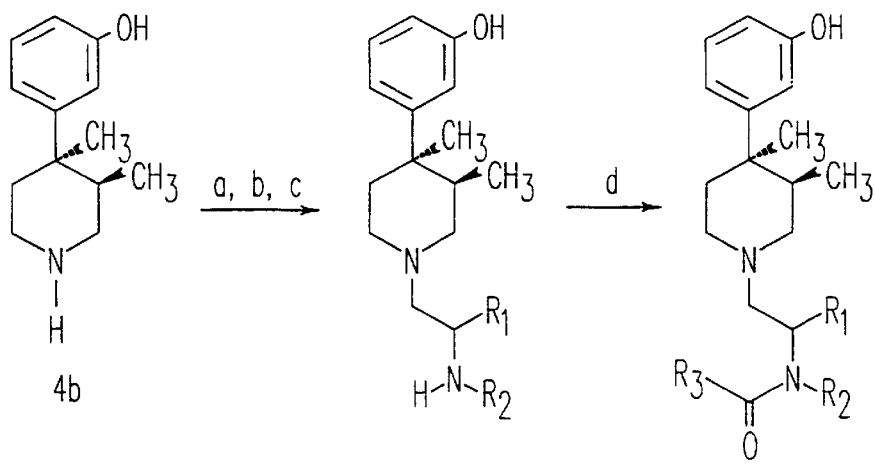
FIG. 5: Synthesis of compounds (7) as described in Example 1.
Figure 5:
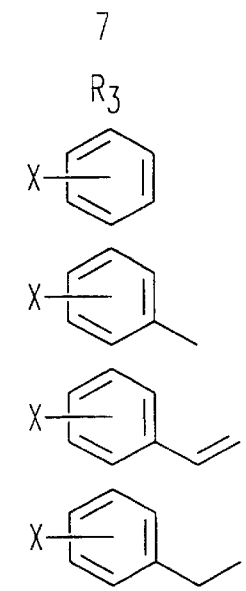

Coupling of (+)-(3R,4R)-dimethyl-4-(3-hydroxyphenyl) piperidine (4b) (FIG. 5) with an appropriate tert-butoxycarbonyl-protected amino acid (Boc-protected) followed by removal of the Boc-protecting group with trifluoroacetic acid (TFA) in methylene chloride followed by reduction using a tetrahydrofuran (THF) solution of borane-dimethyl sulfide complex gave the intermediate amines (6a–k) in 15–78% yields (FIG. 5). These intermediates 6 were subjected to column chromatography or crystallization as necessary to obtain pure compounds. The final products (7) were prepared in scintillation vials via amide bond formation by coupling with a wide variety of commercially available carboxylic acids. A representative list of such carboxylic acids follows the Experimental section of this Example. Benzotriazol-1-yl-oxy-tris-(dimethylamino) phosphonium hexafluorophosphate (BOP reagent) in THF was employed as the coupling reagent which provided very clean products after aqueous work-up. These compounds were used directly in screening without additional purification. Pure compounds for further SAR analysis were obtained by purification of library samples or by single compound synthesis by conventional synthetic methodology and characterized by MS, $^1$H NMR, and elemental analyses.

Results and Discussion

Figure 6:
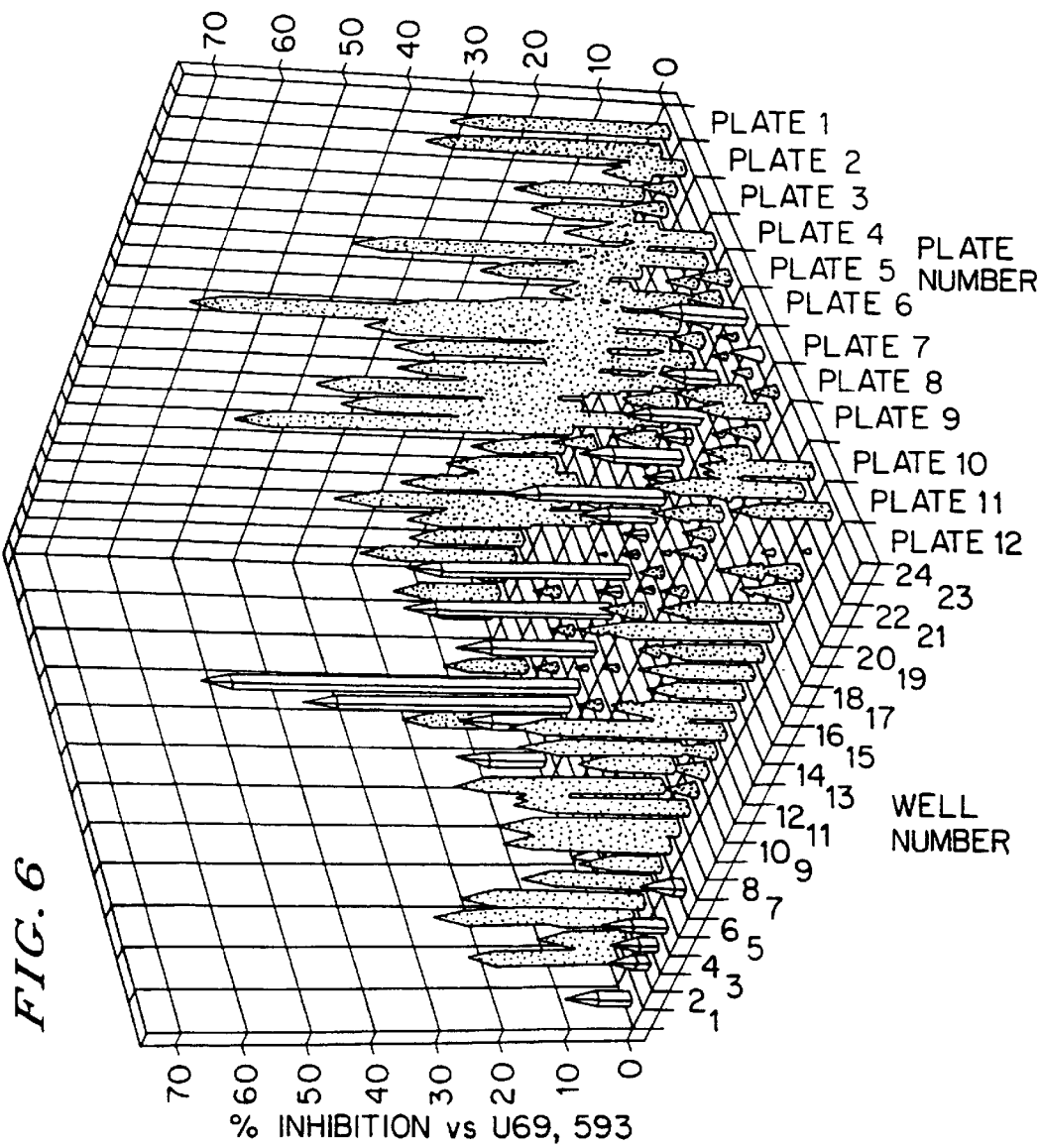
FIG. 6: Data from screening of library described in Example 1 at 100 nM against the kappa-selective ligand [$^3$H]U69,593 (percent inhibition).

The results from the screening of the 288-compound library in competitive binding against the kappa opioid receptor selective ligand [$^3$H]U69,593 are illustrated graphically in FIG. 6. Several compounds showed significant inhibition of radioligand binding at 100 nM with 8 (plate 4, well 20, 71%) being the best (FIG. 6). The data for % inhibition of [$^3$H]U69,593 binding by selected library compounds 8–23 at 100 nM are listed in Table 1.

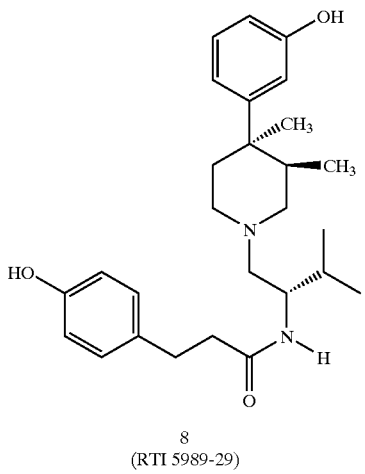

8
(RTI 5989-29)

A comparative analysis of the structures related to compounds 9–23, which have less binding affinity relative to 8, readily illustrates the importance for kappa receptor binding of each structural subunit of group $R_3$ (Table 1). Compound 9, a diastereomer of 8, where the carbon to which the $R_1$ isopropyl group is connected has the opposite stereochemistry, shows less binding affinity (11%) for the opioid kappa receptor. The sensitivity to orientation (R or S) at this stereogenic center suggests that the isopropyl group may be working in tandem with another structural feature of the $R_3$ unit to both increase binding in 8 and decrease binding in 9. The difference in affinity of compounds 8 (71%) and 10 (28%) suggests that the 4-hydroxyl substituent in 8 is more effective for high kappa binding affinity. Furthermore, the weaker inhibition displayed by compounds 11 (20%) and 12 (25%) possessing meta and ortho hydroxyl substituents respectively, pinpoints the para placement of the para-hydroxyl group as the optimum position. The fact that compound 19, which lacks the isopropyl group but has the para-hydroxyphenylpropionic substituent, shows less affinity (11% vs. 71%) relative to 8, adds additional support to the importance of the $R_1$ isopropyl and 4-hydroxyphenyl groups to the kappa-selective binding. The low affinity of compound 20 (20%) which has a methyl substituent in position ($R_1$) shows that a methyl group may be less effective than the isopropyl group. This strengthens the notion that both the isopropyl group ($R_1$) and the 4-hydroxyphenyl group for $R_3$ are working together to elicit high affinity binding at the kappa opioid receptor in compound 8. The results for compound 13 (6%) suggests that two methylene groups are more effective between the phenyl ring and the amide carbonyl in diversity element $R_3$, presumably because the para-hydroxyl group cannot reach its site of interaction in the truncated derivative. Furthermore, the lower inhibition of binding for compound 14 (15%) which incorporates a trans double bond in the connecting chain shows that the length of the chain is not optimal to impart high binding affinity, implying that flexibility is also preferred in this carbon chain to provide proper ligand and receptor alignment. The lower affinity of the 4-fluoro derivative 15 (26%) and the 4-methoxy derivative 18 (16%) supports the suggestion that a hydrogen bond exists between ligand 8 and the receptor with compound 8 donating the hydrogen. This is further supported by the lower affinity of the 3,4-dihydroxyl derivative 16 (31%) which can hydrogen bond internally and the 3-methoxy-4-hydroxy derivative 17 (42%) whose hydrogen bond could be sterically encumbered by interference from an adjacent methoxy group. Interestingly, all compounds having methyl and not hydrogen as the second diversity element $R_2$, 21 (0%), 22 (1%), and 23 (7%) displayed very low binding affinity usually at baseline (DMSO blank) levels. Apparently, position $R_2$ is preferably unsubstituted. These results suggest that the amide group may be part of a separate hydrogen-bonding interaction to place the key $R_1$ isopropyl and $R_3$ p-hydroxyphenyl rings in their correct positions for strong interaction with the receptor. Alternatively, the N-methyl substituent may be decrease ligand affinity through repulsive steric interactions.

Taken together, the data suggests that the high binding affinity displayed by 8 results from a combination of several structural features present in its N-substituent. These include a 4-hydroxyl group in the pendant phenyl ring of group $R_3$, the length and flexibility of the carbon chain connecting this ring to the amide carbonyl and the presence of a beta (position $R_1$) isopropyl group with an S configuration at the adjacent stereogenic center. The data analysis suggests that the principle stabilizing interactions could be related to binding of the hydroxyl and isopropyl substituents with the other atoms of the N-substituent substructure acting to hold these two binding elements in optimum overlapping positions within the receptor site. Alternatively, the isopropyl group could be acting to bias the conformation of molecule to provide the best alignment of the 4-hydroxyphenylpropionic acid side-chain with its binding site.

In order to gain additional SAR information, a pure sample of 8 along with compounds 24–27 which vary at the $R_1$ position alone was prepared for study. Table 2 lists the $K_i$ values for these derivatives at the mu and kappa opioid receptors along with the $K_i$ values for the mu-selective reference compound 5a, naltrexone, and the kappa-selective antagonist nor-BNI. The delta receptor assay was not performed for compounds 24–27 as all previous derivatives of 8 had shown no affinity for this receptor subtype. This study revealed that 8 not only actively binds the kappa receptor ($K_i$=6.9 nM) but also possessed a 57-fold selectivity for the kappa vs. the mu receptor ($K_i$=393 nM) and >870-fold selectivity for the kappa vs. the delta receptor ($K_i$>5700 nM). Compound 8 thus displays a high degree of opioid kappa receptor subtype selectivity.[1,2] Nor-BNI (1) has a higher affinity for the kappa receptor than 8 and has a greater kappa selectivity relative to the mu receptor. However, 8 is more selective for the kappa receptor relative to the delta receptor. A part of these differences could be due to the use of different tissues and radioligands.

The data for the beta isobutyl substituent compound 24, which results formally from insertion of a methylene between the isopropyl group and its adjacent stereogenic center of compound 8, displays a loss of affinity for the kappa receptor while maintaining the same affinity for the mu receptor as compound 8. The net effect is a loss of selectivity between the mu and kappa receptor subtypes. Compound 26 ($R_1$=cyclohexyl) shows a similar loss of affinity for the kappa receptor with a gain in affinity for the mu receptor resulting in a similar loss of selectivity. Compound 25 with an $R_1$ sec-butyl group shows a slight decrease in both kappa and mu potency but retains selectivity, though its magnitude is lower relative to 8. Compound 27 ($R_1$= benzyl) displayed a binding profile completely different from that seen in 8 with a tremendous increase in mu potency and concomitant loss of kappa potency. This was not unexpected since compound 27, prepared from the amino acid phenylalanine, possesses an N-substituent with a phenyl ring separated from the piperidine ring by three methylene groups which are known to favor mu binding.[1,2] It was for this reason that phenylalanine was excluded from use in the library synthesis. Overall, the behaviors of the various $R_1$ derivatives of 8 indicate that the size of the lipophilic group in position $R_1$ is important to both the potency and receptor subtype selectivity of the ligand. Furthermore, the data supports the hypothesis that the isopropyl group in 8 is not simply biasing the conformation of side-chain but is instead interacting with the receptor directly in a ligand stabilizing interaction.

Figure 7:
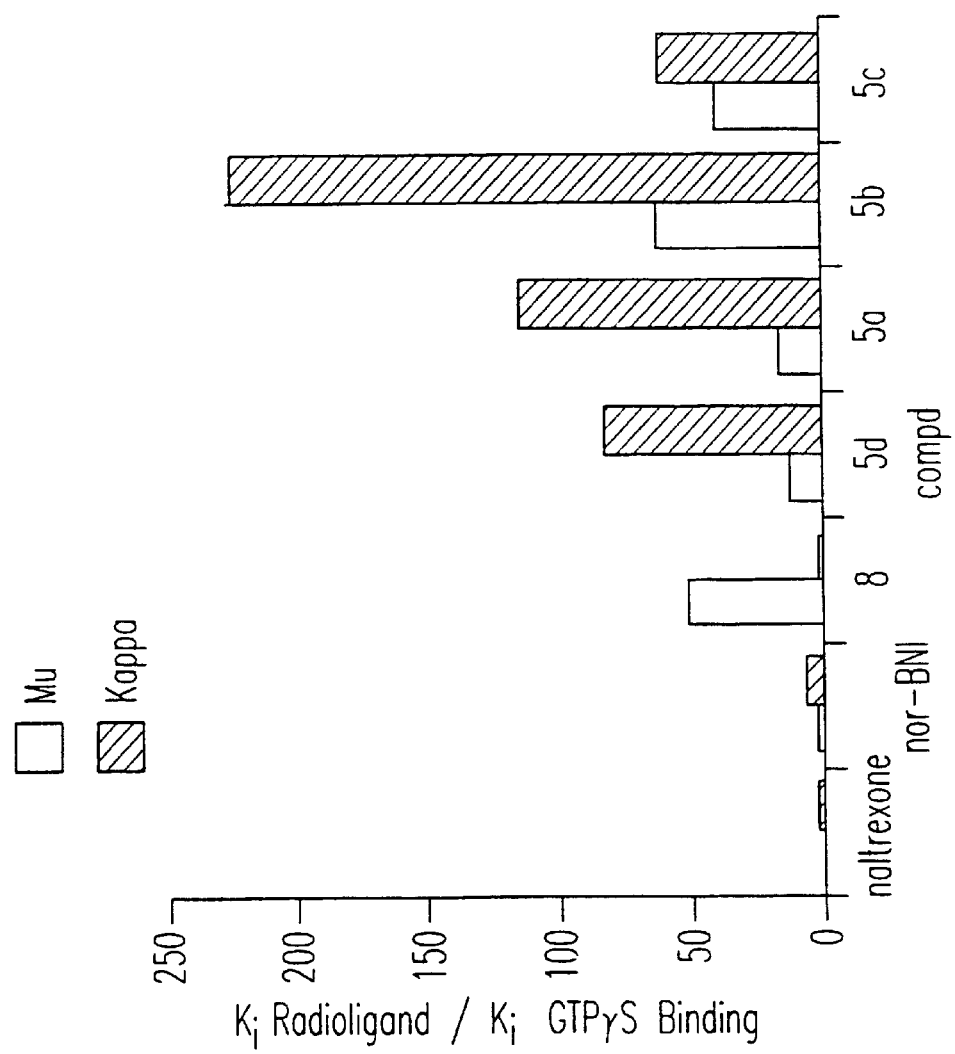
FIG. 7: Comparison of ratios of radioligand binding and GTPγS assays for compound 8, naltrexone, nor-BNI, 5d, and 5a–c described in Example 1, the N-trans-cinnamyl derivatives of 4b. The radioligand and GTPγS binding data for 5a–d were taken from ref. 9 cited in Example 1.

The agonist/antagonist activity of compound 8 was measured by determining its ability to either stimulate or reverse opioid agonist stimulated binding of the nonhydrolyzable GTP analog, [$^{35}$S]GTPγS, in all three opioid receptor assays (Table 3).[3] Table 3 includes data obtained for naltrexone, the standard nonselective opioid pure antagonist, nor-BNI, the prototypical kappa-selective antagonist, and the potent, mu-favoring opioid antagonist (5a). The kappa selectivity displayed by compound 8 in the inhibition of radioligand binding assay was not observed in the [$^{35}$S]GTPγS functional assay. This is not an atypical situation; radioligand binding results often differ substantially from those seen in functional assays but this typically involves agonists. The antagonists, naltrexone, normally display $K_i$ (radioligand)/ $K_i$ (GTPγS) binding ratios near unity whereas ratios greater than unity have been observed for antagonists of the N-substituted trans-3,4-dimethyl-4-(3-hydroxyphenyl) piperidine series.[1] This phenomenon is illustrated graphically in FIG. 7. The trans-cinnamyl derivatives 5a–c and compound 5d display $K_i$ (radioligand)/$K_i$ (GTPγS) binding ratios greater than unity in the mu and kappa receptor assays which is distinctly different from the response demonstrated by naltrexone. In the present case compound 8 is found to behave like naltrexone in the kappa receptor assays with a ratio near unity which is far different from the behavior seen for 5a–c and 5d, which show ratios of 118, 228, 63, and 85, respectively. In the mu receptor assay on the other hand, compound 8 with a ratio of 54 behaves like 5a–c and 5d which give ratios of 19, 66, 43, and 15. This differential response of 8 in the [$^{35}$S]GTPγS assay is sufficiently large so as to erode the kappa receptor selectivity observed for 8 in the radioligand binding assays. Note that the $K_i$ (radioligand)/$K_i$ (GTP) binding ratios for nor-BNI at the mu and kappa receptor are 2.8 and 7.36, respectively.

Conclusions

The identification of compound 8, which displays a highly selective kappa vs. mu receptor inhibition of radioligand binding profile and a potent mu/kappa opioid antagonist profile, demonstrates the effectiveness of the biased library approach to lead compound generation. Since both the mu and kappa receptors may be important in heroin abuse, compound 8 should be useful as a treatment medication for heroin abuse.

Experimental Section

Melting points were determined on a Thomas-Hoover capillary tube apparatus and are not corrected. Elemental analyses were obtained by Atlantic Microlabs, Inc. and are within ±0.4% of the calculated values. All optical rotations were determined at the sodium D line using a Rudolph Research Autopol III polarimeter (1-dm cell). $^1$H NMR spectra were determined on a Bruker WM-250 spectrometer using tetramethylsilane as an internal standard. Silica gel 60

(230–400 mesh) was used for all column chromatography. Mass spectral data was obtained using a Finnegan LCQ electrospray mass spectrometer in positive ion mode at atmospheric pressure. All reactions were followed by thin-layer chromatography using Whatman silica gel 60 TLC plates and were visualized by UV, charring using 5% phosphomolybdic acid in ethanol and/or exposure to iodine vapor. All solvents were reagent grade. Tetrahydrofuran and diethyl ether were dried over sodium benzophenone ketyl and distilled prior to use. Methylene chloride was distilled from calcium hydride prior to use.

General Method for the Introduction of Diversity Elements $R_1$ and $R_2$ into Structure 6. (+)-(3R,4R)-Dimethyl-4-(3-hydroxyphenyl)piperidine (4b) (11.5 mmol), the appropriate Boc-protected amino acid (11.5 mmol) and BOP reagent (11.5 mmol) were combined in THF (150 mL) at room temperature, and to this was immediately added triethylamine (TEA) or diisopropylethylamine (25.3 mmol). After stirring for 1 h, the reaction mixture was poured into ethyl ether (500 mL) and water (150 mL) in a separatory funnel. The mixture was shaken and the aqueous layer removed. This procedure was repeated using 150 mL saturated $NaHCO_3$ and 150 mL brine. The organic layer was diluted with hexane until cloudy and dried ($Na_2SO_4$), concentrated under reduced pressure, then dissolved in 100 mL chloroform (stored over $K_2CO_3$), and concentrated again. This was placed on a high vacuum system to remove residual solvent yielding a foamy yellow/white solid.

After remaining under vacuum on the pump overnight, this unpurified material was dissolved in methylene chloride 45 mL and cooled to −20° C. (methanol/ice). To this was added neat trifluoroacetic acid in 10-mL portions over 2 min to give a total addition of 30 mL. The entire mixture was stirred for exactly 30 min and then the cooling bath was removed for exactly 30 min. At this point, the reaction mixture was poured into a 1 L beaker containing a large stir bar and a rapidly agitated mixture of saturated bicarbonate solution (400 mL) and chloroform (150 mL). After completed addition, the pH of the mixture was verified to be 10 and adjusted with solid sodium bicarbonate if necessary. This mixture was poured into a separatory funnel. Any precipitated organic compounds were rinsed into the separatory funnel using a small amount of methanol. The beaker was then rinsed with a small amount of water which was added to the separatory funnel. The layers were agitated, separated, and the aqueous layer extracted five additional times using 3:1 methylene chloride:THF. It was observed that compounds with small groups $R_1$ required additional extractions and/or sodium chloride saturation of the aqueous layer. The combined organic layers were dried over sodium sulfate and the solvent removed at reduced pressure. The material was then placed on a high vacuum pump to yield a yellow foamy solid.

Unpurified material from the deprotection step was dissolved in THF (150 mL) and cooled to −20° C. (methanol/ice). To this stirred mixture was added a solution of borane dimethylsulfide complex, 2M in THF (110 mmol) dropwise. The solution was then heated to reflux and held for 3 h after which time, the solution was cooled to −20° C.; and to this was carefully added methanol (72 mL) dropwise. This mixture was stirred for 1 h at room temperature, 16.4 mL of 1M HCl in ethyl ether was added, the solution was allowed to stir for 30 min, and the solvents removed on a rotary evaporator. The resulting residue was partitioned between 3:1 methylene chloride:tetrahydofuran and water, the pH was adjusted to 10 with saturated sodium bicarbonate, and the aqueous layer was saturated with sodium chloride and extracted several times with 3:1 methylene chloride:tetrahydofuran. The combined organic layers were dried over sodium sulfate and the solvent removed. This material was purified by flash chromatography on a silica gel column which was prepared by slurry packing with chloroform. The impure compounds were loaded on the column as a chloroform solution. Elution proceeded with neat chloroform followed by 3% methanol up to 10% methanol in chloroform as needed to elute the desired compounds. Product fractions were combined and the solvent was removed on a rotary evaporator. This material was dissolved in a minimum of hot ethyl acetate and allowed to crystallize. Crystalline material was isolated by filtration followed by washing with a small amount of ice-cold ethyl acetate and used directly in the next step after drying overnight in a vacuum oven.

Introduction of Diversity Element $R_3$ into Structure 7. The appropriate pure diamine 6, produced in the previous step (0.05 mmol×the number of derivatives being prepared), was dissolved in THF (2 mL×the number of derivatives being prepared) and to this was added TEA (0.1 mmol×the number of derivatives being prepared). Then, into prelabeled, 20-mL scintillation vials containing a stir bar was added one of the chosen carboxylic acids (0.05 mmol). To this was added the appropriate fraction of the diamine/TEA/THF mixture followed by 50 µL of a 1M solution of BOP reagent in dimethylformamide (DMF). The vial was then capped with a telfon-lined lid and stirred for 1 h at room temperature. After this time, 4 mL of ethyl ether and 2 mL of water were added to the vial. After shaking and allowing the layers to settle, the aqueous layer was withdrawn with a pipette. Next, 2 mL of saturated sodium bicarbonate solution was added and the procedure repeated. This was followed by a similar wash with saturated sodium chloride solution. Sodium sulfate was added to the vial, and after drying, the mixture was pipetted into a preweighed, prelabeled 20-mL scintillation vial via a 6-in Pasteur pipette containing a small cotton plug. Following this, 2 mL of chloroform was added to the drying agent and the vial shaken after which the chloroform rinse was filtered as above. The collecting vials were placed under a nitrogen outlet and allowed to evaporate. Once the solvent was removed, the vials were placed in a high vacuum desiccator and allowed to remain overnight. The vials were reweighed, and the crude yield determined by difference. Since pilot studies showed that the BOP-coupling reaction produced very clean samples, the products were used without further purification, and the purity was taken to be 100%.

Prior to screening, all compounds were diluted to a concentration of 10 mM in dimethylsulfoxide (DMSO). Dilution was accomplished by determining the mean mmol/vial for each batch of 20 reactions using an Excel 3.0 spreadsheet. Weights deviating from the mean by >±10% were grouped into a second and third set above and below the mean. These were also averaged within the same parameters. Any compounds not falling within the above sets were diluted individually according to their weight. This procedure permitted sample dilution to be accomplished using a minimum number of different volume deliveries of DMSO. Once diluted to 10 mM, 1-mL samples from each vial were withdrawn and placed in rows A and E (one compound/well) of a 1 mL×96-well polypropylene microtiter plate. Serial dilution was then performed using Matrix multichannel pipettors which provided a 1-mM solution in rows B and F and a 0.1-mM solution in rows C and G. Once all of the compounds were transferred to plates and diluted to the proper concentration, the plates were placed in the refrigerator prior to assay.

N-(2'-Aminoethyl)-(3R,4R)-dimethyl-4-(3-hydroxyphenyl)piperidine (6a). Prepared from N-(tert-butoxy)-glycine and (+)-(3R,4R)-dimethyl-4-(3-hydroxyphenyl)piperidine according to the general procedure in 15% yield: $^1$H NMR (MeOH-d4) δ 7.13–7.062 (t, 1H, J=8.1 Hz), 6.77–6.74 (m, 2H), 6.59–6.55 (m, 1H), 3.31–3.29 (m, 1H), 2.83–2.70 (m, 3H), 2.5 (d, 2H, J=3.1 Hz), 2.46–2.27 (m, 3H), 2.00 (s, 1H), 1.6 (d, 2H, J=3.1 Hz), 1.68 (d, 1H, J=13.7 Hz), 1.29 (s, 3H), 0.89 (d, 3H, J=7.0 Hz); $^{13}$C NMR (MeOH-d4) δ 158.5, 152.9, 130.0, 117.9, 113.9, 113.3, 61.6, 57.1, 51.5, 40.2, 39.5, 39.1, 32.0, 28.2, 16.7. MS (electrospray) M+1=249. Calculated=249.

N-(2'-Methylaminoethyl)-(3R,4R)-dimethyl-4-(3-hydroxyphenyl)piperidine (6b). Prepared from N-(tert-butoxy)-sarcosine and (+)-(3R,4R)-dimethyl-4-(3-hydroxyphenyl)piperidine according to the general procedure in 32% yield: $^1$H NMR (MeOH-d4) δ 7.9 (t, 1H, J=7.7 Hz), 6.77 (d, 1H), 6.74 (s, 1H), 6.58 (d, 1H), 2.95–2.90 (m, 1H), 2.87–2.82 (m, 2H), 2.66 (dd, 1H), 2.61–2.55 (m, 2H), 2.54 (s, 3H), 2.52 (td, 1H), 2.37 (td, 1H), 2.03–2.00 (m, 1H), 1.69 (brd, 1H), 1.30 (s, 3H), 0.89 (d, 3H, J=7.0 Hz); $^{13}$C NMR (MeOH-d4) δ 130.0, 118.0, 113.8, 113.3, 57.4, 56.7, 51.1, 48.2, 40.2, 39.4, 35.0, 31.9, 28.1, 16.6. MS (electrospray) M+1=263. Calculated=263.

N-[(2'S)-Aminopropyl]-(3R,4R)-dimethyl-4-(3-hydroxyphenyl)piperidine (6c). Prepared from N-(tert-butoxy)-L-alanine and (+)-(3R,4R)-dimethyl-4-(3-hydroxyphenyl)piperidine according to the general procedure in 56% yield: $^1$H NMR (MeOH-d4) δ 7.11–7.08 (t, 1H, J=7.7), 6.78–6.76 (d, 1H), 6.74 (s, 1H), 6.59–6.57 (d, 1H), 2.953–2.902 (m, 1H), 2.874–2.826 (m, 2H), 2.676–2.647 (dd, 1H), 2.618–2.559 (m, 2H), 2.548 (s, 3H), 2.541–2.400 (td, 1H), 2.342–2.284 (td, 1H), 2.030–2.002 (m, 1H), 1.613–1.587 (brd, 1H), 1.303 (s, 3H), 0.800–0.786 (d, 3H, J=7.0); $^{13}$C NMR (MeOH-d4) d 130.0, 118.0, 113.8, 113.3, 57.4, 56.7, 51.1, 48.2, 40.2, 39.4, 35.0, 31.9, 28.1, 16.6. MS (electrospray) M+1=263. Calculated=263.

N-[(2'S)-(Methylamino)propyl]-(3R,4R)-dimethyl-4-(3-hydroxyphenyl)piperidine (6d). Prepared from N-(tert-butoxy)-N-methyl-L-alanine[17] and (+)-(3R,4R)-dimethyl-4-(3-hydroxyphenyl)piperidine according to the general procedure in 33% yield: $^1$H NMR (MeOH-d4) δ 7.18 (t, 1H, J=7.9 Hz), 6.76 (d, 1H), 6.73 (s, 1H), 6.57 (d, 1H), 2.72–2.64 (m, 2H), 2.61–2.47 (m, 3H), 2.36 (s, 3H), 2.34–2.20 (m, 3H), 2.00–1.99 (m, 1H), 1.56 (dd, 1H), 1.29 (s, 3H), 1.03 (d, 3H, J=6.2 Hz), 0.65 (d, 3H, J=6.9 Hz); $^{13}$C NMR (MeOH-d4) δ 158.4, 153.3, 130.1, 117.9, 113.7, 113.3, 65.1, 56.0, 52.9, 52.9, 40.0, 39.5, 33.7, 31.9, 28.0, 17.3, 16.7. MS (electrospray) M+1=277. Calculated=277.

N-[(2'S)-Amino-3'-methylbutyl]-(3R,4R)-dimethyl-4-(3-hydroxyphenyl)piperidine (6e). Prepared from N-(tert-butoxy)-L-valine and (+)-(3R,4R)-dimethyl-4-(3-hydroxyphenyl)piperidine according to the general procedure in 78% yield: $^1$H NMR (MeOH-d4) δ 7.126–7.062 (t, 1H), 6.769–6.735 (m, 2H), 6.603–6.558 (m, 1H), 2.657–2.179 (m, 8H), 2.000 (brs, 1H), 1.583–1.502 (m, 2H), 1.294 (s, 3H), 0.978–0.912 (q, 6H), 0.789–0.761 (d, 3H); $^{13}$C NMR (MeOH-d4) δ 158.5, 153.3, 130.1, 117.8, 113.8, 113.3, 63.4, 55.8, 54.1, 53.3, 40.0, 39.5, 33.1, 31.9, 28.1, 19.6, 19.2, 16.8. MS (electrospray) M+1=291. Calculated=291.

N-[(2'R)-Amino-3'-methylbutyl]-(3R,4R)-dimethyl-4-(3-hydroxyphenyl)piperidine (6f). Prepared from N-(tert-butoxy)-D-valine and (+)-(3R,4R)-dimethyl-4-(3-hydroxyphenyl)piperidine according to the general procedure in 62% yield: $^1$H NMR (MeOH-d4) δ 7.11–7.08 (t, 1H), 6.78–6.76 (d, 1H), 6.74 (s, 1H), 6.59–6.57 (dd, 1H), 3.139–3.097 (m, 1H), 2.953 (brs, 1H), 2.894–2.865 (dd, 1H), 2.546–2.500 (m, 2H), 2.401–2.292 (m, 3H), 2.046–2.034 (brm, 1H), 1.894–1.827 (sext, 1H), 1.62–1.30 (m, 1H), 1.311 (s, 3H), 1.042–1.006 (dd, 6H), 0.834–0.820 (d, 3H); $^{13}$C NMR (MeOH-d4) δ 152.9, 130.1, 118.0, 113.8, 113.3, 59.8, 58.8, 55.2, 50.0, 40.4, 39.4, 31.6, 31.1, 28.0, 18.8, 18.5, 16.5. MS (electrospray) M+1=291. Calculated=291.

N-[(2'S)-Amino-4'-methylpentyl]-(3R,4R)-dimethyl-4-(3-hydroxyphenyl)piperidine (6g). Prepared from N-(tert-butoxy)-L-leucine and (+)-(3R,4R)-dimethyl-4-(3-hydroxyphenyl)piperidine according to the general procedure in 56% yield: $^1$H NMR (MeOH-d4) δ 7.09 (t, 1H, J=7.9 Hz), 6.76 (d, 1H, J=7.9 Hz), 6.73 (s, 1H), 6.57 (dd, 1H, J=2.2, 7.9 Hz), 3.03–2.97 (m, 1H), 2.73 (d, 1H, J=11.2 Hz), 2.64 (d, 1H, J=11.1 Hz), 2.56 (td, 1H, J=2.5, 12.0 Hz), 2.48 (dd, 1H, J=2.7, 11.4 Hz), 2.33 (td, 1H, J=4.5, 12.7 Hz), 2.25 (dd, 1H, J=3.6, 12.4 Hz), 2.19–2.15 (m, 1H), 2.01–2.00 (m, 1H), 1.75 (sept, 1H, J=6.6 Hz), 1.56 (d, 1H, J=13.0 Hz), 1.29 (s, 3H), 1.27–1.15 (m, 2H), 0.94–0.91 (m, 6H), 0.07 (d, 3H, J=7.0 Hz); $^{13}$C NMR (MeOH-d4) δ 158.3, 153.3, 130.1, 117.9, 113.7, 113.2, 65.7, 56.0, 53.1, 46.5, 45.2, 40.0, 39.5, 31.9, 28.0, 25.8, 23.7, 22.6, 16.7. MS (electrospray) M+1=305. Calculated=305.

N-[(2'S)-Amino-3'-methylpentyl]-(3R,4R)-dimethyl-4(3-hydroxyphenyl)piperidine (6h). Prepared from N-(tert-butoxy)-L-isoleucine and (+)-(3R,4R)-dimethyl-4-(3-hydroxyphenyl)piperidine according to the general procedure in 47% yield: $^1$H NMR (MeOH-d4) δ 7.19 (t, 1H, J=7.9 Hz), 6.76 (d, 1H, J=8.1 Hz), 6.73–6.73 (m, 1H), 6.58–6.56 (dd, 1H, J=2.1, 7.9 Hz), 2.86–2.82 (m, 1H), 2.75–2.73 (m, 1H), 2.65–2.57 (m, 2H), 2.502–2.474 (dd, 1H, J=2.8, 11.4 Hz), 2.40–2.23 (m, 3H), 2.02–2.00 (m, 1H), 1.59–1.50 (m, 2H), 1.46–1.41 (m, 1H), 1.30 (s, 3H), 1.24–1.17 (m, 1H), 0.98–0.87 (m, 6H), 0.78 (d, 3H, J=7.0 Hz); $^{13}$C NMR (MeOH-d4) δ 158.3, 153.2, 130.1, 117.9, 113.7, 113.3, 61.9, 55.9, 53.1, 52.9, 49.0, 40.0, 39.5, 39.3, 31.9, 28.0, 26.6, 16.7, 15.1, 11.8. MS (electrospray) M+1=305. Calculated=305.

N-[(2'S)-Amino-2'-cyclohexylethyl]-(3R,4R)-dimethyl-4-(3-hydroxyphenyl)piperidine (6i). Prepared from N-(tert-butoxy)-L-cyclohexylglycine and (+)-(3R,4R)-dimethyl-4-(3-hydroxyphenyl)piperidine according to the general procedure in 63% yield: $^1$H NMR (MeOH-d4) δ 7.18 (t, 1H, J=7.9), 6.76 (d, 1H, J=7.8 Hz), 6.75 (s, 1H), 6.57 (d, 1H, J=7.8 Hz), 2.74–2.70 (m, 2H), 2.63–2.55 (m, 2H), 2.47–2.45 (d, 1H, J=10.0 Hz), 2.48 (dd, 1H, J=2.9, 12.4 Hz), 2.36 (td, 1H, J=4.3, 12.6 Hz), 2.23 (t, 1H, J=11.6 Hz), 2.00 (m, 1H), 1.76–1.74 (m, 3H), 1.67 (d, 2H, J=11.9 Hz), 1.57 (d, 1H, J=13.0 Hz), 1.39–1.16 (m, 7H), 1.09 (quint, 2H, J=12.4 Hz), 0.77 (d, 3H, J=6.8 Hz); $^{13}$C NMR (MeOH-d4) δ 158.3, 153.3, 130.1, 117.9, 113.7, 113.3, 162.6, 55.8, 53.4, 53.1, 42.9, 40.0, 39.5, 31.9, 30.9, 30.5, 30.2, 28.0, 27.6, 27.4, 16.7. MS (electrospray) M+1=331. Calculated=331.

N-[(2'S)-Methylamino-2'-phenylethyl]-(3R,4R)-dimethyl-4-(3-hydroxyphenyl)-piperidine (6j). Prepared from N-(tert-butoxy)-N-methyl-phenylglycine and (+)-(3R,4R)-dimethyl-4-(3-hydroxyphenyl)piperidine according to the general procedure in 44% yield: $^1$H NMR (MeOH-d4) δ 7.34–7.22 (m, 5H), 7.13 (t, 1H, J=8.2 Hz), 6.80–6.77 (m, 2H), 6.61–6.69 (m, 1H), 3.63 (dd, 1H, J=3.7, 12.6 Hz), 2.73 (brd, 2H, J=7.6 Hz), 2.64–2.52 (m, 3H), 2.38 (dd, 2H, J=3.6, 12.6 Hz), 2.25 (s, 3H), 2.04 (brd, 1H, J=6.3 Hz), 1.59 (d, 1H, J=12.9), 1.312 (s, 3H), 0.818–0.790 (d, 3H, J=6.9); $^{13}$C NMR (MeOH-d4) δ 147.3, 142.5, 131.5, 119.5, 119.0, 118.0, 107.4, 103.2, 102.7, 68.7, 68.233, 67.7, 55.2, 52.9, 45.1, 42.5, 42.5, 29.2, 28.9, 24.2, 21.3, 17.7. MS (electrospray) M+1=339. Calculated=339.

N-[(2'S)-Amino-3'-phenylpropyl]-(3R,4R)-dimethyl-4-(3-hydroxyphenyl)piperidine (6k). Prepared from N-(tert-butoxy)-L-phenylalanine and (+)-(3R,4R)-dimethyl-4-(3-hydroxyphenyl)piperidine according to the general procedure in 44% yield: $^1$H NMR (MeOH-d4) δ 7.29 (t, 1H, J=7.4 Hz), 7.24–7.06 (m, 5H), 6.75–6.71 (m, 2H), 6.57–6.55 (m, 1H), 3.86–3.84 (m, 5H), 3.22–3.94 (m, 1H), 2.83–2.69 (m, 2H), 2.63–2.39 (m, 5H), 2.35–2.24 (m, 2H), 1.97 (t, 1H, J=6.4 Hz), 1.54 (t, 1H, J=12.7 Hz), 1.27 (s, 3H), 0.74 (dd, 3H, J=6.95, 21.04 Hz); $^{13}$C NMR (MeOH-d4) δ 158.3, 153.3, 139.9, 130.6, 130.3, 130.0, 129.6, 129.2, 127.5, 127.1, 118.0, 117.9, 113.8, 113.7, 113.2, 65.0, 64.7, 61.0, 57.3, 56.1, 52.9, 52.1, 50.5, 49.5, 49.3, 49.2, 49.0, 48.8, 48.7, 48.5, 41.9, 41.5, 40.3, 40.0, 39.4, 31.9, 28.0, 16.7. MS (electrospray) M+1=339. Calculated=339.

N-{(2'S)-[3-(4-Hydroxyphenyl)propanamido]-3'-methylbutyl}-(3R,4R)-dimethyl-4-(3-hydroxyphenyl)piperidine (8). Prepared from compound 6e and 3-(4-hydroxyphenyl)propionic acid according to the general procedure above in 74% yield and purified by silica gel chromatography. The hydrochloride salt was prepared using 1M HCl in ethyl ether/methanol and precipitated from ethyl acetate: mp 136–140° C.; $^1$H NMR (free base). CD3OD δ 7.16 (t, J=7.94, Hz, 1H), 7.04 (d, J=8.45 Hz, 2H), 6.76 (d, J=7.78 Hz, 1H), 6.72–6.69 (m, 2H), 6.65 (dd, J=8.04, 1.76 Hz, 1H), 4.02–3.98 (m, 1H), 3.57 (d, J=12.5 Hz, 1H), 3.40 (ddd, J=2.90, 11.6, 13.4 Hz, 2H), 3.03 (dd, J=10.5, 13.4 Hz, 1 Hz), 2.84 (t, 7.07 Hz, 2H), 2.60 (t, 7.58 Hz, 2H), 2.43 (dt, J=13.21, 4.9 Hz, 1H), 2.36–2.35 (m, 1H), 1.85 (d, J=14.5 Hz, 1H), 1.87–1.76 (m, 1H), 1.42 (s, 3H), 0.92 (t, J=6.98 Hz, 6H), 0.815 (d, J=7.53, 3H); $^{13}$C NMR, CD3OD δ 176.3, 159., 157.7, 153.8, 133.8, 131.3, 131.0, 118.9, 117.1, 114.6, 114.2, 62.0, 57.2, 53.2, 52.8, 40.9, 40.3, 33.1, 33.1, 32.5, 31.7, 28.8, 20.6, 18.9, 17.3. MS (electrospray) M+1=439. Anal. (C$_{27}$H$_{39}$ClN$_2$O$_3$.1.5H$_2$O): C, H, N.

Compounds cited in Table 1 were removed from the library and purified by silica gel chromatography. The purity of the library sample was determined according to the formula [(mg isolated sample/mg crude mass sample)×100].

N-{(2'R)-[3-(4-Hydroxyphenyl)propanamido]-3'-methylbutyl}-(3R,4R)-dimethyl-4-(3-hydroxyphenyl)piperidine (9). Prepared from compound 6f and 3-(4-hydroxyphenyl)propionic acid according to the general procedure. Purity (85%); $^1$H NMR (MeOH-d4) δ 7.83 (s, 3H), 7.13–7.00 (m, 3H), 6.77–6.67 (m, 4H), 6.61–6.57 (m, 1H), 3.96–3.89 (m, 1H), 2.86–2.78 (m, 3H), 2.62–2.58 (m, 1H), 2.48 (d, 3H, J=8.0 Hz), 2.36–2.14 (m, 4H), 1.94 (brd, 1H, J=6.3 Hz), 1.76 (sept, 1H, J=5.5 Hz), 1.51 (brd, 1H, J=11.0 Hz), 1.26 (s, 3H), 0.84–0.74 (m, 9H). MS (electrospray) M+1=439. Calculated=439.

N-{(2'S)-[(3-Phenylpropanamido)-3'-methyl]butyl}-(3R,4R)-dimethyl-4-(3-hydroxyphenyl)piperidine (10). Prepared from compound 6e and 3-phenylpropionic acid according to the general procedure. Purity (87%); $^1$H NMR (MeOH-d4) δ 7.25–7.22 (m, 2H), 7.17–7.13 (m, 4H), 6.82 (s, 1H), 6.76 (d, 1H, J=7.8 Hz), 6.70–6.68 (m, 1H), 5.74 (s, 1H), 4.02–3.97 (m, 1H), 2.99–2.87 (m, 2H), 2.74–2.69 (m, 1H), 2.64 (brd, 1H, J=1.3 Hz), 2.57–2.40 (m, 6H), 2.27–2.21 (m, 2H), 2.17 (s, 3H), 1.92–1.87 (m, 2H), 1.56 (d, 1H, J=13.0 Hz), 1.28 (s, 3H), 0.81 (t, 6H, J=6.8 Hz), 0.69 (d, 3H, J=6.8 Hz). MS (electrospray) M+1=423. Calculated=423.

N-{(2'S)-[3-(3-Hydroxyphenyl)propanamido]-3'-methylbutyl}-(3R,4R)-dimethyl-4-(3-hydroxyphenyl)piperidine (11). Prepared from compound 6e and 3-(3-hydroxyphenyl)propionic acid according to the general procedure. Purity (84%); $^1$H NMR (MeOH-d4) δ 7.24–7.23 (m, 1H), 7.13–7.03 (m, 3H), 6.76–6.57 (m, 5H), 3.32–3.29 (m, 4H), 2.85–2.17 (m, 8H), 1.97 (brs, 1H), 1.75–1.73 (m, 1H), 1.57 (brd, 1H, J=12.3 Hz), 1.28 (s, 3H) 0.863 (t, 6H, J=6.5 Hz), 0.72 (d, 3H, J=7.0). MS (electrospray) M+1=439. Calculated=439.

N-{(2'S)-[3-(2-Hydroxyphenyl)propanamido]-3'-methylbutyl}-(3R,4R)-dimethyl-4-(3-hydroxyphenyl)piperidine (12). Prepared from compound 6e and 3-(2-hydroxyphenyl)propionic acid according to the general procedure. Purity (85%); $^1$H NMR (CDCl3-d) δ 7.04–6.82 (m, 3H), 6.66–6.65 (m, 2H), 6.48–6.39 (m, 3H), 3.97–3.94 (m, 1H), 2.87–2.84 (m, 2H), 2.76 (d, 1H, J=11 Hz), 2.56–2.22 (m, 8H), 1.94–1.93 (brm, 1H), 1.80 (sextet, 1H, J=6.9 Hz), 1.52 (d, 1H, J=13.3 Hz), 1.26 (s, 3H), 0.84 (dd, 6H, J=13.1 Hz), 0.75 (d, 3H, J=6.9 Hz). MS (electrospray) M+1=439. Calculated=439.

N-{(2'S)-[(4-Hydroxyphenyl)acetamido]-3'-methylbutyl}-(3R,4R)-dimethyl-4-(3-hydroxyphenyl)piperidine (13). Prepared from compound 6e and 4-hydroxyphenylacetic acid according to the general procedure. Purity (88%); $^1$H NMR (MeOH-d4) δ 7.14–7.06 (m, 3H), 6.67–6.69 (m, 4H), 6.58 (d, 1H, J=8.1 Hz), 3.95–3.92 (m, 1H), 3.32–3.30 (m, 1H), 2.70–2.60 (m, 1H), 2.56–2.47 (m, 1H), 2.41–2.15 (m, 6H), 1.90 (brs, 1H), 1.81–1.74 (m, 1H), 1.51 (d, 2H, J=12.5 Hz), 1.25 (s, 3H), 0.86 (t, 6H, J=6.7 Hz), 0.67 (d, 3H, J=6.9 Hz). MS (electrospray) M+1=425. Calculated=425.

N-{(2'S)-[trans-3-(4-Hydroxyphenyl)acrylamido]-3'-methylbutyl}-(3R,4R)-dimethyl-4-(3-hydroxyphenyl)piperidine (14). Prepared from compound 6e and trans-3-(4-hydroxyphenyl)cinnamic acid according to the general procedure. Purity (85%); $^1$H NMR (MeOH-d4) δ 7.25–7.37 (m, 3H), 7.11–7.04 (m, 1H), 6.79–6.72 (m, 4H), 6.56 (d, 1H, J=9.5 Hz), 6.47 (d, 1H, J=12.7 Hz), 4.10 (m, 1H), 2.80 (m, 1H), 2.64 (m, 1H), 2.54–2.26 (m, 5H), 1.95 (m, 2H), 1.56 (d, 1H, J=13.1), 1.28 (s, 3H), 0.94 (t, 6H, J=6.8 Hz), 0.70 (d, 3H, J=6.9). MS (electrospray) M+1=437. Calculated=437.

N-{(2'S)-[3-(4-Fluorophenyl)propanamido]-3'-methylbutyl}-(3R,4R)-dimethyl-4-(3-hydroxyphenyl)piperidine (15). Prepared from compound 6e and 3-(4-fluorophenyl)propionic acid according to the general procedure. Purity (89%); $^1$H NMR (MeOH-d4) δ 7.23–7.17 (m, 2H), 7.69 (t, 1H, J=8.0 Hz), 6.99–6.92 (m, 2H), 6.76–6.73 (m, 2H), 6.60–6.54 (m, 1H), 3.96–3.90 (m, 1H), 2.88 (t, 2H, J=7.7), 2.76 (d, 1H, J=10.3 Hz), 2.65–2.32 (m, 8H), 1.97 (brs, 1H), 1.73–1.69 (m, 1H), 1.54 (d, 1H, J=12.1 Hz), 1.27 (s, 3H), 0.80 (t, 6H, J=5.8 Hz), 0.71 (d, 3H, J=6.9 Hz). MS (electrospray) M+1=441. Calculated=441.

N-{(2'S)-[3-(3,4-Dihydroxyphenyl)propanamido]-3'-methylbutyl}-(3R,4R)-dimethyl-4-(3-hydroxyphenyl)piperidine (16). Prepared from compound 6e and 3-(3,4-dihydroxyphenyl)propionic acid according to the general procedure. Purity (78%); $^1$H NMR (MeOH-d4) δ 7.09 (t, 1H, J=7.9 Hz), 6.76–6.73 (m, 2H), 6.67–6.49 (m, 4H), 3.92 (brs, 1H), 2.74 (t, 3H, J=7.6 Hz), 2.63–2.59 (m, 1H), 2.51–2.15 (m, 7H), 1.94 (brs, 1H), 1.75–1.70 (m, 1H), 1.55 (d, 1H, J=12.1 Hz), 1.27 (s, 3H), 0.82 (t, 6H, J=6.4 Hz), 0.71 (d, 3H, J=6.9 Hz). MS (electrospray) M+1=455. Calculated=455.

N-{(2'S)-[3-(3-Methoxy-4-bydroxyphenyl)propanamido]-3'-methylbutyl}-(3R,4R)-dimethyl-4-(3-hydroxyphenyl)piperidine (17). Prepared from compound 6e and 3-(3-methoxy-4-hydroxyphenyl)propionic acid according to the general procedure. Purity (87%); $^1$H NMR (MeOH-d4) d 7.15 (t, 1H, J=7.7 Hz), 6.81–6.76 (m, 3H), 6.67 (d, 3H, J=3.3 Hz), 3.98 (brm, 1H), 3.80 (s, 3H), 2.86–2.69 (m, 3H), 2.53–2.22 (m, 8H), 1.89 (brs, 2H), 1.55 (d, 1H, J=12.0 Hz), 1.27 (s, 3H), 0.82 (dd, 6H, J=6.6, 3.2 Hz), 0.67 (d, 3H, J=6.9 Hz). MS (electrospray) M+1=469. Calculated=469.

N-{(2'S)-[3-(3-Methoxyphenyl)propanamido]-3'-methylbutyl}-(3R,4R)-dimethyl-4-(3-hydroxyphenyl)piperidine (18). Prepared from compound 6e and 3-(3-methoxyphenyl)propionic acid according to the general procedure. Purity (88%); $^1$H NMR (MeOH-d4) δ 7.30–7.12 (m, 4H), 6.9–6.8 (m, 4H), 3.95 (brs, 1H), 3.76 (s, 3H), 2.96 (d, 2H, J=6.8 Hz), 2.86–2.72 (m, 5H), 2.65–2.61 (m, 1H), 2.56–2.14 (m, 7H), 1.91(brs, 1H), 1.73–1.71 (m, 1H), 1.52 (d, 1H, J=13.0 Hz), 1.26 (s, 3H), 0.81 (t, 6H, J=6.7 Hz), 0.67 (d, 3H, J=6.9 Hz). MS (electrospray) M+1=453. Calculated=453.

N-{2'-[3-(4-Hydroxyphenyl)propanamido]ethyl}-(3R,4R)-dimethyl-4-(3-hydroxyphenyl)piperidine (19). Prepared from compound 6a and 3-(4-hydroxyphenyl)propionic acid according to the general procedure. Purity (82%); $^1$H NMR (MeOH-d4) δ 7.13–6.99 (m, 3H), 6.79–6.67 (m, 4H), 6.59 (dd, 1H, J=7.3, 1.8 Hz), 3.32–3.25 (m, 3H), 2.83–2.77 (m, 3H), 2.58 (s, 2H), 2.46–2.15 (m, 6H), 1.98 (brs, 1H), 1.58 (brd, 1H, J=12.8 Hz), 1.29 (s, 3H), 0.76 (d, 3H, J=7.0 Hz). MS (electrospray) M+1=397. Calculated=397.

N-{(2'S)-[3-(4-Hydroxyphenyl)propanamido]propyl}-(3R,4R)-dimethyl-4-(3-hydroxyphenyl)piperidine (20). Prepared from compound 6c and 3-(4-hydroxyphenyl)propionic acid according to the general procedure. Purity (88%); $^1$H NMR (MeOH-d4) δ 7.77 (s, 1H), 7.08 (t, 1H, J=8.1 Hz), 6.98 (d, 2H, J=8.4 Hz), 6.74–6.67 (m, 4H), 6.7 (d, 1H, J=7.5 Hz), 4.03 (dd, 1H, J=6.4 Hz), 2.81–2.70 (m, 3H), 2.49 (s, 2H), 2.44–2.26 (m, 4H), 2.16 (td, 2H, J=3.7, 10.9 Hz), 1.92–1.89 (m, 1H), 1.50 (d, 1H, J=12.3 (s, 3H), 1.04 (d, 3H, J=6.4 Hz), 0.71 (d, 3H, J=6.9 Hz). MS (electrospray) M+1=411. Calculated=411.

N-{2'-[3-(4-Hydroxyphenyl)-N-methylpropanamido]ethyl}-(3R,4R)-dimethyl-4-(3-hydroxyphenyl)piperidine (21). Prepared from compound 6b and 3-(4-hydroxyphenyl)propionic acid according to the general procedure. Purity (78%); $^1$H NMR (MeOH-d4) δ 7.84 (s, 1H), 7.18–7.00 (m, 3H), 6.77–6.69 (m, 4H), 6.60 (d, 1H, J=8.1 Hz), 3.47–3.27 (m, 2H), 2.92–2.90 (m, 3H), 2.82–2.77 (m, 3H), 2.67–2.54 (m, 3H), 2.47–2.18 (m, 3H), 1.96 (brs, 1H), 1.58–1.49 (m, 3H), 1.27 (d, 3H, J=2.91 Hz), 0.73 (t, 3H, J=6.5 Hz). MS (electrospray) M+1=411. Calculated=411.

N-{(2'S)-[3-(4-Hydroxyphenyl)-N-methylpropanamido]propyl}-(3R,4R)-dimethyl-4-(3-hydroxyphenyl)piperidine (22). Prepared from compound 6d and 3-(4-hydroxyphenyl)propionic acid according to the general procedure. Purity (89%); $^1$H NMR (MeOH-d4) δ 7.09 (t, 1H, J=7.9 Hz), 6.99 (d, 2H, J=8.2 Hz), 6.78–6.66 (m, 4H), 6.58–6.56 (m, 1H), 4.92–4.86 (m, 1H), 2.74 (s, 3H), 2.27–2.17 (m, 2H), 1.96–1.95 (brm, 1H), 1.55 (brd, 1H, J=14.3 Hz), 1.27 (s, 3H), 1.02 (d, 3H, J=6.7 Hz), 0.66 (d, 3H, J=6.9 Hz). MS (electrospray) M+1=425. Calculated=425.

N-{(2'S)-[3-(4-Hydroxyphenyl)-N-methylpropanamido]-2'-phenylethyl}-(3R,4R)-dimethyl-4-(3-hydroxyphenyl)piperidine (23). Prepared according to the general procedure using compound 6j and 3-(4-hydroxyphenyl)propionic acid according to the general procedure. Purity (86%); $^1$H NMR (MeOH-d4) δ 7.69–7.66 (m, 1H), 7.45–7.42 (m, 1H), 7.32–6.97 (m, 7H), 6.76 (d, 1H, J=9.4 Hz), 6.73 (s, 1H), 6.66–6.64 (m, 1H), 6.59–6.57 (m, 1H), 6.05 (q, 1H, J=5.5 Hz), 3.00–2.71 (m, 9H), 2.65–2.63 (m, 2H), 2.29. (td, 1H, J=4.3, 8.4 Hz), 2.01–2.00 (brm, 1H), 1.59 (brd, 1H, J=12.0 Hz), 1.32–1.28 (m, 6H), 0.71 (d, 3H, J=6.9 Hz). MS (electrospray) M+1=487. Calculated=487.

N-{(2'S)-[3-(4-Hydroxyphenyl)propanamido]-4'-methylpentyl}-(3R,4R)-dimethyl-4-(3-hydroxyphenyl)piperidine (24). Prepared according to the general coupling procedure (though on a 3-mmol scale) using compound 6g and 3-(4-hydroxyphenyl)propionic acid in 85% yield. Crude products were then purified by silica gel chromatography using 10–25% methanol in chloroform: $^1$H NMR (MeOH-d4) δ 7.85 (s, 1H), 7.26–7.06 (m, 6H), 6.97 (d, 2H, J=8.5 Hz), 6.76–6.66 (m, 3H), 6.58 (d, 1H, J=7.2 Hz), 4.27 (t, 1H, J=7.3 Hz), 2.84–2.23 (m, 10H), 1.93 (brd, 1H, J=7.2 Hz), 1.52 (d, 1H, J=12.0 Hz), 1.25 (s, 3H), 1.05 (t, 1H, J=7.2 Hz), 0.74 (d, 3H, J=6.9 Hz); $^{13}$C NMR (MeOH-d4) δ 164.0, 147.5, 143.0, 142.6, 129.0, 122.3, 119.9, 119.6, 119.3, 118.5, 116.5, 107.3, 105.5, 103.0, 102.2, 51.6, 46.1, 40.8, 29.4, 29.3, 29.3, 28.7, 21.4, 21.0, 17.3. Anal. ($C_{28}H_{40}N_2O_3$): C, H, N.

N-{(2'S)-[3-(4-Hydroxyphenyl)propanamido]-3'-methylpentyl}-(3R,4R)-dimethyl-4-(3-hydroxyphenyl)piperidine (25). Prepared according to the general procedure (though on a 3-mmol scale) using compound 6h and 3-(4-hydroxyphenyl)propionic acid in 81% yield. Crude products were then purified by silica gel chromatography using 10–25% methanol in chloroform: $^1$H NMR (MeOH-d4) δ 7.59 (s, 1H), 6.90–6.76 (m, 3H), 6.52–6.45 (m, 3H), 6.36 (d, 1H, J=7.6 Hz), 3.89 (brs, 1H), 2.56–2.54 (m, 3H), 2.39–1.95 (m, 9H), 1.70 (brs, 1H), 1.32–1.10 (m, 3H), 1.03 (s, 5H), 0.65–0.61 (m, 8H), 0.52–0.42 (m, 3H); $^{13}$C NMR (MeOH-d4) δ 163.8, 147.5, 146.0, 142.6, 122.2, 119.7, 119.4, 107.4, 105.5, 103.1, 102.6, 68.7, 53.7, 46.2, 41.0, 39.4, 39.1, 35.4, 33.4, 29.5, 28.9, 28.7, 21.5, 21.2, 17.5, 15.1, 13.3, 11.9. Anal. ($C_{28}H_{40}N_2O_3$): C, H, N.

N-{(2'S)-[3-(4-Hydroxyphenyl)propanamido]-2'-cyclohexylethyl}-(3R,4R)-dimethyl-4-(3-hydroxyphenyl)piperidine (26). Prepared according to the general procedure (though on a 3-mmol scale) using compound 6i and 3-(4-hydroxyphenyl)propionic acid in 87% yield. Crude products were then purified by silica gel chromatography using 10–25% methanol in chloroform: $^1$H NMR (MeOH-d4) δ 7.85–7.82 (m, 2H), 7.11–6.97 (m, 3H), 6.74–6.56 (m, 5H), 3.99–3.97 (m, 1H), 2.81–2.75 (m, 3H), 2.54 (m, 1H), 2.44–2.12 (m, 7H), 1.94 (brs, 1H), 1.54–1.26 (m, 3H), 1.25 (s, 3H), 1.02–0.68 (m, 10H); $^{13}$C NMR (MeOH-d4) δ 164.1, 147.5, 146.0, 142.6, 122.2, 119.7, 119.4, 107.3, 105.5, 103.1, 102.5, 68.7, 49.4, 45.5, 41.3, 40.9, 29.4, 28.8, 28.4, 21.5, 21.1, 17.4, 15.4. Anal. ($C_{30}H_{24}N_2O_3$): C, H, N.

N-{(2'S)-[3-(4-Hydroxyphenyl)propanamido]-3'-phenylpropyl}-(3R,4R)-dimethyl-4-(3-hydroxyphenyl)piperidine (27). Prepared according to the general procedure (though on a 3-mmol scale)using compound 6k and 3-(4-hydroxyphenyl)propionic acid in 82% yield. Crude products were then purified by silica gel chromatography using 10–25% methanol in chloroform: $^1$H NMR (MeOH-d4) δ 7.88(s, 1H), 7.12–7.00 (m, 3H), 6.76–6.66 (m, 4H), 6.59–6.55 (m, 1H), 3.90 (m, 1H), 2.78 (q, 3H, J=7.0 Hz), 2.62–2.56 (m, 1H), 2.47–2.24 (m, 6H), 1.66–1.50 (m, 6H), 1.26 (s, 3H), 1.16–1.03 (m, 3H), 0.88–0.84 (m, 2H), 0.71 (d,3H, J=6.9 Hz); $^{13}$C NMR (MeOH-d4) δ 164.1, 147.5, 146.0, 142.6, 122.1, 119.8, 119.4, 107.3, 105.5, 103.1, 102.6, 68.7, 50.1, 45.6, 41.2, 41.1, 31.7, 29.4, 28.8, 21.5, 21.1, 20.3, 18.4, 17.4, 16.8. Anal. ($C_{31}H_{28}N_2O_3$): C, H, N.

Opioid Binding Assays. Mu binding sites were labeled using [$^3$H][D-Ala$^2$-MePhe$^4$, Gly-ol$^5$]enkephalin ([$^3$H] DAMGO) (2.0 nM, SA=45.5 Ci/mmol), and delta binding sites were labeled using [$^3$H][D-Ala$^2$,D-Leu$^5$]enkephalin (2.0 nM, SA=47.5 Ci/mmol) using rat brain membranes prepared as described.[4] Kappa-1 binding sites were labeled using [$^3$H]U69,593 (2.0 nM, SA=45.5 Ci/mmol) and guinea pig membranes pretreated with BIT and FIT to deplete the mu and delta binding sites.[5]

[$^3$H]DAMGO binding proceeded as follows: 12×75 mm polystyrene test tubes were prefilled with 100 μL of the test drug which was diluted in binding buffer (BB: 10 mM Tris-HCl, pH 7.4, containing 1 mg/mL BSA), followed by 50 μL of BB, and 100 μL of [$^3$H]DAMGO in a protease inhibitor cocktail (10 mM Tris-HCl, pH 7.4, which contained bacitracin (1 mg/mL), bestatin (100 μg/mL), leupeptin (40 μg/mL), and chymostatin (20 μg/mL). Incubations were initiated by the addition of 750 μL of the prepared membrane preparation containing 0.2 mg/mL of protein and proceeded for 4 to 6 h at 25° C. The ligand was displaced by 10 concentrations of test drug, in triplicate, 2×. Nonspecific binding was determined using 20 μM levallorphan. Under these conditions, the $K_d$ of [$^3$H]DAMGO binding was 4.35 nM. Brandel cell harvesters were used to filter the samples over Whatman GF/B filters, which were presoaked in washbuffer (ice-cold 10 mM Tris-HCl, pH 7.4).

[$^3$H][D-Ala$^2$,D-Leu$^5$]enkephalin binding proceeded as follows: 12×75 mm polystyrene test tubes were prefilled with 100 μL of the test drug which was diluted in BB, followed by 100 μL of a salt solution containing choline chloride (1 M, final concentration of 100 mM), MnCl2 (30 mM, final concentration of 3.0 mM), and, to block mu sites, DAMGO (1000 nM, final concentration of 100 nM), followed by 50 μL of [$^3$H][D-Ala$^2$,D-Leu$^5$]enkephalin in the protease inhibitor cocktail. Incubations were initiated by the addition of 750 μL of the prepared membrane preparation containing 0.41 mg/mL of protein and proceeded for 4 to 6 h at 25° C. The ligand was displaced by 10 concentrations of test drug, in triplicate, 2×. Nonspecific binding was determined using 20 μM levallorphan. Under these conditions the $K_d$ of [$^3$H][D-Ala$^2$,D-Leu$^5$]enkephalin binding was 2.95 nM. Brandel cell harvesters were used to filter the samples over Whatman GF/B filters, which were presoaked in wash buffer (ice-cold 10 mM Tris-HCl, pH 7.4).

[$^3$H]U69,593 binding proceeded as follows: 12×75 mm polystyrene test tubes were prefilled with 100 μL of the test drug which was diluted in BB, followed by 50 μL of BB, followed by 100 μL of [$^3$H]U69,593 in the standard protease inhibitor cocktail with the addition of captopril (1 mg/mL in 0.1N acetic acid containing 10 mM 2-mercapto-ethanol to give a final concentration of 1 μg/mL). Incubations were initiated by the addition of 750 μL of the prepared membrane preparation containing 0.4 mg/mL of protein and proceeded for 4 to 6 h at 25° C. The ligand was displaced by 10 concentrations of test drug, in triplicate, 2×. Nonspecific binding was determined using 1 μM U69,593. Under these conditions the $K_d$ of [$^3$H]U69,593 binding was 3.75 nM. Brandel cell harvesters were used to filter the samples over Whatman GF/B filters, which were presoaked in wash buffer (ice-cold 10 mM Tris-HCl, pH 7.4) containing 1% PEI.

For all three assays, the filtration step proceeded as follows: 4 mL of the wash buffer was added to the tubes, rapidly filtered and was followed by two additional wash cycles. The tritium retained on the filters was counted, after an overnight extraction into ICN Cytoscint cocktail, in a Taurus beta counter at 44% efficiency.

$^{35}$S-GTP-γ-S Binding Assay. Ten frozen guinea pig brains (Harlan Bioproducts for Science, Inc, Indianapolis, Ind.) were thawed, and the caudate putamen were dissected and homogenized in buffer A (3 mL/caudate) (Buffer A=10 mM Tris-HCl, pH 7.4 at 4° C. containing 4 μg/mL leupeptin, 2 μg/mL chymostatin, 10 μg/mL bestatin, and 100 μg/mL bacitracin) using a polytron (Brinkman) at setting 6 until a uniform suspension was achieved. The homogenate was centrifuged at 30,000×g for 10 min at 4° C. and the supernatant discarded. The membrane pellets were washed by resuspension and centrifugation twice more with fresh buffer A, aliquotted into microfuge tubes, and centrifuged in a Tomy refrigerated microfuge (model MTX 150) at maximum speed for 10 min. The supernatants were discarded, and the pellets were stored at −80° C. until assayed.

For the [$^{35}$S]GTP-γ-S binding assay, all drug dilutions were made up in buffer B [50 mM TRIS-HCl, pH 7.7/0.1% BSA]. Briefly, 12×75 mm polystyrene test tubes received the following additions: (a) 50 μL buffer B with or without an agonist, (b) 50 μL buffer B with or without 60 μM GTP-γ-S for nonspecific binding, (c) 50 μL buffer B with or without an antagonist, (d) 50 μL salt solution which contained in buffer B 0.3 nM [$^{35}$S]GTP-γ-S, 600 mM NaCl, 600 μM GDP, 6 mM dithiothreitol, 30 mM MgCl$_2$, and 6 mM EDTA, and (e) 100 μL membranes in buffer B to give a final concentration of 10 μg per tube. The final concentration of the reagents were 100 mM NaCl, 5 mM MgCl$_2$, 1 mM EDTA, 1 mM dithiothreitol, 100 μM GDP, 0.1% BSA, 0.05–0.1 nM [$^{35}$S]GTP-γ-S, 500 nM or 10 μM agonists, and varying concentrations (at least 10 different concentrations) of antagonists. The reaction was initiated by the addition of membranes and terminated after 4 h by addition of 3 mL ice-cold (4° C.) purified water (Milli-Q uv-Plus, Millipore) followed by rapid vacuum filtration through Whatman GF/B filters presoaked in purified water. The filters were then washed once with 5 mL ice-cold water. Bound radioactivity was counted by liquid scintillation spectroscopy using a Taurus (Micromedic) liquid scintillation counter at 98% efficiency after an overnight extraction in 5 mL Cytoscint scintillation fluid. Nonspecific binding was determined in the presence of 10 μM GTP-γ-S. Assays were performed in triplicate, and each experiment was performed at least 3×.

Data Analysis. The data of the two separate experiments (opioid binding assays) or three experiments ([$^{35}$S]-GTP-γ-S assay) were pooled and fit, using the nonlinear least-squares curve-fitting language MLAB-PC (Civilized Software, Bethesda, Md.), to the two-parameter logistic equation[6] for the best-fit estimates of the IC$_{50}$ and slope factor. The $K_i$ values were then determined using the equation:

$$IC_{50}/1+([L]/K_d).$$

| % Inhibition Data for Compounds of Formula (I) in a Kappa Receptor Assay | | | |
|---|---|---|---|
| $R_1$ | $R_2$ | $R_3$ (acid) | % Inhibition |
| H | H | PA5 | 13 |
| H | H | BA1 | 20 |
| H | H | BA2 | 20 |
| H | H | BA4 | 21 |
| H | H | BA6 | 32 |
| H | H | BA8 | 11 |
| H | H | BA9 | 24 |
| H | H | BA10 | 28 |
| H | H | BA12 | 6 |
| H | H | BA13 | 9 |
| H | H | BA14 | 11 |
| H | H | BA16 | 11 |
| H | H | BA22 | 2 |
| H | H | BA23 | 13 |
| H | H | BA24 | 2 |
| H | H | BA25 | 6 |
| H | H | AA2 | 1 |
| H | H | AA4 | 0 |
| H | H | PP1 | 9 |
| H | H | PP2 | 23 |
| H | H | PP3 | 17 |
| H | H | PP4 | 1 |
| H | H | PP5 | 8 |
| H | H | PP6 | 14 |
| H | H | PP12 | 29 |
| H | H | PP15 | 19 |

% Inhibition Data for Compounds of Formula (I) in a Kappa Receptor Assay

| $R_1$ | $R_2$ | $R_3$ (acid) | % Inhibition |
|---|---|---|---|
| H | H | FA1 | 13 |
| H | H | FA2 | 9 |
| H | H | FA3 | 50 |
| H | H | FA4 | 33 |
| H | H | FA5 | 39 |
| H | H | FA6 | 27 |
| H | H | FA7 | 29 |
| H | H | FA8 | 35 |
| H | H | FA9 | 33 |
| H | H | FA10 | 8 |
| H | H | HA1 | 20 |
| H | H | HA2 | 42 |
| H | H | HA3 | 9 |
| H | H | HA4 | 15 |
| H | H | HA5 | 20 |
| H | H | OA23 | 8 |
| H | H | PB1 | 37 |
| H | H | CA2 | 35 |
| H | H | CA10 | 23 |
| H | H | CA11 | 13 |
| H | H | CA12 | 15 |
| H | H | PA38 | 14 |
| H | H | CA19 | 10 |
| H | H | CA20 | 12 |
| H | H | CA22 | 19 |
| H | H | CA38 | 27 |
| H | H | PA9 | 18 |
| H | H | PA10 | 9 |
| H | H | PA13 | 25 |
| H | H | PA15 | 17 |
| H | H | PA18 | 16 |
| H | H | PA23 | 9 |
| H | H | PA27 | 18 |
| H | H | PA28 | 9 |
| H | H | PA29 | 10 |
| H | H | PA32 | 22 |
| H | H | PA3 | 20 |
| H | H | PA4 | 11 |
| H | H | PA7 | 9 |
| H | H | PA17 | 13 |
| H | H | PA22 | 19 |
| H | H | PA8 | 23 |
| H | H | NA1 | 16 |
| H | H | NA2 | 6 |
| H | H | NA3 | 13 |
| H | H | NA4 | 1 |
| H | H | NA5 | 10 |
| H | H | NA6 | 2 |
| H | H | NA7 | 2 |
| H | H | NA8 | 15 |
| H | H | NA9 | 26 |
| H | H | NA10 | 22 |
| H | H | NA11 | 15 |
| H | H | BA7 | 2 |
| H | H | PA38 | 5 |
| H | H | AA1 | 8 |
| H | H | AA2 | 6 |
| H | H | AA4 | 3 |
| H | H | PP6 | 11 |
| H | $CH_3$ | BA4 | 12 |
| H | $CH_3$ | BA10 | 13 |
| H | $CH_3$ | BA1 | 6 |
| H | $CH_3$ | CA1 | 9 |
| H | $CH_3$ | CA5 | 6 |
| H | $CH_3$ | PA37 | 5 |
| H | $CH_3$ | PA5 | 11 |
| H | $CH_3$ | PA14 | 0 |
| H | $CH_3$ | PA32 | 0 |
| H | $CH_3$ | PP2 | 0 |
| H | $CH_3$ | PP5 | 0 |
| H | $CH_3$ | PP6 | 0 |
| H | $CH_3$ | PP1 | 0 |
| H | $CH_3$ | PP7 | 0 |
| H | $CH_3$ | BA11 | 0 |
| H | $CH_3$ | CA4 | 0 |
| αi-Pr | H | BA4 | 9 |
| αi-Pr | H | BA5 | 19 |
| αi-Pr | H | BA8 | 0 |
| αi-Pr | H | BA7 | 5 |
| αi-Pr | H | BA11 | 0 |
| αi-Pr | H | BA12 | 0 |
| αi-Pr | H | BA13 | 26 |
| αi-Pr | H | BA15 | 1 |
| αi-Pr | H | BA19 | 0 |
| αi-Pr | H | BA20 | 0 |
| αi-Pr | H | BA21 | 3 |
| αi-Pr | H | CA1 | 0 |
| αi-Pr | H | CA10 | 0 |
| αi-Pr | H | CA11 | 0 |
| αi-Pr | H | CA7 | 0 |
| αi-Pr | H | PA5 | 6 |
| αi-Pr | H | PA7 | 14 |
| αi-Pr | H | PA9 | 0 |
| αi-Pr | H | PA10 | 0 |
| αi-Pr | H | PA13 | 10 |
| αi-Pr | H | PA15 | 4 |
| αi-Pr | H | PA18 | 7 |
| αi-Pr | H | PA22 | 0 |
| αi-Pr | H | PA27 | 18 |
| αi-Pr | H | PA28 | 6 |
| αi-Pr | H | CA16 | 0 |
| αi-Pr | H | CA18 | 0 |
| αi-Pr | H | PA29 | 1 |
| αi-Pr | H | PP1 | 28 |
| αi-Pr | H | PP2 | 3 |
| αi-Pr | H | PP3 | 27 |
| αi-Pr | H | PP4 | 18 |
| αi-Pr | H | PP5 | 20 |
| αi-Pr | H | PP6 | 70 |
| αi-Pr | H | PP7 | 13 |
| αi-Pr | H | PP8 | 17 |
| αi-Pr | H | PP12 | 23 |
| αi-Pr | H | PP15 | 26 |
| αi-Pr | H | PP16 | 31 |
| αi-Pr | H | PP17 | 43 |
| αi-Pr | H | CA5 | 4 |
| αi-Pr | H | CA7 | 16 |
| αi-Pr | H | CA12 | 15 |
| αi-Pr | H | PA8 | 21 |
| αi-pr | H | PA23 | 6 |
| αi-Pr | H | PA32 | 13 |
| αi-Pr | H | BA1 | 3 |
| αi-Pr | H | CA4 | 3 |
| αi-Pr | H | PA18 | 7 |
| αi-Pr | H | NA1 | 14 |
| αi-Pr | H | NA2 | 3 |
| αi-Pr | H | NA3 | 16 |
| αi-Pr | H | NA4 | 43 |
| αi-Pr | H | NA5 | 61 |
| αi-Pr | H | NA6 | 1 |
| αi-Pr | H | NA7 | 22 |
| αi-Pr | H | NA8 | 3 |
| αi-Pr | H | NA9 | 33 |
| αi-Pr | H | NA10 | 3 |
| αi-Pr | H | NA11 | 34 |
| αi-Pr | H | BA7 | 25 |
| αi-Pr | H | PA38 | 4 |
| αi-Pr | H | AA1 | 3 |
| αi-Pr | H | AA2 | 4 |
| αi-Pr | H | AA4 | 13 |
| αi-Pr | H | CA2 | 5 |
| αi-Pr | H | FA1 | 5 |
| αi-Pr | H | FA2 | 6 |
| αi-Pr | H | FA3 | 9 |
| αi-Pr | H | FA4 | 17 |
| αi-Pr | H | FA5 | 10 |
| αi-Pr | H | FA6 | 10 |
| αi-Pr | H | FA7 | 10 |
| αi-Pr | H | FA8 | 27 |
| αi-Pr | H | FA9 | 14 |

% Inhibition Data for Compounds of Formula (I) in a Kappa Receptor Assay

| $R_1$ | $R_2$ | $R_3$ (acid) | % Inhibition |
|---|---|---|---|
| αi-Pr | H | FA10 | 6 |
| αi-Pr | H | HA1 | 6 |
| αi-Pr | H | HA2 | 1 |
| αi-Pr | H | HA3 | 0 |
| αi-Pr | H | HA4 | 10 |
| αi-Pr | H | HA5 | 10 |
| αi-Pr | H | OA23 | 0 |
| αi-Pr | H | PB1 | 7 |
| αi-Pr | H | PA14 | 8 |
| βi-Pr | H | PP4 | 52 |
| βi-Pr | H | PP6 | 11 |
| βi-Pr | H | PP8 | 10 |
| βi-Pr | H | PP12 | 50 |
| βi-Pr | H | PP15 | 24 |
| βi-Pr | H | PP16 | 8 |
| βi-Pr | H | PP17 | 10 |
| βi-Pr | H | PP18 | 5 |
| αCH$_3$ | H | PP6 | 11 |
| αCH$_3$ | CH$_3$ | CA1 | 3 |
| αCH$_3$ | CH$_3$ | CA2 | 0 |
| αCH$_3$ | CH$_3$ | CA8 | 0 |
| αCH$_3$ | CH$_3$ | CA14 | 0 |
| αCH$_3$ | CH$_3$ | CA15 | 1 |
| αCH$_3$ | CH$_3$ | CA19 | 0 |
| αCH$_3$ | CH$_3$ | CA20 | 10 |
| αCH$_3$ | CH$_3$ | CA24 | 5 |
| αCH$_3$ | CH$_3$ | CA28 | 0 |
| αCH$_3$ | CH$_3$ | CA30 | 7 |
| αCH$_3$ | CH$_3$ | BA1 | 7 |
| αCH$_3$ | CH$_3$ | BA4 | 7 |
| αCH$_3$ | CH$_3$ | BA8 | 8 |
| αCH$_3$ | CH$_3$ | BA13 | 8 |
| αCH$_3$ | CH$_3$ | BA19 | 8 |
| αCH$_3$ | CH$_3$ | BA20 | 5 |
| αCH$_3$ | CH$_3$ | BA21 | 5 |
| αCH$_3$ | CH$_3$ | BA23 | 6 |
| αCH$_3$ | CH$_3$ | BA25 | 5 |
| αCH$_3$ | CH$_3$ | PA5 | 6 |
| αCH$_3$ | CH$_3$ | PA8 | 1 |
| αCH$_3$ | CH$_3$ | PA10 | 0 |
| αCH$_3$ | CH$_3$ | PA19 | 0 |
| αCH$_3$ | CH$_3$ | PA21 | 0 |
| αCH$_3$ | CH$_3$ | PA27 | 4 |
| αCH$_3$ | CH$_3$ | PA28 | 0 |
| αCH$_3$ | CH$_3$ | PA29 | 1 |
| αCH$_3$ | CH$_3$ | PA32 | 0 |
| αCH$_3$ | CH$_3$ | PA14 | 0 |
| αCH$_3$ | CH$_3$ | PP1 | 6 |
| αCH$_3$ | CH$_3$ | PP4 | 2 |
| αCH$_3$ | CH$_3$ | PP5 | 3 |
| αCH$_3$ | CH$_3$ | PP7 | 1 |
| αCH$_3$ | CH$_3$ | PP8 | 0 |
| αCH$_3$ | CH$_3$ | PP10 | 5 |
| αCH$_3$ | CH$_3$ | BAL1 | 0 |
| αCH$_3$ | CH$_3$ | GAB1 | 0 |
| αCH$_3$ | CH$_3$ | INP1 | 0 |
| αCH$_3$ | CH$_3$ | CA13 | 1 |
| αCH$_3$ | CH$_3$ | PA17 | 0 |
| αCH$_3$ | CH$_3$ | PA9 | 10 |
| αCH$_3$ | CH$_3$ | BA24 | 2 |
| αCH$_3$ | CH$_3$ | PP2 | 5 |
| αCH$_3$ | CH$_3$ | PP3 | 1 |
| αCH$_3$ | CH$_3$ | PP6 | 1 |
| αCH$_3$ | CH$_3$ | PA20 | 4 |
| αPh | CH$_3$ | CA1 | 0 |
| αPh | CH$_3$ | CA4 | 0 |
| αPh | CH$_3$ | CA9 | 1 |
| αPh | CH$_3$ | CA14 | 0 |
| αPh | CH$_3$ | CA15 | 3 |
| αPh | CH$_3$ | CA19 | 0 |
| αPh | CH$_3$ | CA20 | 2 |
| αPh | CH$_3$ | BA1 | 3 |
| αPh | CH$_3$ | BA2 | 0 |
| αPh | CH$_3$ | BA4 | 0 |
| αPh | CH$_3$ | PA14 | 3 |
| αPh | CH$_3$ | PA19 | 0 |
| αPh | CH$_3$ | PP1 | 4 |
| αPh | CH$_3$ | PP2 | 4 |
| αPh | CH$_3$ | OA1 | 9 |
| αPh | CH$_3$ | OA3 | 4 |
| αPh | CH$_3$ | CA2 | 5 |
| αPh | CH$_3$ | BA21 | 7 |
| αPh | CH$_3$ | PP3 | 5 |
| αPh | CH$_3$ | GAB1 | 11 |
| αPh | CH$_3$ | BA8 | 4 |
| αPh | CH$_3$ | BA10 | 0 |
| αPh | CH$_3$ | BA15 | 15 |
| αPh | CH$_3$ | PA8 | 1 |
| αPh | CH$_3$ | PA9 | 0 |
| αPh | CH$_3$ | PA10 | 6 |
| αPh | CH$_3$ | PA20 | 6 |
| αPh | CH$_3$ | PA21 | 9 |
| αPh | CH$_3$ | PP6 | 7 |
| αPh | CH$_3$ | PP7 | 0 |
| αPh | CH$_3$ | PP8 | 0 |
| αPh | CH$_3$ | OA2 | 0 |

| | Amino Alkyl Acids | |
|---|---|---|
| AA 1 | 1-Piperidine Propionic Acid | 157.21 |
| AA 2 | 2-N,N-Dimethyl Glycine | 103.21 |
| AA 3 | 3-N,N-Dimethyl Amino Propionic Acid | |
| AA 4 | 4-N,N-Dimethyl Amino Butyric Acid | 167.64 |
| | Benzoic Acids | |
| BA 1 | Benzoic Acid | 122.12 |
| BA 2 | 2-Chlorobenzoic Acid | 156.57 |
| BA 3 | 2-Acetamidobenzoic Acid | 179.18 |
| BA 4 | 2-Phenoxybenzoic Acid | 214.22 |
| BA 6 | 3-Chlorobenzoic Acid | 156.57 |
| BA 8 | 3-Phenoxybenzoic Acid | 214.22 |
| BA 9 | 3-Hydroxybenzoic Acid | 138.12 |
| BA 10 | 4-Chlorobenzoic Acid | 156.57 |
| BA 7 | 4-Dimethylaminobenzoic Acid | 165.19 |
| BA 12 | 4-Dodecyloxybenzoic Acid | 306.45 |
| BA 13 | 4-Butoxybenzoic Acid | 212.69 |
| BA 14 | 4-Hydroxybenzoic Acid | 138.12 |
| BA 16 | 4-tert-butylbenzoic Acid | 178.23 |
| BA 18 | 4-Acetamidobenzoic Acid | 179.18 |
| BA 19 | o-Anisic Acid | 152.15 |
| BA 20 | m-Anisic Acid | 152.15 |
| BA 21 | p-Anisic Acid | 152.15 |
| BA 22 | 2-Benzoylbenoic Acid | 226.23 |
| BA 23 | 2-Biphenylbenzoic Acid | 98.22 |
| BA 24 | 4-Biphenylbenzoic Acid | 98.22 |
| BA 25 | 3-Dimethylaminobenzoic Acid | 165.19 |
| BA 26 | 2-Fluorobenzoic Acid | 140.11 |
| BA 27 | 3-Nitrobenzoic Acid | 167.12 |
| BA 28 | o-Tolylic Acid | 136.15 |
| BA 29 | m-Tolylic Acid | 136.15 |
| BA 30 | p-Tolylic Acid | 136.15 |
| BA 31 | 4-Fluoro-3-nitrobenzoic | 185.11 |
| BA 32 | 3,4-Dichlorobenzoic Acid | 191.01 |
| BA33 | 2-Hydroxy Benzoic acid | 138.12 |
| BA34 | 4-Chloro-3-Nitro Benzoic Acid | 201.57 |
| BA35 | 4-Flurobenzoic Acid | 140.11 |
| BA36 | 2-Nitrobenzoic acid | 167.12 |
| BA37 | 4-Nitrobenzoic acid | 167.12 |
| | Cinnamic Acids | |
| CA 1 | a-Methylcinnamic Acid | 162.19 |
| CA 2 | a-Phenylcinnamic Acid | 226.4 |
| CA 3 | 2-Bromo-4,5-dimethoxycinnamic Acid | 287.11 |
| CA 4 | 2-Chlorocinnamic Acid | 182.61 |
| CA 5 | 2,4-Dichlorocinnamic Acid | 217.05 |

-continued

| | | |
|---|---|---|
| CA 6 | 3,4-Dihydroxycinnamic Acid | 180.16 |
| CA 7 | 2,4-Dimethoxycinnamic Acid | 208.21 |
| CA 8 | 3,5-Di-tert-butyl-4-hydroxycinnamic Acid | 276.37 |
| CA 9 | 3-Fluorocinnamic Acid | 166.15 |
| CA 10 | 2-Hydroxycinnamic Acid | 164.16 |
| CA 11 | 3-Hydroxycinnamic Acid | 164.16 |
| CA 12 | 4-Hydroxycinnamic Acid | 164.16 |
| CA 13 | 2-Methoxycinnamic Acid | 178.19 |
| CA 14 | 3-Methoxycinnamic Acid | 178.19 |
| CA 15 | 4-Methoxycinnamic Acid | 178.19 |
| CA 16 | 2-Methylcinnamic Acid | 162.19 |
| CA 17 | 3-Methylcinnamic Acid | 162.19 |
| CA 18 | 4-Methylcinnamic Acid | 162.19 |
| CA 19 | 3-(1-Naphthyl)acrylic Acid | 224.46 |
| CA 20 | 4-Phenylcinnamic Acid | 224.26 |
| CA 21 | 3,4,5-Trimethoxycinnamic Acid | 238.24 |
| CA 22 | 4-Isopropylcinnamic acid | 190.24 |
| CA23 | 2,6-Dichloro | 218.063 |
| CA24 | 3-benzyloxy | 254.234 |
| CA25 | 2-bromo-4,5-dimethoxy | 287.12 |
| CA26 | 2-chloro-6-fluoro | 200.6 |
| CA27 | alpha-methyl-2,4,5-trimethoxy | 252.27 |
| CA28 | 2-n-hexyloxy | 250.22 |
| CA29 | 5-bromo-2-methoxy | 257.09 |
| CA30 | 2-benzyloxy | 254.234 |
| CA31 | 2,4,5-trimethoxy | 238.24 |
| CA32 | 2,6-difluoro | 184.14 |
| CA33 | 2-t-butylthio | 236.157 |
| CA34 | 2-chloro-5-nitro | 227.61 |
| CA35 | 2,3-dimethoxy | 208.21 |
| CA36 | 3,5-dit-butyl-4-hydroxy | 276.37 |
| CA37 | 2,5-dimethoxy | 208.22 |
| CA 38 | trans-Cinnamic Acid | 147 |
| CA39 | cis-Cinnamic Acid | 147 |
| Fatty Acids | | |
| FA 1 | Acetic Acid | 60.05 |
| FA 2 | Propionic Acid | 74.08 |
| FA 3 | Pivalic Acid | 102.13 |
| FA 4 | 1-Phenyl-1-cyclopentane Acid | 162.19 |
| FA 5 | 1-Phenyl-1-cyclopropane Acid | 190.24 |
| FA 6 | Isovaleric Acid | 102.13 |
| FA 7 | 4-Methylvaleric Acid | 116.16 |
| FA 8 | Cyclopentylacetic Acid | 128.17 |
| FA 9 | Cyclopentylcarboxylic Acid | 114.14 |
| FA 10 | trans-2-Phenyl-1-cyclopropyl CA | 162.19 |
| FA 11 | Cyclohexane carboxylic Acd | 128.17 |
| Hydroxy Acids | | |
| HA 1 | 2-Hydroxy-3-methyl butyric | 118.13 |
| HA 2 | 2-Hydroxy-2-methyl butyric | 118.13 |
| HA 3 | 3-Hydroxy butyric | 104.11 |
| HA 4 | 3-Hydroxy-4-trimethylamino butyric | 197.66 |
| HA 5 | 2-Phenyl-3-hydroxy propionic | 166.18 |
| Nicotinic Acids | | |
| NA 1 | 2(n-Amylthio)nicotinic Acid | 225.31 |
| NA 2 | 5-Bromonicotinic Acid | 202.01 |
| NA 3 | 6-Chloronicotinic Acid | 157.56 |
| NA 4 | 2-Chloronicotinic Acid | 157.56 |
| NA 5 | 2-(Methylthio)nicotinic Acid | 169.2 |
| NA 6 | Nicotinic Acid | 123.11 |
| NA 7 | Picolinic Acid | 123.11 |
| NA 8 | 2-Pyridylacetic Acid HCl | 173.6 |
| NA 9 | 3-Pyridylacetic Acid HCl | 173.6 |
| NA 10 | 4-Pyridylacetic Acid HCl | 173.6 |
| NA 11 | 2-(Phenylthio)Nicotinic Acid | 231.27 |
| NA 12 | 2-Hydroxy-6-methyl Nicotinic | 153.14 |
| NA13 | 3-(3-pyridyl)acrylic acid | 149.15 |
| NA 14 | 3-(4-pyridyl)acrylic acid | 149.15 |
| Propionic Acid | | |
| PP1 | Phenyl Propionic | 150.18 |
| PP2 | 3,3-Diphenylpropionic Acid | 226.28 |
| PP3 | 3-Phenylbutyric Acid | 164.2 |
| PP4 | 3-(2-Hydroxyphenyl)propionic Acid | 166.18 |
| PP 5 | 3-(3-Hydroxyphenyl)propionic Acid | 166.18 |
| PP 6 | 3-(4-Hydroxyphenyl)propionic Acid | 166.18 |
| PP7 | 3-(3-Methoxyphenyl)propionic Acid | 180.2 |
| PP8 | 3-(4-Methoxyphenyl)propionic Acid | 180.2 |
| PP9 | 3-(3,4,5-Trimethoxyphenyl)propionic Acid | 240.26 |
| PP10 | 3-(2-Methoxyphenyl)propionic Acid | 180.2 |
| PP11 | 3-(2,5-Dimethoxyphenyl)propionic Acid | 210.24 |
| PP12 | 3-(2-Chlorophenyl)propionic Acid | 184.62 |
| PP13 | 3-(4-Aminophenyl)propionic Acid | 165.119 |
| PP14 | 3-(4-Fluorophenyl)propionic Acid | 168.17 |
| PP15 | 3-(3,4-Dihydroxyphenyl)propionic Acid | 182.18 |
| PP16 | 3-(3-Methoxy-4-hydroxyphenyl) | 196.2 |
| PP17 | 3-(3,5-dinotro-4-hydroxyphenyl) | 256.2 |
| PP18 | 3-(Pentaflurophenyl)propionic Acid | |
| PP19 | 3-(4-Bocaminophenyl)propionic Acid | 265 |
| PP21 | 2,2-Diphenylpropionic Acid | 226.28 |
| Phenylacetic Acid | | |
| PA 1 | 4-Aminophenylacetic Acid | 151.17 |
| PA 2 | 4-Biphenylacetic Acid | 288.55 |
| PA 3 | 2-Bromophenylacetic Acid | 215.05 |
| PA 4 | 4-Bromophenylacetic Acid | 215.05 |
| PA 5 | 4-(n-Butoxy)phenylacetic Acid | 208.26 |
| PA 7 | 3-Chloro-4-hydroxyphenylacetic Acid | 186.59 |
| PA 8 | 2-Chlorophenylacetic Acid | 170.6 |
| PA 9 | 3-Chlorophenylacetic Acid | 170.6 |
| PA 10 | 4-Chlorophenylacetic Acid | 170.6 |
| PA 11 | 2-Chloro-6-fluorophenylacetic Acid | 188.59 |
| PA 12 | 2,4-Dichlorophenylacetic Acid | 205.04 |
| PA 13 | 2,6-Dichlorophenylacetic Acid | 205.04 |
| PA 14 | 3,4-Dichlorophenylacetic Acid | 205.04 |
| PA 15 | 2,5-Dimethoxyphenylacetic Acid | 196.2 |
| PA 16 | 3,4-Dimethoxyphenylacetic Acid | 196.2 |
| PA 17 | 2,5-Dimethylphenylacetic Acid | 164.2 |
| PA 18 | 2,4-Dinitrophenylacetic Acid | 226.15 |
| PA 19 | 2-Fluorophenylacetic Acid | 154.14 |
| PA 20 | 3-Fluorophenylacetic Acid | 154.14 |
| PA 21 | 4-Fluorophenylacetic Acid | 154.14 |
| PA 22 | 2-Hydroxyphenylacetic Acid | 152.15 |
| PA 23 | 4-Hydroxyphenylacetic Acid | 152.15 |
| PA 24 | 2-Methoxyphenylacetic Acid | 166.18 |
| PA 25 | 3-Methoxyphenylacetic Acid | 166.18 |
| PA 26 | 4-Methoxyphenylacetic Acid | 166.18 |
| PA 27 | 2-Methylphenylacetic Acid | 150.18 |
| PA 28 | 3-Methylphenylacetic Acid | 150.18 |
| PA 29 | 4-Methylphenylacetic Acid | 150.18 |
| PA 30 | 2-Nitrophenylacetic Acid | 181.15 |
| PA 31 | 4-Nitrophenylacetic Acid | 181.15 |
| PA 32 | Phenylacetic Acid | 136.15 |
| PA 33 | 2-Trifluormethylophenylacetic Acid | 204.15 |
| PA 34 | 3-Trifluoromethylphenylacetic Acid | 204.15 |
| PA 35 | 3,4,5-Trimethoxyphenylacetic Acid | 226.23 |
| PA 36 | 4-Ethoxyphenylacetic Acid | 180.22 |
| PA 37 | Mesitylacetic acid | 178.23 |
| PA 38 | 4-Dimethyl Amino PA | |
| PA 39 | 3-Hydroxyphenyl PA | |
| PA 40 | Diphenyl Acetic | |

REFERENCES (1) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and $\mu$ receptor subtype-selectivity in (+)-(3R, 4R)-dimethyl-4-(3-hydroxyphenyl)piperidine opioid antagonists. *J. Med. Chem.* 1998, 41(11), 1980–1990.

(2) Mitch, C. H.; Leander, J. D.; Mendelsohn, L. G.; Shaw, W. N.; Wong, D. T.; Cantrell, B. E.; Johnson, B. G.; Reel, J. K.; Snoddy, J. D.; Takemori, A. E.; Zimmerman, D. M. 3,4-Dimethyl-4-(3-hydroxyphenyl)piperidines: Opioid antagonists with potent anorectant activity. *J. Med. Chem.* 1993, 36(20), 2842–2850.

(3) Xu, H.; Lu, Y.-F.; Partilla, J. S.; Brine, G. A.; Carroll, F. I.; Rice, K. C.; Lai, J.; Porreca, F.; Rothman, R. B. Opioid peptide receptor studies. 6. The 3-methylfentanyl congeners RTI-4614-4 and its enantiomers differ in efficacy, potency, and intrinsic efficacy as measured by stimulation of [$^{35}$S]GTP-γ-S binding using cloned $\mu$-opioid receptors. *Analgesia* 1997, 3, 35–42.

(4) Rothman, R. B.; Xu, H.; Seggel, M.; Jacobson, A. E.; Rice, K. C.; Brine, G. A.; Carroll, F. I. RTI-4614-4: an analog of (+)-cis-3-methylfentanyl with a 27,000-fold binding selectivity for mu versus delta opioid binding sites. *Life Sci.* 1991, 48, PL111–PL-116.

(5) Rothman, R. B.; Bykov, V.; de Costa, B. R.; Jacobson, A. E.; Rice, K. C.; Brady, L. S.
Interaction of endogenous opioid peptides and other drugs with four kappa opioid binding sites in guinea pig brain. *Peptides* 1990, 11, 311–331.

(6) Rodbard, D.; Lenox, R. H.; Wray, H. L.; Ramseth, D. Statistical characterization of the random errors in the radioinmmunoassay dose-response variable. *Clin. Chem.* 1976, 22, 350–58.

(7) Takemori et al, *J. Pharm. Exp. Ther.*, 1988, 246 (1), 255–258.

TABLE 1

Results of Inhibition Screening of Selected Structural Isomers of Compound 8 Taken from the Library versus Kappa Opioid Selective Ligand [$^3$H]U69,593

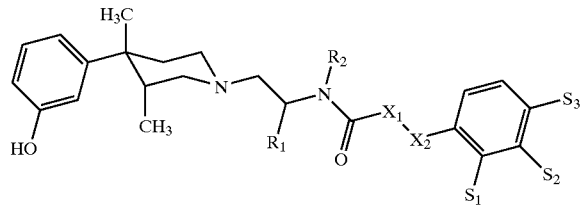

| compd | R1 | R2 | X1 | X2 | $S_1$ | $S_2$ | $S_3$ | % Inhibition at 100 nM |
|---|---|---|---|---|---|---|---|---|
| 8 | i-Pr | H | CH2 | CH2 | H | H | OH | 71 |
| 9 | i-Pr[a] | H | CH2 | CH2 | H | H | OH | 11 |

TABLE 1-continued

Results of Inhibition Screening of Selected Structural Isomers of Compound 8 Taken from the Library versus Kappa Opioid Selective Ligand [$^3$H]U69,593

| compd | R1 | R2 | X1 | X2 | $S_1$ | $S_2$ | $S_3$ | % Inhibition at 100 nM |
|---|---|---|---|---|---|---|---|---|
| 10 | i-Pr | H | CH2 | CH2 | H | H | H | 28 |
| 11 | i-Pr | H | CH2 | CH2 | H | OH | H | 20 |
| 12 | i-Pr | H | CH2 | CH2 | OH | H | H | 25 |
| 13 | i-Pr | H | CH2 | — | H | H | OH | 6 |
| 14 | i-Pr | H | CH[b] | CH[b] | H | H | OH | 15 |
| 15 | i-Pr | H | CH2 | CH2 | H | H | F | 26 |
| 16 | i-Pr | H | CH2 | CH2 | H | OH | OH | 31 |
| 17 | i-Pr | H | CH2 | CH2 | H | OCH3 | OH | 42 |
| 18 | i-Pr | H | CH2 | CH2 | H | H | OCH3 | 16 |
| 19 | H | H | CH2 | CH2 | H | H | OH | 11 |
| 20 | CH$_3$ | H | CH2 | CH2 | H | H | OH | 20 |
| 21 | H | CH$_3$ | CH2 | CH2 | H | H | OH | 0 |
| 22 | CH$_3$ | CH$_3$ | CH2 | CH2 | H | H | OH | 1 |
| 23 | C$_6$H$_5$ | CH$_3$ | CH2 | CH2 | H | H | OH | 7 |
| DMSO | | | | | | | | 4 |

[a]The carbon to which the i-Pr group is attached has the opposite stereochemistry from that in 8.
[b]Trans double bond

TABLE 2

Radioligand Binding Data for 8 and Related Compounds at Mu, Delta, and Kappa Opioid Receptor Assays

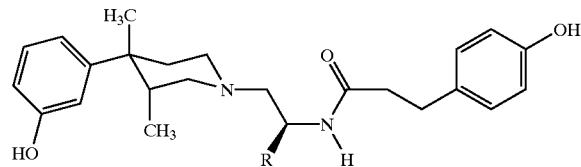

| compd | R | [$^3$H]DAMGO | [$^3$H]DADLE | [$^3$H]U69,593 | $\mu/\kappa$ | $\delta/\kappa$ |
|---|---|---|---|---|---|---|
| 8 | i-Pr | 393 ± 13.3 (0.89 ± 0.02) | >5700 | 6.91 ± 0.55 (0.81 ± 0.05) | 57 | >824 |
| 24 | i-Bu | 398 ± 72.3 (0.91 ± 0.16) | NA | 89.3 ± 7.03 (0.78 ± 0.05) | 4.5 | |
| 25 | sec-Bu | 421 ± 30.5 (0.91 ± 0.06) | NA | 8.84 ± 0.30 (0.87 ± 0.02) | 47 | |
| 26 | c-Hex | 234 ± 25.2 (0.84 ± 0.08) | NA | 83.1 ± 5.7 (0.79 ± 0.04) | 2.8 | |
| 27 | Benzyl | 9.6 ± 1.18 (0.89 ± 0.09) | NA | 54.6 ± 3.5 (0.86 ± 0.04) | 0.17 | |
| 5a[a] | | 0.74 ± 0.05 (0.89 ± 0.09) | 322 ± 38.1 (0.75 ± 0.09) | 122 ± 11.9 (0.52 ± 0.07) | 0.006 | 2.6 |

Ki (nM ± SD) (−n$_H$)

TABLE 2-continued

Radioligand Binding Data for 8 and Related Compounds at Mu, Delta, and Kappa Opioid Receptor Assays

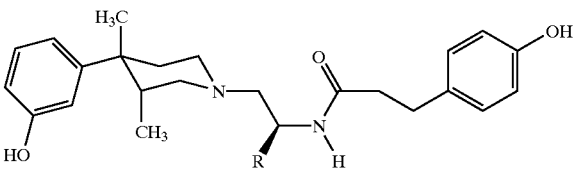

| compd | R | [³H]DAMGO | [³H]DADLE | [³H]U69,593 | μ/κ | δ/κ |
|---|---|---|---|---|---|---|
| 1 (nor-BNI)[b,c] | | 47.2 ± 3.3 | 42.9 ± 11 | 0.28 ± 0.07 | 181 | 150 |
| naltrexone[b] | | 1.39 ± 0.40 (0.94 ± 0.08) | 94.9 ± 6.6 (1.01 ± 0.09) | 4.71 ± 0.12 (1.05 ± 0.08) | 0.30 | 20.1 |

[a]Data taken from ref. 1.
[b]Data provided for reference; compound is not a derivative of 8.
[c]Data taken from ref. 7.
[³H]DAMGO, [³H]DPDPE, and [³H]U69593 were used as the radioligands for the mu, delta, and kappa assays, respectively. Guinea pig brain membranes were used.

TABLE 3

Inhibition by Antagonists of [³⁵S]GTPγS Binding in Guinea Pig Caudate Stimulated by DAMGO (μ), SNC80 (δ), and U69,593 (κ) Selective Opioid Agonists.

| | Ki (nM ± SD) (−n$_H$)[a] | | |
|---|---|---|---|
| Compd | DAMGO[b] | SNC80[c] | U69,593[d] |
| 8 | 7.25 ± 0.52 (1.11 ± 0.08) | 450 ± 74.1 (1.05 ± 0.17) | 4.70 ± 0.56 (1.38 ± 0.19) |
| 5a[e] | 0.039 ± 0.003 (1.06 ± 0.07) | 1.48 ± 0.094 (1.19 ± 0.08) | 1.04 ± 0.061 (1.07 ± 0.06) |
| 1, nor-BNI | 16.75 ± 1.47 (1.02 ± 0.09) | 10.14 ± 0.96 (1.18 ± 0.12) | 0.038 ± 0.005 (0.97 ± 0.12) |
| naltrexone | 0.93 ± 0.21 (1.03 ± 0.22) | 19.3 ± 2.25 (1.05 ± 0.17) | 2.05 ± 0.21 (1.38 ± 0.19) |

[a]See footnote a from Table 2. [b]DAMGO [(D-Ala², MePhe⁴, Gly-ol⁵) enkephalin]. Agonist selective for mu opioid receptor. [c]SNC-80 ([(+)-4-[(αR)-α-(2S,5R)-4-allyl-2,5-dimethyl-1-piperazinyl)-3-methoxybenzyl]-N,N-diethylbenzamide]. Agonist selective for delta opioid receptor. [d]U69,593 [(5α,7α,8β)-(−)-N-methyl-N-[7-(1-pyrrolidinyl)-1-oxaspiro[4,5]dec-8-yl] benzeneacetamide]. Agonist selective for kappa opioid receptor. [e]Data taken from ref. 1.

Analyses Appendix

N-{(2'S)-[3-(4-Hydroxyphenyl)propanamido]-3'-methylbutyl}-(3R,4R)-dimethyl-4-(3-hydroxyphenyl)piperidine (8).

Anal. calcd for $C_{27}H_{39}ClN_2O_3 \cdot 1.5H_2O$: C, 64.59, H, 8.43; N, 5.58. Found: C, 64.35; H, 8.12; N, 5.38.

N-{(2'S)-[3-(4-Hydroxyphenyl)propanamido]-4'-methylpentyl}-(3R,4R)-dimethyl-4-(3-hydroxyphenyl)piperidine (24).

Anal. calcd for $C_{28}H_{40}N_2O_3$: C, 74.30, H, 8.91; N, 6.19. Found: C, 74.12; H, 9.22; N, 6.30.

N-{(2'S)-[3-(4-Hydroxyphenyl)propanamido]-3'-methylpentyl}-(3R,4R)-dimethyl-(3-hydroxyphenyl)piperidine (25).

Anal. calcd for $C_{28}H_{40}N_2O_3$: C, 74.30, H, 8.91; N, 6.19. Found: C, 74.02; H, 9.20; N, 6.25.

N-{(2'S)-[3-(4-Hydroxyphenyl)propanamido]-2'-cyclohexylethyl}-3R,4R)-dimethyl-4-(3-hydroxyphenyl)piperidine (26).

Anal. calcd for $C_{30}H_{42}N_2O_3$: C, 75.28, H, 8.84; N, 5.85. Found: C, 75.18; H, 8.96; N, 5.97.

N-{(2'S)-[3-(4-Hydroxyphenyl)propanamido]-3'-phenylpropyl}-(3R,4R)-dimethyl-4-(3-hydroxyphenyl)piperidine (27).

Anal. calcd for $C_{31}H_{38}N_2O_3$: C, 76.51, H, 7.87; N, 5.76. Found: C, 76.15; H, 7.99; N, 5.89.

Example 2

Figure 8:
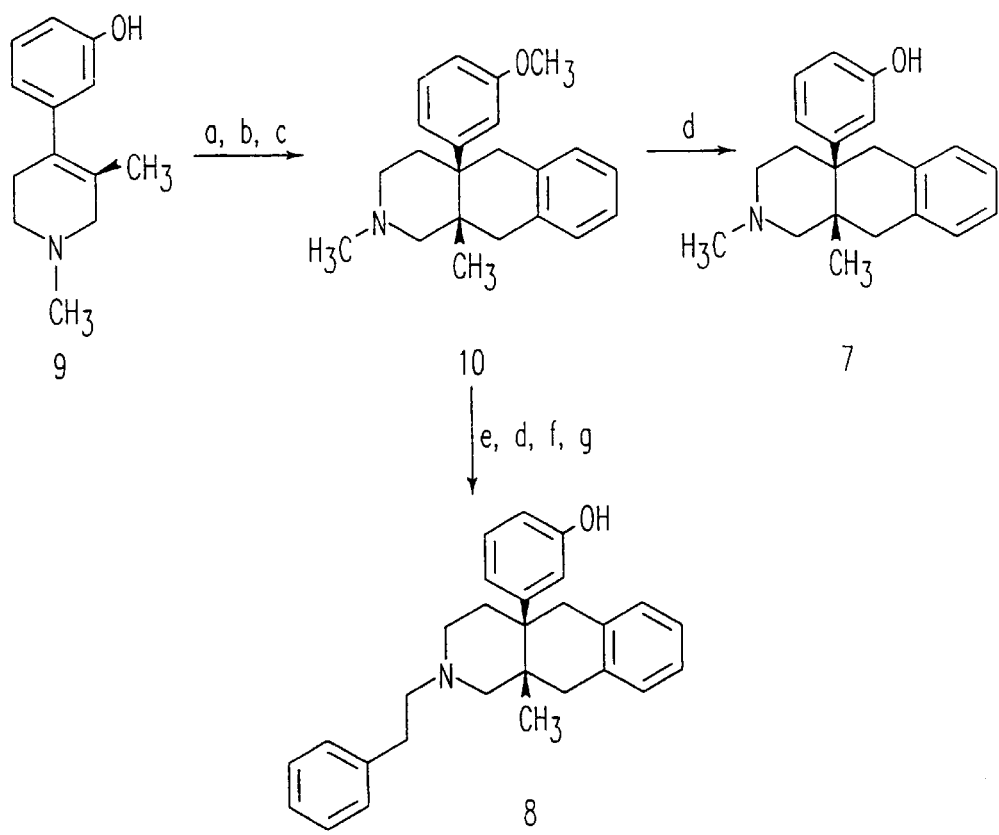
FIG. 8: Synthesis of compounds (7) and (8) as described in Example 2.

N-substituted (±)-1,2,3,4,4a,5,10,10a-Octahydro4a-(3-hydroxyphenyl)-10a-methylbenzo[g]isoquinolines Summary Potent, opioid receptor pure antagonist activity has been demonstrated in the N-substituted (±)-1,2,3,4,4a,5,10,10a-octahydro-4a-(3-hydroxyphenyl)-10a-methylbenzo[g]isoquinolines, 7 and 8 (FIG. 8). These compounds share many of the characteristics identified with the phenylpiperidine antagonists including N-substituent mediated potency and a lack of N-substituent mediated antagonism. Also, like the phenylpiperidines, 7 and 8 display a strong preference for mu and kappa versus delta opioid receptor binding. Unlike the phenylpiperidines however, the benzoisoquinoline system displays a stronger preference for the kappa versus the mu opioid receptor and a lower overall potency relative to typical trans-3,4-dimethyl-4-(3-hydroxyphenyl)piperidine antagonists. Together this data suggests a common site of action within the opioid receptors for compounds 7 and 8 and the trans-3,4-dimethyl-4-(3-hydroxyphenyl)piperidines.

Chemistry

The N-methyl and N-phenethyl derivatives of (±)-1,2,3,4,4a,5,10,10a-octahydro-4a-(3-hydroxyphenyl)-10a-methylbenzo[g]isoquinoline (7 and 8, respectively) were prepared starting from tetrahydropyridine (9) according to the method illustrated in FIG. 8.[1] Accordingly, 9 was deprotonated with sec-butyl lithium followed by alkylation with α,α'-dichloroxylene. This material was not isolated but was immediately cyclized with NaI in refluxing acetonitrile and reduced with sodium borohydride to provide intermediate 10 in 23% yield. The N-methyl derivative (7) was then available via Odemethylation employing refluxing HBr in acetic acid. The N-phenylethyl derivative (8) was prepared from 10 by N-demethylation using phenylchloroformate in refluxing toluene followed by subjecting the crude carbamate to refluxing HBr in acetic acid to cleave the urethane and deprotect the phenol. Conversion of this material to the desired compound (8) was accomplished by coupling with phenyl acetic acid using benzotriazol-1-yl-oxy-tris-(dimethylamino)phosphonium hexafluorophosphate (BOP reagent) followed by reduction of the resulting amides using borane in tetrahydrofuran in 2.2% overall yield.

Results and Discussion

Figure 9A:
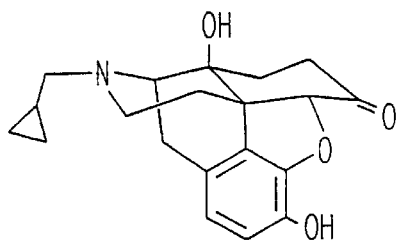
FIG. 9: Structural representation of (a) Naltrexone, (b) 3,4-dimethyl-4-(3-hydroxyphenyl)piperidine, and (c) 8a-methyl-4a-(3-hydroxyphenyl)-octahydrobenzo[e]isoquinoline (Example 2).
Figure 9B:
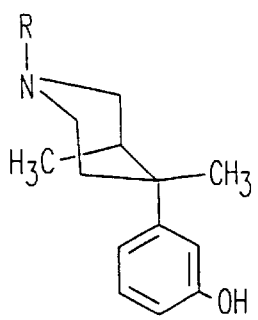
Figure 9C:
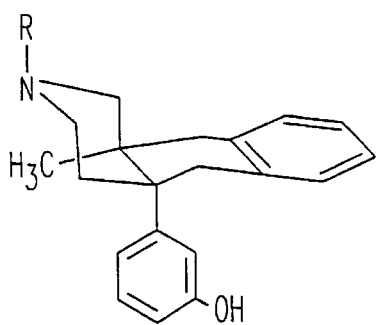

Both initial studies and work conducted in this laboratory have provided strong evidence that the antagonist activity of some N-substituted piperidine compounds is expressed via a phenyl equatorial/piperidine chair receptor-ligand interaction as illustrated in FIG. 9b.[2] This stands in contrast to the phenylaxial/piperidine chair conformation exhibited by naltrexone (FIG. 9a). The benzoisoquinoline system (FIG. 9c), where a bridge connects carbons 3 and 4 in the piperidine ring, was selected for study because its structure could potentially maintain the proposed active conformation of the phenylpiperdines as well as provide sites for further structural elaboration. Compounds 7 and 8 were therefore synthesized and tested in both binding and functional assays to establish the overall effect of this structural change on antagonist activity and potency.

The radioligand binding data for the N-methyl and N-phenethyl derivatives of (±)-1,2,3,4,4a,5,10,10a-octahydro-4a-(3-hydroxyphenyl)-10a-methylbenzo[g]isoquinolines (7 and 8, respectively) are provided in Table 4. For comparison, the radioligand binding assay data for the parent ligands 5 and 6 are given in Table 5.[3] As these data sets are from different assays, the binding data obtained for naltrexone (3) is provided as a reference standard from both sets of assays. Inspection of the data reveals a fundamental shift in the receptor binding preference of the benzoisoquinolines in favor of the kappa receptor relative to the phenylpiperidines which typically show greater potency at the mu receptor. However, the overall preference for mu/kappa binding relative to delta binding is preserved (the phenylpiperidines typically show the least preference for the delta receptor, data not shown). Increasing the size of the N-substituent (conversion of 7 to 8) provides an overall increase in potency at all receptors, a feature shared by conversion of the phenylpiperidine 5 to 6. The latter information together with the general receptor binding preferences suggests that the benzoisoquinoline antagonists probably interact with the same subsites within the opioid receptors as do the phenylpiperidines, but the addition of the 3,4 bridge leads to both an increase in affinity for the kappa receptor as well as a loss of affinity for the mu receptor relative to the phenylpiperidine antagonists.

In the functional assay shown in Table 6, compounds 7 and 8 displayed a pattern of activity consistent with the radioligand binding assay. Thus, inhibition of agonist stimulated [$^{35}$S]GTPγS binding in guinea pig caudate by 7 and 8, a measure of functional antagonist activity,[4] was greatest against U69,593 (kappa receptor) with the potency demonstrated against DAMGO (mu receptor) being only slightly less. The ability to inhibit SNC80 (delta receptor) stimulated [$^{35}$S]GTPγS binding was significantly lower. As in the previous assay, increasing the size of the N-substituent lead to an increase in potency. Importantly, neither the N-methyl derivative 7 nor the N-phenethyl derivative 8 stimulated [$^{35}$S]GTPγS binding when tested at concentrations as high as 1 μM; the benzoisoquinoline structure therefore retains opioid pure antagonist activity.

Figure 10:
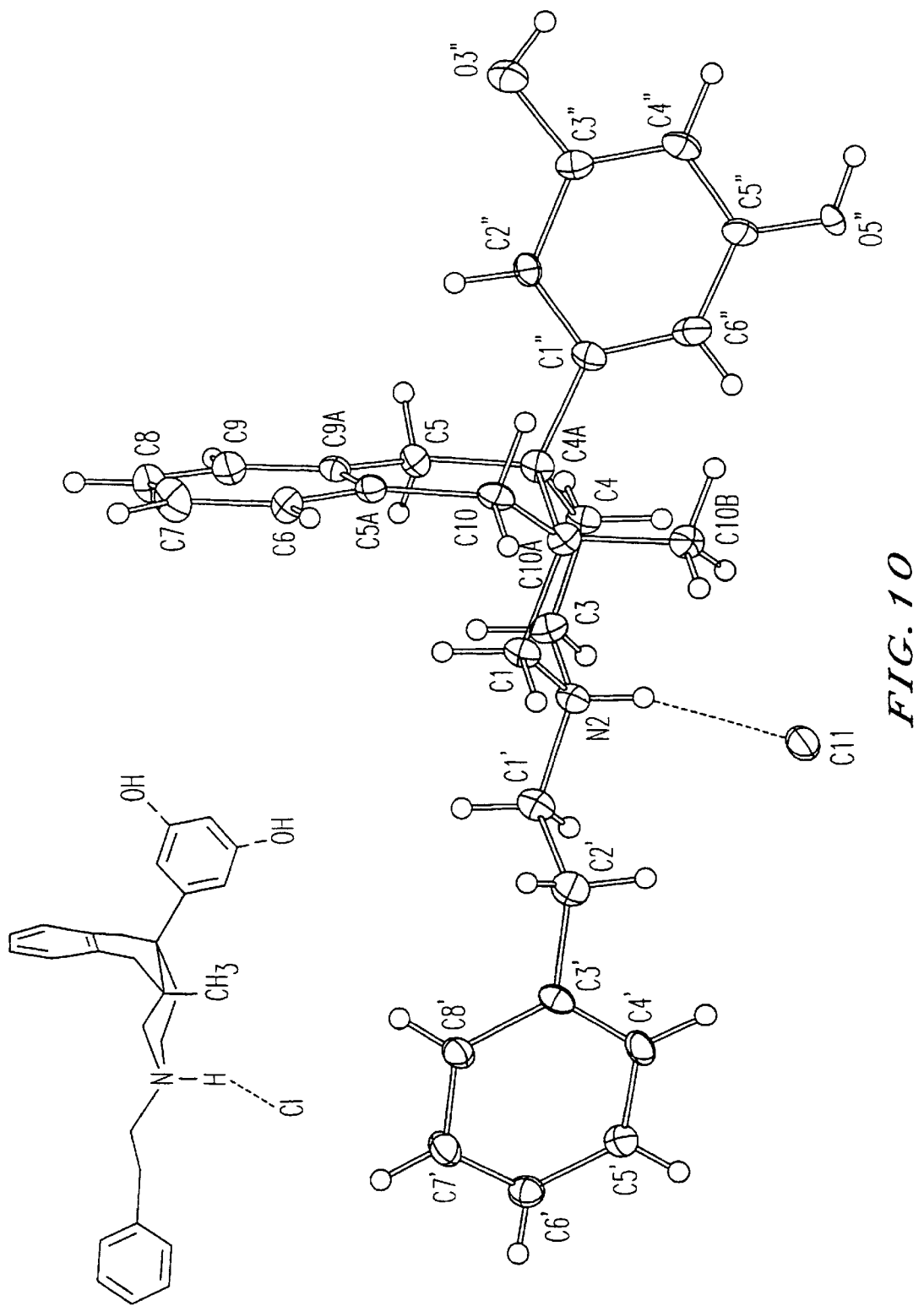
FIG. 10: Structure of (±)-[2-phenethyl-8a-methyl-4a-(3-hydroxymethyl)]octahydrobenzo[e]isoquinoline (8) HCl described in Example 2 by single crystal X-ray analysis.

In terms of potency, both 7 and 8 demonstrate a decreased affinity for all of the opioid receptors relative to some of the more potent phenylpiperidine antagonists. The source of this loss of activity cannot be immediately established since several explanations exist. It is possible that these compounds have greater preference for a phenyl axial/piperidine chair conformation relative to the phenylpiperidines, though it has been found that 8 exists in the phenylequatorial/piperidine chair conformation in the solid state (FIG. 10). More likely, the lower potency results from a lack of activity of one of the enantiomers of 6. Hugh eudismic ratios are observed in most classes of opioid ligands.

In summary, potent opioid receptor pure antagonist activity was demonstrated for (±)-1,2,3,4,4a,5, 10,10a-octahydro-4a-(3-hydroxyphenyl)-2-phenethyl-10a-methylbenzo[g]isoquinoline (8). Compounds 7 and 8 share many of the characteristics identified with the phenylpiperidine antagonists including N-substituent mediated potency and a lack of N-substituent mediated antagonism. Also, these ligands display a strong preference for mu and kappa versus delta binding. Unlike the phenylpiperidines, the benzoisoquinolines display a stronger preference for the kappa versus the mu receptor and a lower overall potency as, a racemic mixture, relative to typical trans-3,4-dimethyl-4-(3-hydroxyphenyl)piperidine antagonists. Together this data suggests both a common site of action within the opioid receptors for compounds 7 and 8 and the trans-3,4-dimethyl-4-(3-hydroxyphenyl)piperidines.

Experimental

Melting points were determined on a Thomas-Hoover capillary tube apparatus and are not corrected. Elemental analyses were obtained by Atlantic Microlabs, Inc. and are within ±0.4% of the calculated values. $^1$H and $^{13}$C NMR were determined on a Bruker WM-250 spectrometer using tetramethylsilane as an internal standard. Radial chromatography was performed on a Harrison Research Chromatotron model 7924T. All reactions were followed by thin-layer chromatography using Whatman silica gel 60 TLC plates and were visualized by UV or by charring using 5% phosphomolybdic acid in ethanol. All solvents were reagent grade. Tetrahydrofuran and diethyl ether were dried over sodium benzophenone ketyl and distilled prior to use. α,α'-Dichloroxylene, purchased from Aldrich Chemical Co., was recrystallized from hexane prior to use.

(±)-1,2,3,4,4a,5,10,10a-octahydro-4a-(3-methoxyphenyl)-2,10a-dimethylbenzo-[g]isoquinoline (10): To a dry three-neck round-bottomed flask was charged 500 mg (2.3 mmol) of tetrahydropyridine (9) (CAUTION: read reference 12 and references cited therein) and 20 mL dry THF. This was cooled to −78° C., and to this was added 2.4 mL (3.12 mmol) s-BuLi (1.3M in cyclohexane) via a syringe over 5 min. The flask was then warmed to −0° C. and aged for 10 min. The flask was then cooled to −78° C. and cannulated into a mixture of 40 ml dry ethyl ether and 1.3 g (7.59 mmol) α,α'-dichloroxylene at −50° C. over 20 min. This was aged for 20 min and then quenched with ice-cold 1N HCl. The contents of the flask were then transferred to a separatory funnel with ice-cold ether-and ice-cold 1N HCl. The aqueous layer was removed and stored in an ice bath while the organic layer was twice extracted with ice-cold 1N HCl. The combined aqueous layers were placed into a new separatory funnel and extracted twice with ice-cold ethyl ether to remove α,α'-diochloroxylene. The aqueous layer was then made basic with 50% NaOH at first and finally saturated NaHCO$_3$ to pH 10. The aqueous layer was then extracted 3 times with ice-cold ethyl ether and then discarded. The ether extracts were dried over K$_2$CO$_3$ and then to filtered into a round-bottom flask and the solvent removed on the rotavap at 0° C. After all of the solvent was removed, the residue was dissolved in 40 mL sieve dried $CH_3CN$, and to this was added 870 mg NaI and 650 mg $K_2CO_3$. The flask was then attached to a reflux condenser and a heating mantle and the system heated under reflux for 3 h. After this time, the flask was cooled to room temperature and filtered. The solvent was then removed on a rotavap and the residue dissolved in 40 mL punctilious ethanol. To this mixture was added 750 mg $NaBH_4$ in one portion and the mixture allowed to stir overnight. On the following day, 1N HCl was added to this mixture until no further evolution of hydrogen was observed. This was stirred for 10 min, and then 50% NaOH and water were added until the mixture was clear and basic. The volatiles were then removed on a rotavap, and the residue was extracted 3 times with 1:1 ethyl ether:ethyl acetate. This was dried over $K_2CO_3$ and $Na_2SO_4$. After filtration and solvent removal, a small portion of the crude residue was dissolved in $CHCl_3$ and spotted on a silica gel plate. Elution with 50% CMA-80 (80 $CHCl_3$:18 MeOH: 2 $NH_4OH$) in $CHCl_3$ revealed a compound in the mixture that gave a pale spot when dipped in 5% PMA in EtOH at about 0.75 Rf. This is the tertiary amine product. No other tertiary amines were observed in the mixture. $^1H$ NMR of the crude mixture revealed the desired product as well as starting material (9) and other undesired products. Chromatography on silica gel using 12.5% CMA-80 in $CHCl_3$ gave the desired product in the early fractions just behind the solvent front but not in the solvent front. This gave 115 mg of the desired product as a slightly yellow oil. Yield 15.5%.

$^1H$ NMR ($CDCl_3$) δ 0.993 (s, 3H); 1.404 (ddd, 1H, J=13.7, 2.6, 2.6 Hz); 2.149 (d, 1H, J=11.6 Hz); 2.229 (d, 1H, J=17.0 Hz); 2.240 (s, 3H); 2.310 (dd, 1H, J=11.6, 1.5 Hz); 2.379 (ddd, 1H, J=12.1, 12.1, 3.2 Hz); 2.646 (d, 1H, J=17.0 Hz); 2.862 (dd, 1H, J=13.7, 4.7 Hz); 2.885 (d, 1H, J=18.3 Hz); 2.962 (m, 1H); 3.570 (d, 1H, J=18.3 Hz); 3.634 (s, 3H); 6.715 (ddd, 1H, J=8.1, 2.5, 0.9 Hz); 6.839 (m, 2H); 7.048 (d, 1H, J=7.6 Hz); 7.197–7.080 (m, 4H). $^{13}C$ NMR ($CDCl_3$) δ 158.9, 148.9, 135.9, 135.6, 128.6, 128.36, 128.0, 125.9, 125.5, 120.0, 113.9, 110.8, 64.04, 54.9, 52.2, 46.6, 40.6, 40.11, 35.98, 31.5, 24.4.

(±)-1,2,3,4,4a,5,10,10a-octahydro-4a-(3-hydroxyphenyl)-2,10a-dimethylbenzo-[g]isoquinoline (7): To a 10 mL single-necked flask was added 100 mg (0.31 mmol) of (±)-1,2,3,4,4a,5,10,10a-octahydro-4a-(3-methoxyphenyl)-2,10a-dimethylbenzo[g]isoquinoline (10) and 0.8 mL of glacial acetic acid and 0.8 mL of 48% HBr. This mixture was heated under reflux for 18 h and then cooled to room temperature. The pH was then adjusted to 10 with cooling starting with 50% NaOH and finishing with saturated $NaHCO_3$. This was extracted 2 times with $CHCl_3$ and 2 times with 3:1 n-butanol:toluene. Both extracts were dried over $K_2CO_3$, and then the solvent was removed. The material from both extracts was examined by $^1H$ NMR and was shown to contain the desired product. The material from the $CHCl_3$ layer was chromatographed on silica gel eluting with 25% CMA-80 in $CHCl_3$. This gave 27 mg of the desired product (7) (28% yield). The residue was dissolved in MeOH, and to this was added 3 equivalents of 1N HCl in dry ethyl ether. The solvents were removed, and the residue crystallized from ether/MeOH. The butanol extracts contained 45 mg of the desired material giving an overall yield of 74.6%. MP ° C. 270–275 (dec). Anal. Calcd for $C_{21}H_{26}NOCl·0.25H_2O$: C, 65.54; H, 7.20; N, 3.64. Found: C, 65.86; H, 7.15; N, 3.42. $^1H$ NMR (DMSO) δ 1.014 (s, 3H); 1.587 (d, 1H, J=14.3 Hz); 2.072 (s, 3H); 2.358 (d, 1H, J=17.4 Hz); 2.498 (d, 1H, J=17.4 Hz); 2.734 (s, 3H); 2.924–2.792 (m, 3H); 3.113 (d, 1H, J=13.1 Hz); 3.602 (d, 1H, J=18.78 Hz); 6.562 (d, 1H, J=8.0 Hz); 6.611 (m, 2H); 6.993 (t, 1H, J=7.5 Hz); 7.081 (d, 1H, J=7.5 Hz); 7.148 (t, 1H, J=7.8 Hz); 7.269–7.193 (m, 2H); 9.30 (s, 1H); 9.898 (bs, 1H). $^{13}C$ NMR (DMSO) δ 156.7, 146.4, 135.5, 133.3, 128.5, 128.4, 128.2, 126.2, 125.7, 117.6, 114.3, 113.5, 59.2, 49.4, 38.6, 35.4, 35.2, 31.0, 28.7, 22.8.

(±)-1,2,3,4,4a,5,10,10a-octahydro-4a-(3-hydroxyphenyl)-2-phenethyl-10a-methylbenzo[g]isoquinoline (8): To 300 mg (0.93 mmol) intermediate (10) was added 5 mL dry toluene followed by heating to 80° C. To this was added 0.23 mL (1.86 mmol) distilled phenylchloroformate dropwise via syringe. A precipitate formed, and the mixture was heated at reflux for 5 h. The mixture was cooled to room temperature and washed 3 times with 1N NaOH and dried over sodium sulfate. $^1H$ NMR of the crude mixture indicated that no starting material was present (no N-methyl signal at 2.25 ppm). The crude mixture was then dissolved in 4 mL glacial acetic acid and 4 mL 48% HBr. This was heated at reflux for 18 h followed by addition of water and methyl t-butyl ether (MTBE). The aqueous layer was removed and extracted two more times with MTBE to remove phenol. The aqueous layer was then pH adjusted to 10 using 50% NaOH and saturated sodium bicarbonate and extracted 3 times with 3:1 methylene chloride:tetrahydrofuran (THF) and the organic layer dried over sodium sulfate. Following removal of solvent, this highly polar material was dissolved in 15 mL THF, and to this was added 442 mg (1 mmol) BOP reagent, 0.4 mL triethylamine (2.2 mmol), and 136 mg (1 mmol) phenyl acetic acid. This was stirred for 3 h and then diluted with ethyl ether, 40 mL, and washed sequentially with 15 mL water, 1N HCl, saturated sodium bicarbonate, and brine. The solution was dried over sodium sulfate and the solvent removed on a rotary evaporator. The material was then dissolved in chloroform and filtered through silica gel to remove highly colored polar impurities to give 142 mg relatively clean material. $^1H$ NMR of this crude material indicated the presence of rotamers typical of piperidine amides and urethanes. Reduction of this compound was accomplished by dissolving in dry THF followed by addition of 1.16 mL of 2M borane dimethylsulfide in THF. After heating for 3 h, the mixture was cooled to room temperature, and 2 mL methanol was added and stirred for 1 h. After this time, 1.16 mL 1N HCl in ether was added and stirred for 1 h. The solvent was then removed on a rotary evaporator and the crude mixture dissolved in chloroform, saturated sodium bicarbonate, and water. The pH was adjusted to 10 and the organic layer washed 3 times with water and then dried over sodium sulfate. The crude residue was chromatographed on silica gel using 0–10% MeOH in chloroform as eluent, and this material was crystallized from MeOH/ether as its HCl salt to give 55.8 mg of the desired material (0.137 mmol) or 2.2% overall yield. MP ° C. 255–265 (dec). Anal. Calcd for $C_{28}H_{32}NOCl·0.5H_2O$: C, 75.91; H, 7.51; N, 3.16. Found: C, 75.93; H, 7.53; N, 3.17. $^1H$ NMR (DMSO) δ 10.06 (br s, 1H); 9.34 (s, 1H); 7.30 (dd, 2H, J=8.1 Hz, 8.1 Hz); 7.22 (m, 5H); 7.15 (dd, 1H, J=7.7 Hz, 7.7 Hz); 7.08 (d, 1H, J=7.7 Hz); 6.63 (s, 1H); 6.62 (d, 1H, J=8.1 Hz); 6.55 (d, 1H, J=8.1 Hz); 3.59 (d, 1H, J=18.9 Hz); 3.50 (d, 1H, J=12.1 Hz); 3.32 (m, 4H); 3.11 (ddd, 1H, J=5.1 Hz, 12.1 Hz, 12.1 Hz); 3.02 (ddd, 1H, J=5.1 Hz, 12.1 Hz, 12.1 Hz); 2.87 (m, 3H); 2.50 (d, 1H, J=17.4); 2.42 (d, 1H, J=17.4); 1.62 (d, 1H, J=14.3); 1.08 (s, 3H). $^{13}C$ NMR (DMSO) δ 156.72, 146.44, 137.23, 135.45, 133.38, 128.63, 128.59, 128.56, 128.52, 128.19, 126.71, 126.39, 125.72, 117.55, 114.33, 113.51, 57.27, 57.18, 48.22, 39.46, 38.66, 35.40, 35.21, 29.45, 28.59, 23.06.

REFERENCES (1) Evans, D. A.; Mitch, C. H.; Thomas, R. C.; Zimmerman, D. M.; Robey, R. L. Application of metalated enamines to alkaloid synthesis. An expedient approach to the synthesis of morphine-based analgesics. *J. Am. Chem. Soc.* 1980, 102, 5955–5956. WARNING: Read the background information relating to analogs of MPTP (i.e., 9) including Zimmerman et al., *J. Med. Chem.*, 1986, 29, 1517–1520, and references cited therein.

(2) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence*,1978, pp. 237–247.

(3) Mitch, C. H.; Leander, J. D.; Mendelsohn, L. G.; Shaw, W. N.; Wong, D. T.; Zimmerman, D. M.; Gidda, S. J.; Cantrell, B. E.; Scoepp, D. D.; Johnson, B. G.; Leander, J. D. *J. Med. Chem.* 1994, 37, 2262–2265.

(4) Xu, H.; Lu, Y.-F.; Partilla, J. S.; Brine, G. A.; Carroll, F. I.; Rice, K. C.; Lai, J.; Porreca, F.; Rothman, R. B. Opioid peptide receptor studies. 6. The 3-methylfentanyl congeners RTI4614-4 and its enantiomers differ in efficacy, potency, and intrinsic efficacy as measured by stimulation of [$^{35}$S]GTP-$\gamma$-S binding using cloned $\mu$-opioid receptors. *Analgesia* 1997, 3, 35–42.

TABLE 4

Radioligand Binding Results in Mu, Delta, and Kappa Opioid Receptor Assays

| Compound | [$^3$H]DAMGO[a] | [$^3$H]DADLE[b] | [$^3$H]U69,593[c] |
|---|---|---|---|
| | $K_i$ (nM ± SD) | | |
| 7 | 297 ± 23 | >5710 | 166 ± 15 |
| | (1.02 ± 0.07) | | (0.87 ± 0.06) |
| 8 | 11.2 ± 2.7 | 1270 ± 106 | 9.8 ± 1.7 |
| | (0.56 ± 0.07) | (1.14 ± 0.099) | (0.69 ± 0.07) |
| 3, naltrexone | 1.39 ± 0.40 | 94.9 ± 6.6 | 4.71 ± 0.12 |
| | (0.94) | (1.01) | (1.05) |

[a][$^3$H]DAMGO [(D-Ala$^2$,MePhe$^4$,Gly-ol$^5$)enkephalin]. Tritiated ligand selective for mu opioid receptor.
[b][$^3$H]DADLE [(D-Ala$^2$,D-Leu$^5$)enkephalin]. Tritiated ligand selective for delta opioid receptor.
[c][$^3$H]U69,593 (trans-3,4-dichloro-N-methyl[2-(1-pyrrolidinyl)cyclohexyl]benzeneacetamide). Tritiated ligand selective for kappa opioid receptor.

TABLE 5

Affinities of the 4-Phenylpiperidine Antagonists for the $\mu$ and $\kappa$ Opioid Receptors[a]

| Compd | [$^3$H]Nal[b] | [$^3$H]EKC[c] |
|---|---|---|
| | $K_i$ (nM) | |
| 5 | 80 | 833 |
| 6 | 1.5 | 52 |
| 3, naltrexone | 0.56 | 3.9 |

[a]Data taken from reference 3.
[b]Naloxone ($\mu$ receptor assay).
[c]Ethylketocyclazocine ($\kappa$ receptor assay).

TABLE 6

Inhibition by Antagonists of [$^{35}$S]GTP$\gamma$S Binding in Guinea Pig Caudate Stimulated by the Opioid Receptor Subtype-Selective Agonists, DAMGO ($\mu$), SNC80 ($\delta$), and U69,593 ($\kappa$).

| Compound | DAMGO | SNC80[a] | U69,593 |
|---|---|---|---|
| | $K_i$ (nM ± SD) | | |
| | (N) | | |
| 7 | 119 ± 7.93 | 222 ± 30.7 | 52.60 ± 6.38 |
| | (0.94 ± 0.06) | (0.78 ± 0.09) | (1.10 ± 0.14) |
| 8 | 10 ± 0.91 | 184 ± 24.3 | 6.61 ± 0.57 |
| | (0.89 ± 0.06) | (0.78 ± 0.09) | (1.01 ± 0.08) |
| 1, naltrexone | 0.930 ± 0.21 | 19.3 ± 2.25 | 2.05 ± 0.21 |
| | (1.00 ± 0.22) | (1.13 ± 0.14) | (0.76 ± 0.05) |

[a]SNC80 ([(+)-4-[($\alpha$R)-$\alpha$-(2S,5R)-4-allyl-2,5-dimethyl-1-piperazinyl)-3-methoxybenzyl]-N,N-diethylbenzamide]). Agonist selective for delta opioid receptor.

This Example is described in Thomas et al, Bioorganic and Medicinal Chemistry Letters 8 (1998) 3149–3152, incorporated herein by reference.

Example 3

Opioid Receptor Antagonists

Summary

Two sets of novel opioid receptor antagonist pharrnacophores have been prepared and demonstrated from a model of opioid antagonist binding. One is based on a rigid 5-phenylmorphan nucleus and the other on a more flexible benzoisoquinoline nucleus. Using modifications of these systems and by comparisons with the related trans-3,4-dimethyl-4-(3-hydoxyphenyl)piperidines, provides strong evidence supporting the hypothesis that this class of antagonist binds the opioid receptors in a phenyl equatorial mode and that the trans-3-methyl substituent (phenyl piperidine numbering) is an important element for conversion of agonists into antagonists.

Chemistry

Figure 11:
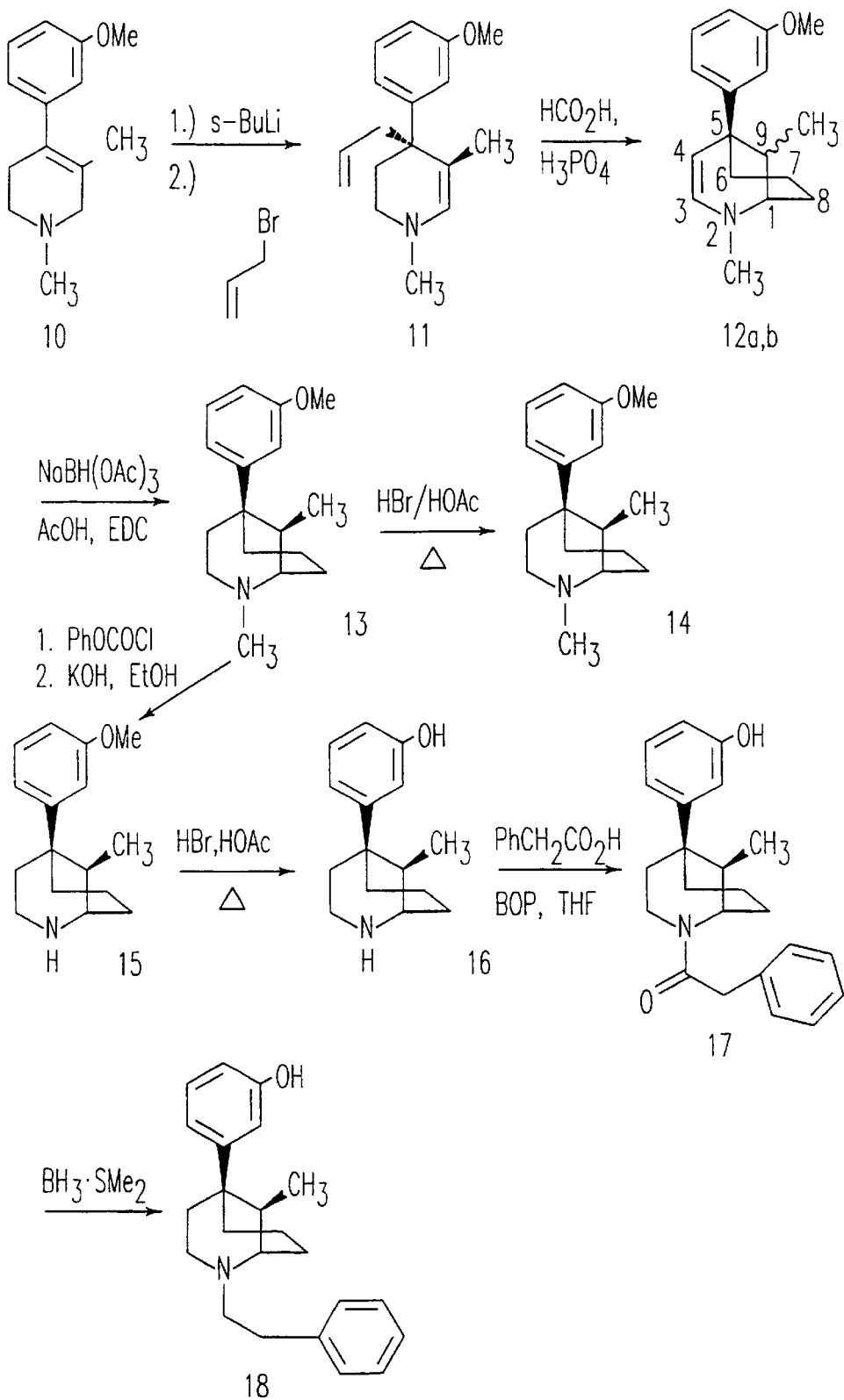
FIG. 11: Synthesis of compound (18) as described in Example 3.

The $\beta$-5-(3-hydroxyphenyl) morphans were prepared by the method shown in FIG. 11. Deprotonation of the known compound 10 with sec-butyl lithium followed by alkylation with allyl bromide cleanly provided intermediate 11 in quantitative yield. This compound was then cyclized provide 12 in 90% yield as a 2.5:1 mixture of diastereomers. Further experimentation established conditions which changed the ratio of 12a:12b to 10:1. Compounds 13a,b were then readily available via enamine reduction followed by separation using radial chromatography. The major isomer 13 was then O-demethylated to give 14. Since elucidation of the stereochemistry was not straightforward using NMR techniques, crystals of the HCl salt of 14 are shown by X-ray analysis to possess the desired 9$\beta$-methyl stereochemistry.

Compound 13 was also converted to the N-phenylethyl compound 18. N-Demethylation of 13 gave 15 which on O-demethylation yielded 16. Compound 16 was then converted to the N-phenethyl derivative (18) by the two step procedure involving coupling of 16 with phenylacetic acid followed by borane-dimethylsulfide reduction of the intermediate amide 17.

Figure 12:
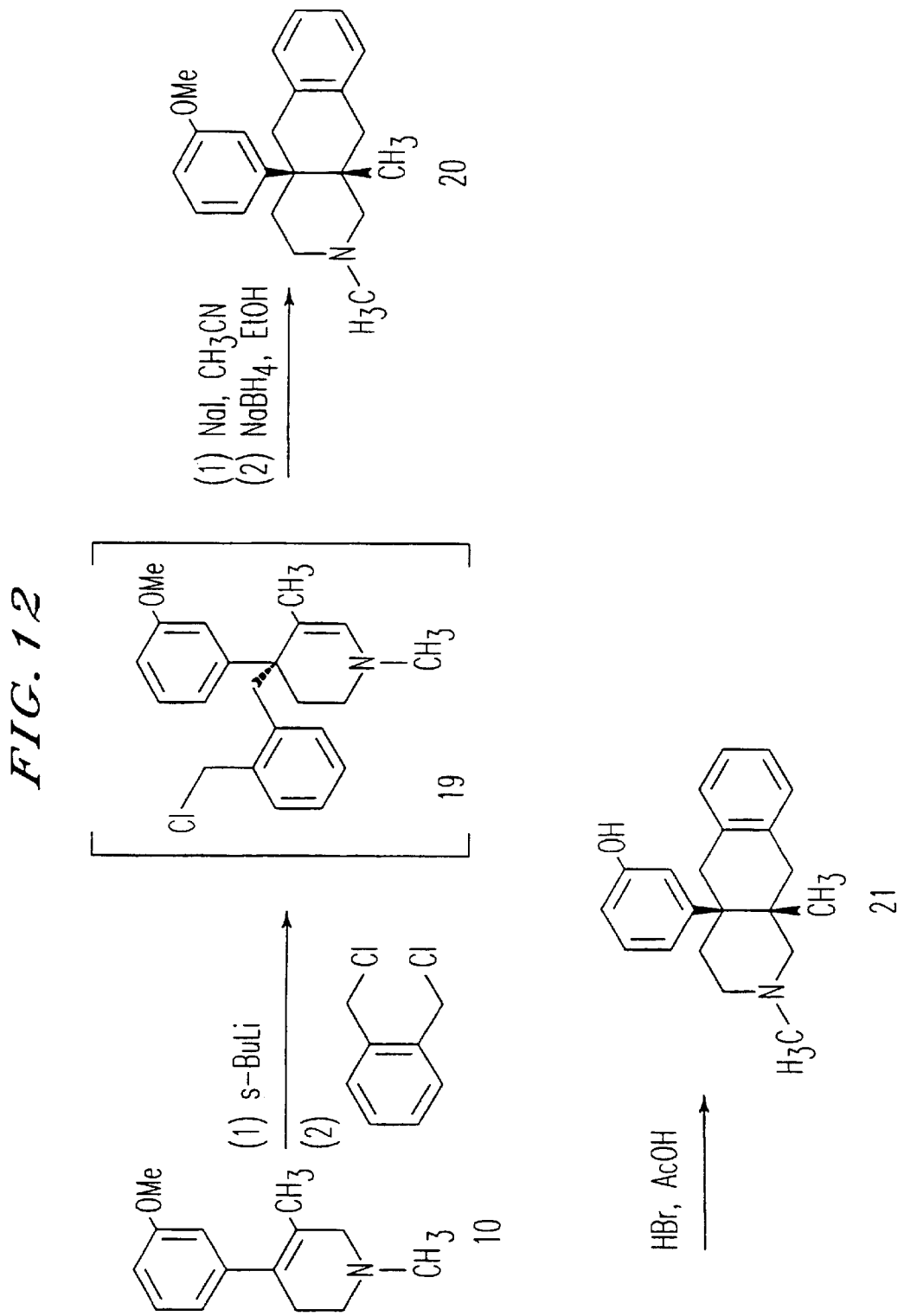
FIG. 12: Synthesis of compound (21) as described in Example 3.

The benzoisoquinoline compound (20) was also prepared starting from compound 10 according to the method illustrated in FIG. 12. Accordingly, 10 was deprotonated with sec-butyl lithium followed by alkylation with $\alpha,\alpha'$-dichloroxylene to give intermediate 19 which was not isolated but was immediately cyclized with NaI and reduced to provide compound 20 in 13% yield. O-Demethylation of 20 using hydrogen bromide in acetic acid yielded 21. The structure was established using a combination of NMR techniques.

Biological Assay Results

The new compounds 14, 18, and 21 were shown to bind the opioid receptors and also were shown to be pure antagonists. The data supporting these conclusions is presented in Tables 7 and 8.

Discussion

The radioligand binding data in Table 7 show that compounds 14, 18, and 21 have affinity for the opioid receptors. 18 is more potent than 14. The data in Table 8 shows that all three compounds are pure antagonists.

Experimental

All of the solvents used were reagent grade with the exception of diethyl ether and THF in reactions and these were distilled from sodium/benzophenone ketyl. NMR spectra were collected on both a 250 MHz and a 500 MHz Bruker spectrometer. The melting points reported below are uncorrected.

1,2,3,4-Tetrahydro-4-allyl-1,5-dimethyl-4-(m-methoxyphenyl)pyridine (5): To a solution of 500 mg (2.3 mmol) of tetrahydropyridine10 in 15 mL of THF at −42° C. was added s-BuLi in cyclohexane (1.3M, 2.9 mmol). After 1 h, allyl bromide (2.3 mmol) was added, and the color of the solution changed from dark red to yellow. After been stirred for 1 hour at −42° C., the mixture was allowed to warmed to 0° C. and then quenched with water (10 mL). Diethyl ether (10 mL) was added and the aqueous layer was extracted with ether (2×). The combined ether layers were washed with water (10 mL), saturated $NaHCO_3$, brine and dried over $Na_2SO_4$. Evaporation of solvent afforded 590 mg (~100%) of crude 11. The crude product was used directly in the next step without further purification. $^1$H NMR ($CDCl_3$) δ 7.26 (m, 1H), 7.01 (m, 2H), 6.74 (m, 1H), 5.89 (s, 1H), 5.82 (m, 1H), 5.13 (m, 2H), 3.80 (s, 3H), 2.68–2.40 (m, 3H), 2.55 (s, 3H), 2.22 (m, 1H), 1.66 (m, 2H), 1.52 (s, 3H). $^{13}$C NMR ($CDCl_3$) δ 159.2, 151.1, 136.7, 135.8, 128.7, 119.8, 117.4, 114.3, 110.1, 107.7, 55.1, 46.1, 43.1, 43.0, 41.7, 36.4, 17.3.

(1S*,5R*,9R*/S*)-2,9-Dimethyl-5-(m-methoxyphenyl)-2-azabicyclo[3,3,1]non-3-ene (12a/b): A solution of 300 mg (1.17 mmol) of 11 in 6 mL of 85% $H_3PO_4/HCO_2H$ (1:1) was stirred at room temperature for 72 h. The resulting dark brown mixture was diluted with water (6 mL) and cooled in ice bath while NaOH (25% w/w) was added until pH-8. The aqueous solution was extracted with $CHCl_3$ (3×). The combined organic layers was washed with aqueous $NaHCO_3$ and brine and dried over $Na_2SO_4$. Evaporation of the solvent gave 270 mg (90%) of crude products 12a and 12b in a ratio of 2.5:1. The crude products were used directly in the next step without further purification. $^1$H NMR ($CDCl_3$) of the mixture: δ 7.24–6.70 (m, 4H), 6.16 (d, 1H, J=9.2 Hz), 4.34 (d, 1H, J=7.0 Hz), 4.13 (d, 1H, J=9.1 Hz), 3.80 (s, 3H), 2.80 (s, 3H), 3.10–1.40 (m, 8H), 0.74 (d, 3H, J=8.6 Hz), 0.57 (d, 3H, J=8.1 Hz).

(1S*,5R*,9R*/S*)-2,9-Dimethyl-5-(m-methoxypenyl)-2-azabicyclo[3,3,1]nonane (13a/b): A solution of 270 mg (1.05 mmol) of 12a and 12b mixture and acetic acid (1.05 mmol, 0.061 mL) in 5 mL of dichloroethane was treated with $NaBH(OAc)_3$ under $N_2$ atmosphere. The reaction was stirred at room temperature for 2 h. The reaction was quenched by adding 10% NaOH to pH ~10. The mixture was extracted with ether (3×), washed with water and brine. The organic phase was dried over $Na_2SO_4$ and concentrated under reduced pressure. Separation by chromatography (1% Et3N/EtOAc) gave 135 mg (50%) of 13a and 60 mg (22%) of 13b as colorless oils. $^1$H NMR ($CDCl_3$) of 8: δ 7.26 (m, 1H,), 6.94 (m, 2H), 6.70 (m, 1H), 3.80 (s, 3H), 3.05–2.90 (m, 2H), 2.71 (m, 1H), 2.43 (s, 3H), 2.42–2.30 (m, 2 H), 2.28–2.15 (m, 1H), 2.00–1.35 (m, 6H), 0.86 (d, 3H, J=8.25 Hz). $^1$H NMR ($CDCl_3$) of 9: δ 7.23 (m, 1H,), 6.96 (m, 2H), 6.72 (m, 1H), 3.81 (s, 3H), 3.10–2.98 (m, 2H), 2.90 (m, 1H), 2.75 (m, 1H), 2.50 (s, 3H), 2.47 (m, 1H), 2.30–2.06 (m, 2H), 2.05–1.95 (m, 2H), 1.90–1.50 (m, 4H), 0.75 (d, 3H, J=8.56 Hz). $^{13}$C NMR ($CDCl_3$) of 8: 159.2, 152.0, 128.9, 118.0, 112.3, 109.6, 59.7, 55.1, 51.1, 43.1, 42.5, 40.0, 38.3, 29.1, 25.6, 23.4, 14.8. Anal. Calcd for $Cl_7H_{25}NO$: C, 78.72; H, 9.71; N, 5.40. Found: C, 78.79; H, 9.75; N, 5.34.

(1S*,5R*,9R*)-2,9-Dimethyl-5-(m-hydroxyphenyl)-2-azabicyclo[3,3,1]nonane(14): Compound 13a was treated with 4 mL of glacial acetic acid and 4 mL of 48% aqueous hydrobromic acid at reflux temperature for 20 h. The reaction was cooled to room temperature and diluted with 10 mL of water. The pH was adjusted to 10 by using 50% NaOH with ice cooling. The product was extracted into a mixture of 3:1 1-butanol/toluene, dried over $Na_2SO_4$, and concentrated under reduced pressure. Separation by chromatography (1/2 CMA 80) provided 199 mg (84%) of 10 as a white solid. $^1$H NMR ($CDCl_3$) δ 7.15 (m, 1H,), 6.87–6.75 (m, 2H), 6.61 (m, 1H), 3.10–2.90 (m, 2H), 2.77 (m, 1H), 2.44 (s, 3H), 2.50–2.30 (m, 2H), 2.25–2.10 (m, 1H), 2.00–1.60 (m, 5H), 1.60–1.40 (m, 1H), 0.80 (d, 3H, J=8.3 Hz). $^{13}$C NMR (CDCl3) δ 155.9, 152.0, 129.1, 117.5, 113.0, 112.4, 59.7, 51.0, 443.0, 42.0, 40.2, 38.0, 29.0, 25.6, 23.2, 14.6. Anal. Calcd for $C_{16}H_{23}NO\cdot HCl$: C, 68.19; H, 8.53; N, 4.97. Found: C, 68.25; H, 8.53; N, 5.03. The structure of this compound was determined by single crystal X-ray analysis.

(1S*,5R*,9R*)-5-(m-Hydroxyphenyl)-9-methyl 2-azabicyclo[3,3,1]nonane (15): A solution of 200 mg (1.28 mmol) of phenyl chloroformate was added dropwise to 300 mg (1.16 mmol) of 13a in 10 mL of dichloromethane at room temperature under a nitrogen atmosphere. The reaction was refluxed for 6 h. Since the reaction was not complete by TLC, the solvent was then changed to dichloroethane and the reflux was continued for another 12 h. The mixture was cooled to room temperature and concentrated under reduced pressure. The resulting oil was treated with 10 mL of 1N NaOH and stirred with slight warming for 15 min. The product carbamate was then extracted with ether, and the ether layer was washed with 1N HCl and water. The organic phase was dried over $Na_2SO_4$ and concentrated under reduced pressure. The residue was then treated with 5 mL of ethanol and 1.5 mL of 50% aqueous KOH at reflux for 70 h. The mixture was cooled and concentrated under reduced pressure. The resulting concentrate was extracted with ether (2×), and the ether layers were concentrated in vaccuo. The resulting oil was dissolved into 10 mL of 1 N HCl and washed with ether. The aqueous layer was then made strongly basic (pH>12) with 50% NaOH with ice cooling. The desired amine 15 was extracted into ether (2×), and the ether extracts were washed, dried over $Na_2SO_4$, and concentrated under reduced pressure to give 207 mg (70%) of crude 11 as light yellow oil. The crude compound 15 was treated with 4 mL of glacial acetic acid and 4 mL of 48% aqueous hydrobromic acid at reflux temperature for 20 h. The reaction was cooled to room temperature and diluted with 10 mL of water. The pH was adjusted to 10 by using 50% NaOH with ice cooling. The product was extracted into a mixture of 3:1 1-butanol/toluene, dried over $Na_2SO_4$, and concentrated under reduced pressure to yield 100 mg (51%) of 16 as a semi solid. The crude product 16 was used directly in the next step without further purification. $^1$H NMR ($CD_3OD$) δ 7.15 (m, 1H,), 6.79–6.75 (m, 2H), 6.65 (m, 1H), 3.70–3.30 (m, 3H), 2.70 (m, 1H), 2.45–1.70 (m, 8H), 0.87 (d, 3H, J=8.3 Hz).

(1S*,5R*,9R*)-5-(m-Hydroxyphenyl)-9-methyl-2-[(phenylmethyl)carbonyl]-2-azabicyclo[3,3,1]nonane (17): To a solution of 100 mg (0.43 mmol) of 16 and 190 mg (0.43 mmol) of BOP reagent and 0.19 mL (1.38 mmol) of triethylamine in 15 mL of THF was added phenylacetic acid (70.25 mg, 0.52 mmol). The mixture was stirred at room temperature for 1 h. The reaction was diluted with 10 mL of water and ether (10 mL). The aqueous layer was extracted with ether (2×). The combined ether layers were washed with NaHCO$_3$ and brine, and dried over Na$_2$SO$_4$. Evaporation of solvent provided the crude product 17 as a colorless is oil.(A spectrum of $^1$H NMR was attached but the NMR data was not interpreted here due to the rotamers).

(1S*,5R*,9R*)-5-(m-Hydroxyphenyl) 9-methyl-2-(2'-phenylethyl)-2-azabicyclo-[3,3,1]nonane (18): The crude amide 17 was dissolved in THF (8 mL). The solution was cooled to 0° C., and Borane:methyl sulfide complex (0.4 mL, 0.8 mmol) was added dropwise. After vigorous reaction ceased, the resulting mixture was slowly heated to reflux and maintained at that temperature for 4 h. The reaction mixture was cooled to 0° C., 6 mL of methanol was added, and the mixture was stirred for r 1 h. Anhydrous hydrogen chloride in ether (1 mL) was added to attain a pH<2, and the resulting mixture was gently refluxed for 1 h. After the mixture was cooled to room temperature, methanol was added and the solvents were removed on a rotovapor. The residue obtained was made basic (pH>12) by adding 25% NaOH and extracted with ether (3×). The combined ether layers were dried over Na$_2$SO$_4$ and concentrated under reduced pressure. Separation by chromatography (1% Et$_3$N/50% EtOAc/hexanes) gave 38 mg (71%) of amine 18 as a colorless oil. $^1$H NMR (CDCl$_3$) δ 7.30–7.14 (m, 6H), 6.85 (m, 2H), 6.63 (m, 1H), 4.71 (br s, 1H), 3.05 (m, 2H), 2.88 (m, 1H), 2.79 (s, 4H), 2.43–2.15 (m, 3H), 1.94–1.65 (m, 5H), 1.65–1.45 (m, 1H), 0.83 (d, 3H, J=8.2 Hz). $^{13}$C NMR (CDCl3) δ 155.7, 152.5, 140.9, 129.1, 128.8, 128.3, 125.9, 117.7, 113.0, 112.4, 57.4, 57.2, 49.5, 42.4, 40.0, 38.7, 34.1, 29.1, 26.2, 23.4, 14.7. Anal. Calcd for C$_{23}$H$_{29}$NO.HCl: Calcd: C, 74.27; H, 8.13; N, 3.77. Found: C, 74.16; H, 8.12; N, 3.71.

(±)-(2,8a)-Dimethyl-4a-(3-Methoxyphenyl)-Octahydrobenzo[e] Isoquinoline(19): To a dry three neck round bottomed flask was charged 500 mg(2.3 mmol) of 10 and 20 mL dry THF. This was cooled to –78° C. and to this was added 2.4 mL (3.12 mmol) s-BuLi (1.3M in cyclohexane) via a syringe over 5 minutes. The flask was then warmed to –20° C. and aged for 30 min. The flask was then cooled to –78° C. and cannulated into a mixture of 40 mL dry ethyl ether and 1.3 g (7.59 mmol) a, a'-dichloro xylene at –50° C. over 20 min. This was aged for 20 min. and then quench with ice-cold 1N HCl. The contents of the flask were then transfered to a separatory funnel with ice-cold ether and ice-cold IN HCl. The aqueous layer was removed and stored in an ice bath while the organic layer was twice extracted with ice-cold 1N HCl. The combined aqueous layers were placed into a new separatory funnel and extracted twice with ice-cold ethyl ether. The aqueous layer was then made basic with 50% NaOH at first and finally sat'd NaHCO$_3$ to pH 10. The aqueous layer was then extracted 3 times with ice-cold ethyl ether and then discarded. The ether extracts were dried over K$_2$CO$_3$ and then filtered into a round bottom flask and the solvent removed on the rotavap at 0° C. After all of the solvent was removed, the residue was dissolved in 40 mL seive dried CH$_3$CN and to this was added 870 mg NaI and 650 mg K$_2$CO$_3$. The flask was then attached to a reflux condenser and a heating mantle and the system heated under reflux for 3 hours. After this time, the flask was cooled to room temperature and filtered. The solvent was then removed on a rotavap and the residue dissolved in 40 mL punctilious ethanol. To this mixture was added 750 mg NaBH$_4$ in one portion and the mixture allowed to stir overnight. On the following day, 1N HCl was added to this mixture until no further evolution of hydrogen was observed. This was stirred for 10 min and then 50% NaOH and water were added until the mixture was clear and basic. The volatiles were then removed on a rotavap and the residue was extracted 3 times with 1:1 ethyl ether: ethyl acetate. This was dried over K$_2$CO$_3$ and Na$_2$SO$_4$. After filtration and solvent removal, a small portion of the crude residue was dissolved in CHCL$_3$ and spotted on a silica gel plate. Elution with 50% CMA-80 in CHCL$_3$ revealed a compound in the mixture that gave a pale spot when dipped in 5% PMA in EtOH at about 0.75 Rf. This is the 3° amine product. No other 3° amines were observed in the mixture. $^1$H NMR of the crude mixture revealed the desired product as well as starting material 10 and other undesired products. Chromatography on silica gel using 12.5% CMA-80 in CHCL$_3$ gave the desired product in the early fractions just behind the solvent front but not in the solvent front. This gave 115 mg of the desired product as a slightly yellow oil. Yield 15.5%.

$^1$H NMR (CDCl$_3$): δ 0.993 (s, 3H); 1.404 (ddd, 1H, J=13.7, 2.6, 2.6Hz); 2.149 (d, 1H, J=11.6 Hz); 2.229 (d, 1H, J=17.0 Hz); 2.240 (s, 3H); 2.310 (dd, 1H, J=11.6, 1.5 Hz); 2.379 (ddd, 1H, J=12.1, 12.1, 3.2 Hz); 2.646 (d, 1H, J=17.0 Hz); 2.862 (dd, 1H, J=13.7, 4.7 Hz); 2.885 (d, 1H, J=18.3 Hz); 2.962 (m, 1H); 3.570 (d, 1H, J=18.3 Hz); 3.634 (s, 3H); 6.715 (ddd, 1H, J=8.1, 2.5, 0.9 Hz); 6.839 (m, 2H); 7.048 (d, 1H, J=7.6 Hz); 7.197–7.080 (m, 4H. $^{13}$C NMR (CDCl$_3$): d 158.9, 148.9, 135.9, 135.6, 128.6, 128.36, 128.0, 125.9, 125.5, 120.0, 113.9, 110.8, 64.04, 54.9, 52.2, 46.6, 40.6, 40.11, 35.98, 31.5, 24.4.

(±)-(2,8a)-Dimethyl-4a-(3-Hydroxyphenyl)-Octahydrobenzo[e] Isoquinoline (20): To a 10 mL single necked flask was added 100 mg (0.31 mmol) of (±)-(2,8a)-dimethyl4a-(3-methoxyphenyl)-octahydrobenzo[e] isoquinoline and 0.8 mL of glacial acetic acid and 0.8 mL of 48% HBr. This mixture was heated under reflux for 18 hours and then cooled to room temperature. The pH was then adjusted to 10 with cooling starting with 50% NaOH and finishing with sat'd NaHCO$_3$. This was extracted 2 times with CHCl$_3$ and 2 times with 3:1 n-butanol:toluene. Both extracts were dried over K$_2$CO$_3$ and then the solvent was removed. The material from both extracts was examined by $^1$H NMR and was shown to contain the desired product. The material from the CHCl$_3$ layer was chromatographed on silica gel eluting with 25% CMA-80 in CHCl$_3$. This gave 27 mg of the desired product 20 (28% yield). The residue was dissolved in MeOH and to this was added 3 equivalents of 1N HCl in dry ethyl ether. The solvents were removed and several attempts were made to crystallize form ethyl acetate/MeOH. This only provided an oil. The same result was obtained with ethyl ether/MeOH. Finally, ethyl acetate was added to the residue and warmed and the solvent removed on a rotavap. This process was repeated 5 times and the solid thus formed was placed on a high vacuum pump overnight. MP ° C. 270–275 (dec). C, H, N.

$^1$H NMR (DMSO): δ 1.014 (s, 3H); 1.587 (d, 1H, J=14.3 Hz); 2.072 (s, 3H); 2.358 (d, 1H, J=17.4 Hz); 2.498 (d, 1H, J=17.4 Hz); 2.734 (s, 3H); 2.924–2.792 (m, 3H); 3.113 (d, 1H, J=13.1 Hz); 3.602 (d, 1H, J=18.78 Hz); 6.562 (d, 1H, J=8.0 Hz); 6.611 (m, 2H); 6.993 (t, 1H, J=7.5 Hz); 7.081 (d, 1H, J=7.5 Hz); 7.148 (t, 1H, J=7.8 Hz); 7.269–7.193 (m, 2H); 9.30 (s, 1H); 9.898 (bs, 1H).

$^{13}$C NMR(DMSO): δ 156.7, 146.4, 135.5, 133.3, 128.5, 128.4, 128.2, 126.2, 125.7, 117.6, 114.3, 113.5, 59.2, 49.4, 38.6, 35.4, 35.2, 31.0, 28.7, 22.8.

The butanol extracts contained 45 mg of the desired material giving an overall yield of 74.6 %.

TABLE 7

Radioligand Binding Results at all Three Opioid Receptors for New Antagonist Pharmacaphores

| Compound # | RTI # | [$^3$H] DAMGO$^a$ | [$^3$H] DADLE$^b$ | [$^3$H] U69,593$^c$ |
|---|---|---|---|---|
| | | IC$_{50}$ (nM ± SD) | | |
| (14) | 5989-30 | 243.7 ± 21.9 (1.00 ± 0.08) | >10,000 | 1470 ± 28.4 (0.89 ± 0.06) |
| (18) | 5989-31 | 4.54 ± 0.21 (1.08 ± 0.05) | 457.4 ± 50.5 (0.88 ± 0.08) | 27.2 ± 1.89 (1.25 ± 0.11) |
| (21) | 5989-28 | 406 ± 31.9 (1.02 ± 0.07) | >10,000 | 306.4 ± 28.4 (0.81 ± 0.06) |

$^a$Tritiated ligand selective for mu opioid receptor.
$^b$Tritiated ligand selective for delta opioid receptor.
$^c$Tritiated ligand selective for kappa opioid receptor.

TABLE 8

IC$_{50}$ Data for New Antagonists Toward Reversal of Agonist Stimulated GTP Binding

| Compound # | RTI # | DAMGO$^a$ | SNC 80$^b$ | U69, 593$^c$ |
|---|---|---|---|---|
| | | IC$_{50}$ (nM ± SD) | | |
| (14) | 5989-30 | 288 ± 78 | >1000 | >1000 |
| (18) | 5989-31 | 5.96 ± 0.72 | >1000 | 26.3 ± 8.3 |
| (21) | 5989-28 | NA | NA | 1552 ± 164 |

$^a$Agonist selective for mu opioid receptor.
$^b$Agonist selective for delta opioid receptor.
$^c$Agonist selective for kappa opioid receptor.

Example 4

κ-Selective N-Substituted Piperidines

Summary

The inhibition of radioligand binding and [$^{35}$S]GTPγS functional assay data for N-methyl- and N-phenethyl-9β-methyl-5-(3-hydroxyphenyl)morphans (5b and 5c) (FIG. 13) show that these compounds are pure antagonists at the μ, δ, and κ, opioid receptors. Since 5b and 5c have the 5-(3-hydroxyphenyl) group locked in a conformation comparable to an equatorial group of a piperidine chair conformation, this information provides very strong evidence that opioid antagonists can interact with opioid receptors in this conformation. In addition, it suggests that the trans-3,4-dimethyl4-(3-hydroxyphenyl)piperidine class of antagonist operates via a phenyl equatorial piperidine chair conformation.

Chemistry

Figure 13:
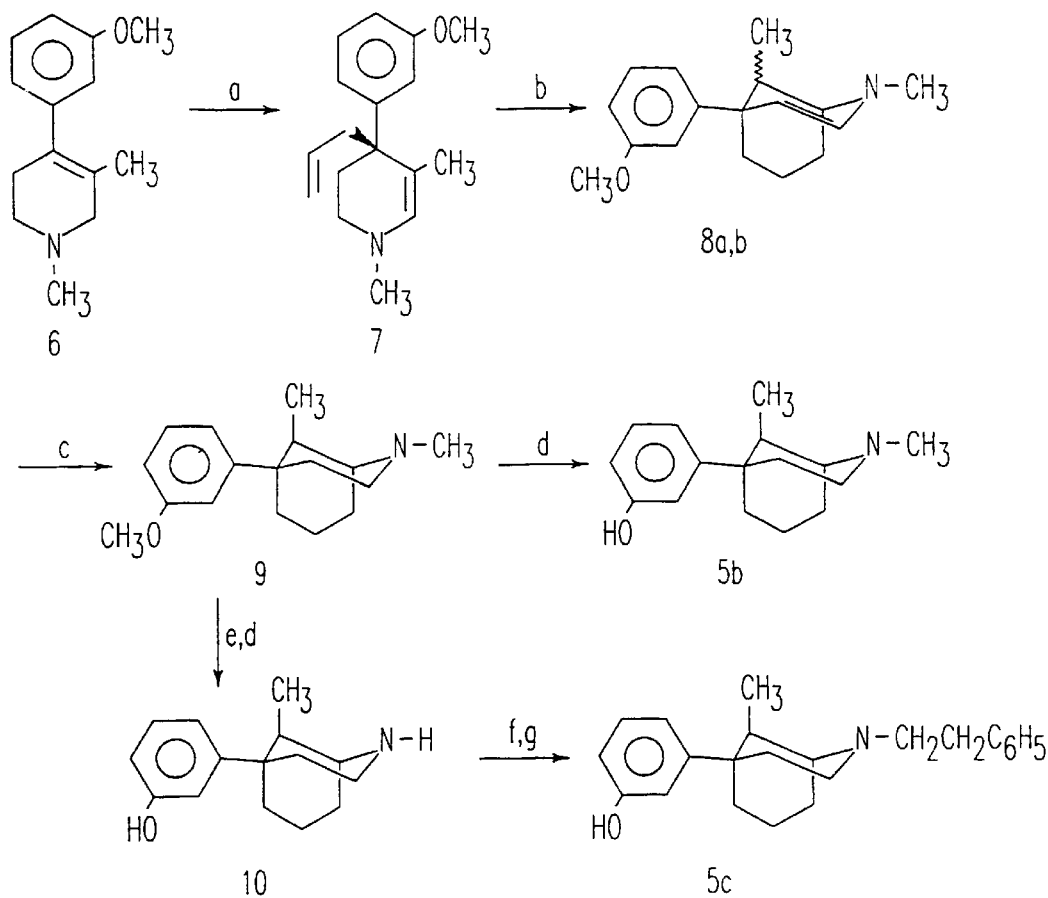
FIG. 13: Synthesis of compound (5c) as described in Example 4.
Figure 14:
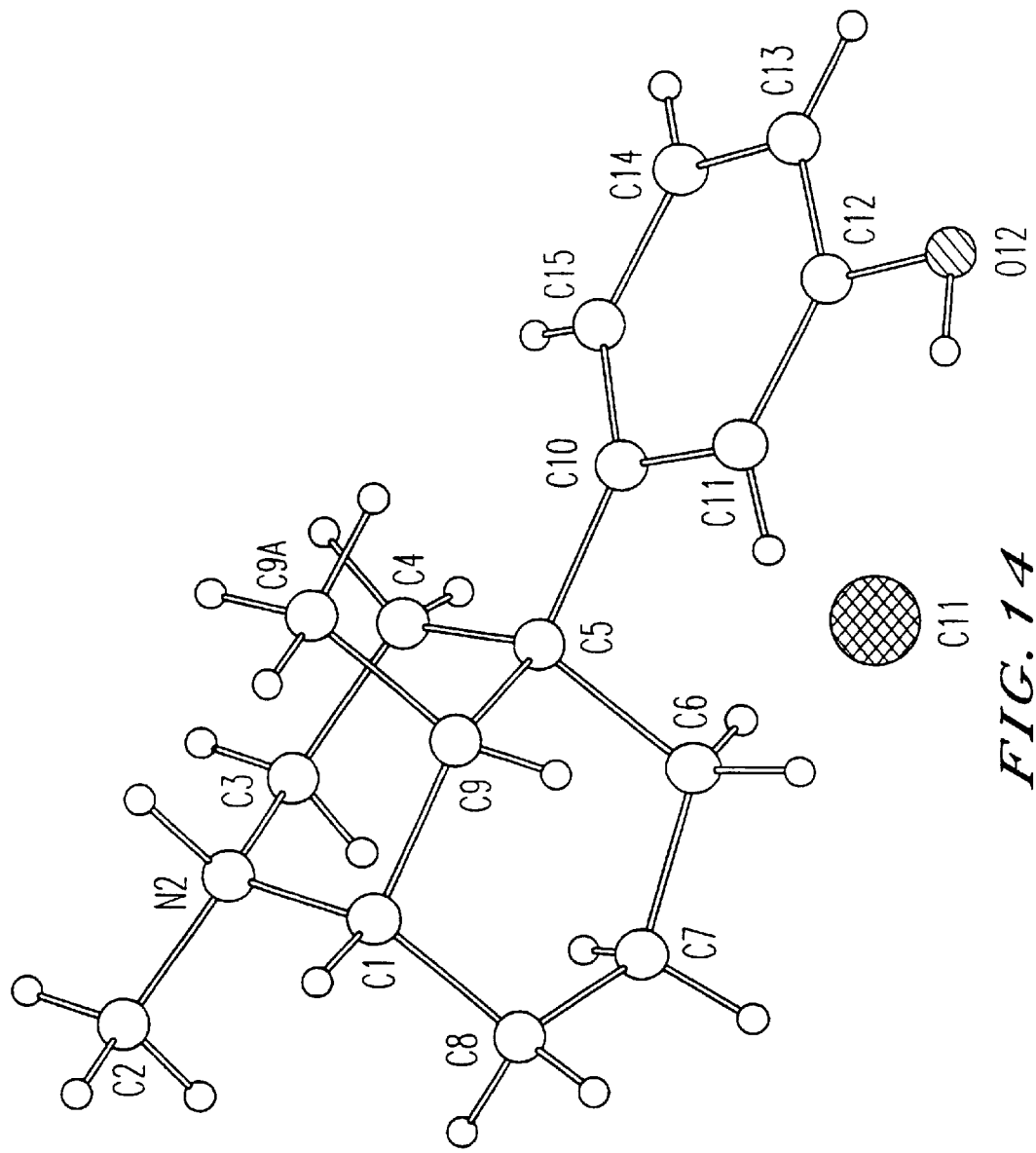
FIG. 14: X-Ray structure of (5b) described in Example 4 drawn using the experimentally determined coordinates.

The synthesis of the N-methyl- and N-phenethyl-9β-methyl-5-(3-hydroxyphenyl)-morphans (5b and 5c, respectively) was achieved as illustrated in FIG. 13.[1] Treatment of 1,2,6-trihydro-1,3-dimethyl-4-(3-methoxy)pyridine (6) with sec-butyl lithium followed by quenching with allyl bromide provided the enamine adduct (7) which was cyclized without isolation to give 2,9-dimethyl-5-(3-methoxyphenyl)-2-azabicyclo[3.3.1]non-3-ene (8a,b) in a 3:1 9β- to 9α-methyl ratio, using hydrochloric acid in tetrahydrofuran. Reduction of unpurified 8a,b using sodium borohydride triacetate followed by separation of the major isomer gave 9. Subjection of 9 to O-demethylation using hydrobromic acid in acetic acid provided the desired phenylmorphan (5b). Single crystal X-ray analysis showed that 5b had the desired 9β-methyl relative configuration (FIG. 14). The N-phenethyl derivative (5c) was prepared from intermediate 9. Treatment of 9 with phenylchloroformate followed by hydrolysis of the resulting urethane with potassium hydroxide followed by O-demethylation with hydrobromic acid in acetic acid gave 10. Compound 10 was converted to 5c by coupling with phenyl acetic acid in the presence of benzotriazol-1-yl-oxy-tris(dimethylamino) phosphonium hexafluorophosphate followed by borane reduction of the resulting amide intermediate.

Biological Results

Table 9 lists the radioligand binding data for compounds 5b and 5c along with data for naltrexone. While the binding of 5b to all three opioid receptors was weak, it is particularly interesting to note that changing the N-substituent from methyl to phenethyl (5c) provided a dramatic increase in binding affinity, a feature shared by the corresponding 4-(3-hydroxyphenyl)piperidine analogs (4a and 4b, Table 10).[2] Furthermore, the relative binding affinities displayed by 5b and 5c for mu and kappa opioid receptors are quite similar to that observed for 4a and 4b. These results show that the binding affinities of 5b and 5c are not adversely affected by the 1,5-carbon bridge present in these structures. In addition, it suggests a common binding mode for the two types of structures.

The increase in binding of [$^{35}$S]GTPγS stimulated by opioid agonists is an assay able to distinguish compounds of differing efficacy and intrinsic activity.[3] The antagonist properties of test compounds can be determined by measuring the inhibition of this stimulation. To assess their potency as antagonists and to verify that 5b and 5c retain pure antagonist activity, the compounds were analyzed for either stimulation or inhibition of agonist stimulated GTP binding in comparison with naltrexone (Table 11). In this functional assay, neither 5b nor 5c stimulated GTP binding as measured up to concentrations of 10 FM, showing that both compounds were devoid of agonist activity.[4] As mentioned previously, retention of pure antagonist activity regardless of the N-substituent structure is a key feature that separates the 3,4-dimethyl4-(3-hydroxyphenyl)piperidine class of antagonist from oxymorphone-based antagonists which display pure antagonism only for certain N-substituents such as the N-allyl or N-cyclopropylmethyl derivatives. In their ability to reverse agonist-stimulated GTP binding, compound 5c displayed a higher potency than naltrexone. These results are striking since agonist activity in several opioid ligands is enhanced by N-substituents with two methylene groups terminated by a phenyl group (N-phenethyl). It is evident that the antagonist activity of 5c is due to factors different from those of the oxymorphone-type pure antagonists.

The data in Table 11 also demonstrates that the N-methyl to N-phenethyl change, 5b to 5c, results in a concomitant increase in antagonist potency. Thus, as is the case for the 3,4-dimethyl-4-(3-hydroxyphenyl)piperidines, the antagonist potency and not the agonist/antagonist behavior of the 9β-methyl-5-(3-hydroxyphenyl)morphans (5b and 5c) is mediated by the N-substituent.

Discussion

These experiments demonstrated that N-methyl 9β-methyl-5-(3-hydroxyphenyl)morphan (5b) is an opioid receptor pure antagonist. In addition, replacing the N-methyl with an N-phenethyl group to give 5c resulted in a 63-, 60-, and 70-fold increase in antagonist potency at the mu, delta, and kappa opioid systems. These results are particularly important since changing an N-methyl to an N-phenethyl substituent in all opioid systems which have the 3-hydroxyphenyl group in an axial relationship relative to the piperidine ring results in an increase in opioid agonist activity.[5] This information strongly suggests that 5b and 5c are acting as conformationally rigid analogs of the trans-3,4-dimethyl4-(3-hydroxyphenyl)piperidine class of opioid antagonists where the 3-hydroxyphenyl group is in an equatorial position relative to the piperidine ring.

Figure 15:
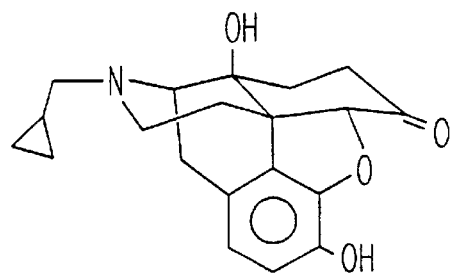
FIG. 15: Conformational representation of naltrexone (1b), N-substituted 3,4-dimethyl-4-(3-hydroxyphenyl)piperidine, and 2-alkyl-9β-5-(3-hydroxyphenyl)morphan. These compounds are described in Example 4.
Figure 15:
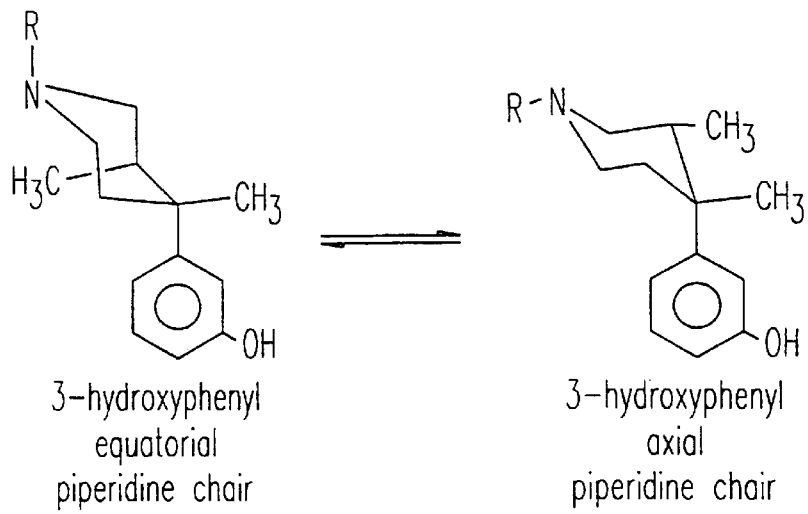
Figure 15:
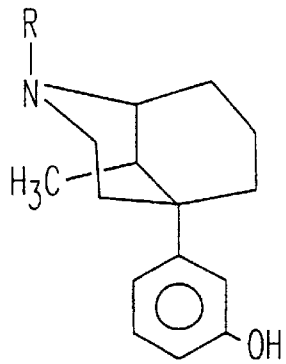

In opioid alkaloids like naloxone (1a) and naltrexone (1b), the 3-hydroxyphenyl ring is fixed in an axial orientation relative to the piperidine ring by the rigid framework of the structure (FIG. 15). The 3-hydroxyphenyl ring in the 3,4-dimethyl4-(3-hydroxyphenyl)piperidine analogs 4a can be either in axial or equatorial positions (FIG. 15). $^1$H and $^{13}$C NMR studies[6,7] as well as molecular modeling studies[2] suggest a preference for the 3-hydroxyphenyl equatorial conformation. 5-(3-Hydroxyphenyl)morphans like 5a–c are sterically constrained 4-(3-hydroxyphenyl)piperidines with the 3-hydroxyphenyl ring fixed in the equatorial position (FIG. 15). The pure antagonist activity of the morphans 5b and 5c strongly suggests that opioid ligands of the phenyl piperidine class express potent opioid antagonist activity with their 3-hydroxyphenyl group in an equatorial position.

A comparison of the radioligand and [$^{35}$S]GTPγS binding properties of the N-substituted 9, β-methyl-5-(3-hydroxyphenyl)morphans (5b and 5c) to those of the N-substituted 3,4-dimethyl4-(3-hydroxyphenyl)piperidines (4a and 4b) strongly suggests that these two types of compounds are interacting with opioid receptors in a similar mode. The pure antagonist activity of 5b, which is increased when the N-methyl group is replaced by a phenethyl group to give 5c, properties unique to the 3,4-dimethyl4-(3-hydroxyphenyl)piperidine class of antagonist, strongly supports the hypothesis that this class of opioid antagonist expresses pure antagonist activity with the 4-(3-hydroxyphenyl) group in an equatorial conformation.[8]

In summary, 9β-methyl-5-(3-hydroxyphenyl)morphans are a new structural type of pure opioid antagonist. The data also strongly supports the proposed 4-(3-hydroxyphenyl) equatorial piperidine chair mode of interaction for the trans-3,4-dimethyl-(3-hydroxyphenyl)piperidine class of opioid antagonist.

Experimental Section

Melting points were determined on a Thomas-Hoover capillary tube apparatus and are not corrected. Elemental analyses were obtained by Atlantic Microlabs, Inc. and are within ±0.4% of the calculated values. $^1$H-NMR were determined on a Bruker WM-250 spectrometer using tetramethylsilane as an internal standard. Silica gel 60 (230–400 mesh) was used for all column chromatography. All reactions were followed by thin-layer chromatography using Whatman silica gel 60 TLC plates and were visualized by UV or by charring using 5% phosphomolybdic acid in ethanol. All solvents were reagent grade. Tetrahydrofuran and diethyl ether were dried over sodium benzophenone ketyl and distilled prior to use.

The [$^3$H]DAMGO, DAMGO, and [$^3$H][D-Ala$^2$,D-Leu$^5$] enkephalin were obtained via the Research Technology Branch, NIDA, and were prepared by Multiple Peptide Systems (San Diego, Calif.). The [$^3$H]U69,593 and [$^{35}$S] GTPγS (SA=1250 Ci/mmol) were obtained from DuPont New England Nuclear (Boston, Mass.). U69,593 was obtained from Research Biochemicals International (Natick, Mass.). Levallorphan was a generous gift from Kenner Rice, Ph.D., NIDDK, NIH (Bethesda, Md.). GTPγS and GDP were obtained from Sigma Chemical Company (St. Louis, Mo.). The sources of other reagents are published.[8]

1,2,3,4-Tetrahydro-4-allyl-1,5-dimethyl-4-(3-methoxyphenyl)pyridine (7). To a solution of 500 mg (2.3 mmol) of 1,2,6-trihydro-1,3-dimethyl-4-(3-methoxy) pyridine (6) in 15 mL of THF at −42° C. was added s-BuLi in cyclohexane (1.3M, 2.9 mmol). After 1 h, allyl bromide (2.3 mmol) was added, and the color of the solution changed from dark red to yellow. After been stirred for 1 h at −42° C., the mixture was allowed to warmed to 0° C. and then quenched with water (10 mL). Diethyl ether (10 mL) was added, and the aqueous layer was extracted with ether (2×). The combined ether layers were washed with water (10 mL), saturated NaHCO$_3$, brine, and dried over Na2SO4. Evaporation of solvent afforded 590 mg (100%) of crude 7. The crude product was used directly in the next step without further purification. $^1$H NMR (CDCl$_3$) δ 7.26 (m, 1H), 7.01 (m, 2H), 6.74 (m, 1H), 5.89 (s, 1H), 5.82 (m, 1H), 5.13 (m, 2H), 3.80 (s, 3H), 2.68–2.40 (m, 3H), 2.55 (s, 3H), 2.22 (m, 1H), 1.66 (m, 2H), 1.52(s, 3H). $^{13}$C NMR(CDCl$_3$) δ 159.2, 151.1, 136.7, 135.8, 128.7, 119.8, 117.4, 114.3, 110.1, 107.7, 55.1, 46.1, 43.1, 43.0, 41.7, 36.4, 17.3.

2,9-Dimethyl-5-(3-methoxyphenyl)-2-azabicyclo[3.3.1] non-3-ene (8a,b). A solution of 300 mg (1.17 mmol) of 7 in 6 mL of 85% H$_3$PO$_4$/HCO2H (1:1) was stirred at room temperature for 72 h. The resulting dark-brown mixture was diluted with water (6 mL) and cooled in an ice bath while NaOH (25% w/w) was added until pH 8. The aqueous solution was extracted with CHCl$_3$ (3×). The combined organic layers were washed with aqueous NaHCO$_3$ and brine and dried over Na$_2$SO$_4$. Evaporation of the solvent gave 270 mg (90%) of crude products 8a and 8b in a ratio of 3:1. The crude products were used directly in the next step without further purification. $^1$H NMR (CDCl$_3$) of the mixture: δ 7.24–6.70 (m, 4H), 6.16 (d, 1H, J=9.2 Hz), 4.34 (d, 1H, J=7.0 Hz), 4.13 (d, 1H, J=9.1 Hz), 3.80 (s, 3H), 2.80 (s, 3H), 3.10–1.40 (m, 8H), 0.74 (d, 3H, J=8.6 Hz), 0.57 (d, 3H, J=8.1 Hz).

2,9β-Dimethyl-5-(3-methoxyphenyl)-2-azabicyclo[3.3.1] nonane (9). A solution of 270 mg (1.05 mmol) of 8a and 8b mixture and acetic acid (1.05 mmol, 0.061 mL) in 5 mL of dichloroethane was treated with NaBH(OAc)$_3$ under N$_2$ atmosphere. The reaction was stirred at room temperature for 2 h. The reaction was quenched by adding 10% NaOH to pH~10. The mixture was extracted with ether (3×), washed with water and brine. The organic phase was dried over Na$_2$SO$_4$ and concentrated under reduced pressure. Isolation of the major isomer by chromatography (1% Et$_3$N/EtOAc) gave 135 mg (50%) of 9 as a colorless oil. $^1$H NMR (CDCl$_3$) of 9 δ 7.26 (m, 1H), 6.94 (m, 2H), 6.70 (m, 1H), 3.80 (s, 3H), 3.05–2.90 (m, 2H), 2.71 (m, 1H), 2.43 (s, 3H), 2.42–2.30 (m, 2H), 2.28–2.15 (m, 1H), 2.00–1.35 (m, 6H), 0.86 (d, 3H, J=8.25 Hz). $^{13}$C NMR (CDCl$_3$) of 9 159.2, 152.0, 128.9, 118.0, 112.3, 109.6, 59.7, 55.1, 51.1, 43.1, 42.5, 40.0, 38.3, 29.1, 25.6, 23.4, 14.8. Anal. (C$_{17}$H$_{25}$NO): C, H, N.

2,9β-Dimethyl-5-(3-hydroxyphenyl)-2-azabicyclo[3.3.1 ]nonane (5b). Compound 9 was treated with 4 mL of glacial acetic acid and 4 mL of 48% aqueous hydrobromic acid at reflux temperature for 20 h. The reaction was cooled to room temperature and diluted with 10 mL of water. The pH was adjusted to 10 by using 50% NaOH with ice cooling. The product was extracted into a mixture of 3:1 1-butanol/toluene, dried over Na$_2$SO$_4$, and concentrated under reduced pressure. Separation by chromatography [50% (80% CHCl$_3$, 18% MeOH, 2% NH$_4$OH) in chloroform] provided 199 mg (84%) of 5b as a white solid. $^1$H NMR (CDCl$_3$) δ 7.15 (m, 1H), 6.87–6.75 (m, 2H), 6.61 (m, 1H), 3.10–2.90 (m, 2H), 2.77 (m, 1H), 2.44 (s, 3H), 2.50–2.30 (m, 2H), 2.25–2.10 (m, 1H), 2.00–1.60 (m, 5H), 1.60–1.40 (m, 1H), 0.80 (d, 3H, J=8.3 Hz). $^{13}$C NMR (CDCl$_3$) δ 155.9. The hydrochloride salt was prepared and crystallized from ether/methanol using 1 N HCl in ethyl ether. 152.0, 129.1, 117.5, 113.0, 112.4, 59.7, 51.0, 43.0, 42.0, 40.2, 38.0, 29.0, 25.6, 23.2, 14.6. The structure of this compound was determined by single crystal X-ray analysis. Anal. ($C_{16}H_{24}ClNO$): C, H, N.

5-(3-Hydroxyphenyl)-9β-methyl-2-azabicyclo[3.3.1]nonane (10). A solution of 200 mg (1.28 mmol) of phenyl chloroformate was added dropwise to 300 mg (1.16 mmol) of 9 in 10 mL of dichloromethane at room temperature under a nitrogen atmosphere. The reaction was heated to reflux for 6 h. Since the reaction was not complete by TLC, the solvent was then changed to dichloroethane and the reflux was continued for another 12 h. The mixture was cooled to room temperature and concentrated under reduced pressure. The resulting oil was treated with 10 mL of 1N NaOH and stirred with slight warming for 15 min. The product carbamate was then extracted with ether, and the ether layer was washed with 1N HCl and water. The organic phase was dried over $Na_2SO_4$ and concentrated under reduced pressure. The residue was then treated with 5 mL of ethanol and 1.5 mL of 50% aqueous KOH at reflux for 70 h. The mixture was cooled and concentrated under reduced pressure. The resulting concentrate was extracted with ether (2×), and the ether layers were concentrated in vacuo. The resulting oil was dissolved into 10 mL of 1 N HCl and washed with ether. The aqueous layer was then made strongly basic (pH >12) with 50% NaOH with ice cooling. The desired amine was extracted into ether (2×), and the ether extracts were washed, dried over $Na_2SO_4$, and concentrated under reduced pressure to give 207 mg (70%) of a light yellow oil. This was treated with 4 mL of glacial acetic acid and 4 mL of 48% aqueous hydrobromic acid at reflux temperature for 20 h. The reaction was cooled to room temperature and diluted with 10 mL of water. The pH was adjusted to 10 by using 50% NaOH with ice cooling. The product was extracted into a mixture of 3:1 1-butanol/toluene, dried over $Na_2SO_4$, and concentrated under reduced pressure to yield 100 mg (51%) of 10 as a semisolid. The crude product 10 was used directly in the next step without further purification. $^1$H NMR ($CD_3OD$) δ 7.15 (m, 1H), 6.79–6.75 (m, 2H), 6.65 (m, 1H), 3.70–3.30 (m, 3H), 2.70 (m, 1H), 2.45–1.70 (m, 8H), 0.87 (d, 3H, J=8.3 Hz).

5-(3-Hydroxyphenyl)-9β-methyl-2-(2'-phenylethyl)-2-azabicyclo[3.3.1]nonane (5c). To a solution of 100 mg (0.43 mmol) of 10 and 190 mg (0.43 mmol) of BOP reagent and 0.19 mL (1.38 mmol) of triethylamine in 15 mL of THF was added phenylacetic acid (70.25 mg, 0.52 mmol). The mixture was stirred at room temperature for 1 h. The reaction was diluted with 45 mL of water and ether (45 mL). The aqueous layer was extracted with ether (2×). The combined ether layers were washed with $NaHCO_3$ and brine, and dried over $Na_2SO_4$. Evaporation of solvent provided the crude product as a colorless oil. The crude amide was dissolved in THF (8 mL). The solution was cooled to 0° C., and borane:methyl sulfide complex (0.4 mL, 0.8 mmol) was added dropwise. After vigorous reaction ceased, the resulting mixture was slowly heated to reflux and maintained at that temperature for 4 h. The reaction mixture was cooled to 0° C., 6 mL of methanol was added, and the mixture was stirred for 1 h. Anhydrous hydrogen chloride in ether (1 mL) was added to attain a pH <2, and the resulting mixture was gently refluxed for 1 h. After the mixture was cooled to room temperature, methanol was added, and the solvents were removed on a rotovap. The residue obtained was made basic (pH >12) by adding 25% NaOH and extracted with ether (3×). The combined ether layers were dried over $Na_2SO_4$ and concentrated under reduced pressure. Separation by chromatography (1% $Et_3N$/50% EtOAc/hexanes) gave 38 mg (71%) of amine 5c as a colorless oil. $^1$H NMR ($CDCl_3$) δ 7.30–7.14 (m, 6H), 6.85 (m, 2H), 6.63 (m, 1H), 4.71 (br s, 1H), 3.05 (m, 2H), 2.88 (m, 1H), 2.79 (s, 4H), 2.43–2.15 (m, 3H), 1.94–1.65 (m, 5H), 1.65–1.45 (m, 1H), 0.83 (d, 3 H, J=8.2 Hz). $^{13}$C NMR ($CDCl_3$) δ 155.7, 152.5, 140.9, 129.1, 128.8, 128.3, 125.9. The hydrochloride salt was prepared and crystallized from ether/methanol using 1 N HCl in ethyl ether. 117.7, 113.0, 112.4, 57.4, 57.2, 49.5, 42.4, 40.0, 38.7, 34.1, 29.1, 26.2, 23.4, 14.7. Anal. ($C_{23}H_{30}ClNO$): C, H, N.

Opioid Binding Assays. Mu binding sites were labeled using [$^3$H][D-Ala$^2$-MePhe$^4$,Gly-ol$^5$]enkephalin ([$^3$H]DAMGO) (2.0 nM, SA=45.5 Ci/mmol), and delta binding sites were labeled using [$^3$H][D-Ala$^2$,D-Leu$^5$]enkephalin (2.0 nM, SA=47.5 Ci/mmol) using rat brain membranes prepared as described.[9] Kappa-1 binding sites were labeled using [$^3$H]U69,593 (2.0 nM, SA=45.5 Ci/mmol) and guinea pig membranes pretreated with BIT and FIT to deplete the mu and delta binding sites.[8]

[$^3$H]DAMGO binding proceeded as follows: 12×75 mm polystyrene test tubes were prefilled with 100 μL of the test drug which was diluted in binding buffer (BB: 10 mM Tris-HCl, pH 7.4, containing 1 mg/nL BSA), followed by 50 μL of BB, and 100 μL of [$^3$H]DAMGO in a protease inhibitor cocktail (10 mM Tris-HCl, pH 7.4, which contained bacitracin (1 mg/mL), bestatin (100 μg/mL), leupeptin (40 μg/mL), and chymostatin (20 μg/mL). Incubations were initiated by the addition of 750 μL of the prepared membrane preparation containing 0.2 mg/mL of protein and proceeded for 4 to 6 h at 25° C. The ligand was displaced by 10 concentrations of test drug, in triplicate, 2×. Nonspecific binding was determined using 20 μM levallorphan. Under these conditions, the $K_d$ of [$^3$H]DAMGO binding was 4.35 nM. Brandel cell harvesters were used to filter the samples over Whatman GF/B filters, which were presoaked in washbuffer (ice-cold 10 mM Tris-HCl, pH 7.4).

[$^3$H][D-Ala$^2$,D-Leu$^5$]enkephalin binding proceeded as follows: 12×75 mm polystyrene test tubes were prefilled with 100 μL of the test drug which was diluted in BB, followed by 100 μL of a salt solution containing choline chloride (1 M, final concentration of 100 mM), $MnC_{12}$ (30 mM, final concentration of 3.0 mM), and, to block mu sites, DAMGO (1000 nM, final concentration of 100 nM), followed by 50 μL of [$^3$H][D-Ala$^2$,D-Leu$^5$]enkephalin in the protease inhibitor cocktail. Incubations were initiated by the addition of 750 μL of the prepared membrane preparation containing 0.41 mg/mL of protein and proceeded for 4 to 6 h at 25° C. The ligand was displaced by 10 concentrations of test drug, in triplicate, 2×. Nonspecific binding was determined using 20 μM levallorphan. Under these conditions the $K_d$ of [$^3$H][D-Ala$^2$,D-Leu$^5$]enkephalin binding was 2.95 nM. Brandel cell harvesters were used to filter the samples over Whatman GF/B filters, which were presoaked in wash buffer (ice-cold 10 mM Tris-HCl, pH 7.4). [$^3$H]U69,593 binding proceeded as follows: 12×75 mm polystyrene test tubes were prefilled with 100 μL of the test drug which was diluted in BB, followed by 50 μL of BB, followed by 100 μL of [$^3$H]U69,593 in the standard protease inhibitor cocktail with the addition of captopril (1 mg/mL in 0.1N acetic acid containing 10 mM 2-mercapto-ethanol to give a final concentration of 1 μg/mL). Incubations were initiated by the addition of 750 μL of the prepared membrane preparation containing 0.4 mg/mL of protein and proceeded for 4 to 6 h at 25° C. The ligand was displaced by 10 concentrations of test drug, in triplicate, 2×. Nonspecific binding was determined using 1 μM U69,593. Under these conditions the $K_d$ of [$^3$H]U69,593 binding was 3.75 nM. Brandel cell harvesters were used to filter the samples over Whatman GF/B filters, which were presoaked in wash buffer (ice-cold 10 mM Tris-HCl, pH 7.4) containing 1% PEI.

For all three assays, the filtration step proceeded as follows: 4 mL of the wash buffer was added to the tubes, rapidly filtered and was followed by two additional wash cycles. The tritium retained on the filters was counted, after an overnight extraction into ICN Cytoscint cocktail, in a Taurus beta counter at 44% efficiency.

[$^{35}$S]-GTPγS Binding Assay. Ten frozen guinea pig brains (Harlan Bioproducts for Science, Inc, Indianapolis, Ind.) were thawed, and the caudate putamen were dissected and homogenized in buffer A (3 mL/caudate) (Buffer A 10 mM Tris-HCl, pH 7.4 at 4° C. containing 4 μg/mL leupeptin, 2 μg/mL chymostatin, 10 μg/mL bestatin, and 100 μg/mL bacitracin) using a polytron (Brinkman) at setting 6 until a uniform suspension was achieved. The homogenate was centrifuged at 30,000×g for 10 min at 4° C. and the supernatant discarded. The membrane pellets were washed by resuspension and centrifugation twice more with fresh buffer A, aliquotted into microfuge tubes, and centrifuged in a Tomy refrigerated microfuge (model MTX 150) at maximum speed for 10 min. The supernatants were discarded, and the pellets were stored at −80° C. until assayed.

For the [$^{35}$S]GTPγS binding assay, all drug dilutions were made up in buffer B [ 50 mM TRIS-HCl, pH 7.7/0.1 % BSA]. Briefly, 12×75 mm polystyrene test tubes received the following additions: (a) 50 μL buffer B with or without an agonist, (b) 50 μL buffer B with or without 60 μM GTPγS for nonspecific binding, (c) 50 μL buffer B with or without an antagonist, (d) 50 μL salt solution which contained in buffer B 0.3 nM [$^{35}$S]GTPγS, 600 mM NaCl, 600 μM GDP, 6 mM dithiothreitol, 30 mM MgCl$_2$, and 6 mM EDTA, and (e) 100 μL membranes in buffer B to give a final concentration of 10 μg per tube. The final concentration of the reagents were 100 mM NaCl, 5 mM MgCl$_2$, 1 mM EDTA, 1 mM dithiothreitol, 100 μM GDP, 0.1% BSA, 0.05–0.1 nM [$^{35}$S]GTPγS, 500 nM or 10 μM agonists, and varying concentrations (at least 10 different concentrations) of antagonists. The reaction was initiated by the addition of membranes and terminated after 4 h by addition of 3 mL ice-cold (4° C.) purified water (Milli-Q uv-Plus, Millipore) followed by rapid vacuum filtration through Whatman GF/B filters presoaked in purified water. The filters were then washed once with 5 mL ice-cold water. Bound radioactivity was counted by liquid scintillation spectroscopy using a Taurus (Micromedic) liquid scintillation counter at 98% efficiency after an overnight extraction in 5 mL Cytoscint scintillation fluid. Nonspecific binding was determined in the presence of 10 μM GTPγS. Assays were performed in triplicate, and each experiment was performed at least 3×.

Data Analysis. The data of the two separate experiments (opioid binding assays) or three experiments ([$^{35}$]-GTPγS assay) were pooled and fit, using the nonlinear least-squares curve-fitting language MLAB-PC (Civilized Software, Bethesda, Md.), to the two-parameter logistic equation[10] for the best-fit estimates of the IC$_{50}$ and slope factor. The K$_i$ values were then determined using the equation:

IC$_{50}$/1+([L]/K$_d$).

Single-Crystal X-Ray Analysis of 5b. Crystals of 5b were grown from ethyl ether/methanol. Data were collected on a computer-controlled automatic diffractometer, Siemens P4, with a graphite monochromator on the incident beam. Data were corrected for Lorentz and polarization effects, and a face-indexed absorption correction was applied. The structure was solved by direct methods with the aid of program SHELXS and refined by full-matrix least-squares on F2 values using program SHELXL. IThe parameters refined included the coordinates and anisotropic thermal parameters for all nonhydrogen atoms. Hydrogen atoms on carbons were included using a riding model in which the coordinate shifts of their covalently bonded atoms were applied to the attached hydrogens with C-H=0.96 A. H angles were idealized and Uiso(H) set at fixed ratios of Uiso values of bonded atoms. Coordinates were refined for H atoms bonded to nitrogen and oxygen. Additional experimental and structural analysis including an ORTEP figure, tables of atomic coordinates, bond lengths, and angles are available as supplementary material. Atomic coordinates are also available from the Cambridge Crystallographic Data Centre (Cambridge University Chemical Laboratory, Cambridge CB2 1EW, UK).

REFERENCES (1) Evans, D. A.; Mitch, C. H.; Thomas, R. C.; Zimmerman, D. M.; Robey, R. L. Application of metalated enamines to alkaloid synthesis. An expedient approach to the synthesis of morphine-based analgesics. *J. Am. Chem. Soc.* 1980, 102, 5955–5956. WARNING: read the background information relating to analogs of MPTP including refferences for Zimmerman et al., *J. Med Chem.* 1986, 29, 1517–1520 and references cited in reference 2.

(2) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for μ and κ opioid receptors. *J. Med. Chem.* 1993,36(20), 2833–2841.

(3) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and μ receptor subtype-selectivity in (+)-(3R, 4R)-dimethyl-4-(3-hydroxyphenyl)piperidine opioid antagonists. *J. Med. Chem.* 1998, 41(11), 1980–1990.

(4) Xu, H.; Lu, Y.-F.; Partilla, J. S.; Brine, G. A.; Carroll, F. I.; Rice, K. C.; Lai, J.; Porreca, F.; Rothman, R. B. Opioid peptide receptor studies. 6. The 3-methylfentanyl congeners RTI-4614-4 and its enantiomers differ in efficacy, potency, and intrinsic efficacy as measured by stimulation of [$^{35}$S]GTP-γ-S binding using cloned μ-opioid receptors. *Analgesia* 1997, 3, 35–42.

(5) Aldrich, J. V. Analgesics. In *Burger's Medicinal Chemistry and Drug Discovery*, Wolff, M. E. Eds.; John Wiley & Sons, Inc.: 1996; Vol. 3: Therapeutic Agents.

(6) Casy, A. F.; Dewar, G. H.; Al-Deeb, O. A. A. Stereochemical influences upon the opioid ligand activities of 4-alkyl-4-arylpiperidine derivatives. *Chirality* 1989, 1, 202–208.

(7) Casy, A. F.; Dewar, G. H.; Al-Deeb, O. A. A. Stereochemical studies of the 4-alkyl-4-arylpiperidine class of opioid ligand. *Magn. Reson. Chem.* 1989, 27, 964–972.

(8) Rothrman, R. B.; Bykov, V.; de Costa, B. R.; Jacobson, A. E.; Rice, K. C.; Brady, L. S. Interaction of endogenous opioid peptides and other drugs with four kappa opioid binding sites in guinea pig brain. *Peptides* 1990, 11, 311–331.

(9) Rothrman, R. B.; Xu, H.; Seggel, M.; Jacobson, A. E.; Rice, K. C.; Brine, G. A.; Carroll, F. I. RTI-4614-4: an analog of(+)-cis-3-methylfentanyl with a 27,000-fold binding selectivity for mu versus delta opioid binding sites. *Life Sci.* 1991, 48, PL111–PL116.

(10) Rodbard, D.; Lenox, R. H.; Wray, H. L.; Ramseth, D. Statistical characterization of the random errors in the radioimmunoassay dose-response variable. *Clin. Chem.* 1976, 22, 350–358.

(11) SHELXTL-Plus, Release 5.03, Sheldrick, G. M., Siemens Analytical X-ray Instruments, Inc., Madison, Wis., 1995.

TABLE 9

Radioligand Binding Results at the Mu, Delta, and Kappa Opioid Receptors for N-Methyl- and N-Phenethyl-9β-methyl-5-(3-hydroxyphenyl) morphans

| | Ki (nM ± SD) | | |
|---|---|---|---|
| Compd | $\mu$ [$^3$H]DAMGO[a] | $\delta$ [$^3$H]DADLE[b] | $\kappa$ [$^3$H]U69,593[c] |
| 5b | 166 ± 15 | >10,000 | 816 ± 66 |
| 5c | 3.11 ± 0.21 | 272 ± 30 | 14.5 ± 0.99 |
| 1b, naltrexone | 1.39 ± 0.40 | 94.9 ± 6.6 | 4.71 ± 0.7 |

[a][$^3$H]DAMGO [(D-Ala$^2$,MePhe$^4$,Gly-ol$^5$)enkephalin]. Tritiated ligand selective for mu opioid receptor. [b][$^3$H]DADLE [(D-Ala$^2$,D-Leu$^5$) enkephalin]. Tritiated ligand selective for delta opioid receptor. [c][$^3$H]U69, 593 {[$^3$H](5α,7α,8β)-(-)-N-methyl-N-[7-(1-pyrrolidinyl)-1-oxaspiro[4,5] dec-8-yl]benzeneacetamide). Tritiated ligand selective for kappa opioid receptor.

TABLE 10

Affinities of the N-Substituted-3,4-dimethyl-(3'-hydroxyphenyl)piperidine Antagonists for the Mu and Kappa Opioid Receptors[a]

| | Ki (nM) | |
|---|---|---|
| Compd | $\mu$ [$^3$H]Nal[b] | $\kappa$ [$^3$H]EKC[c] |
| 4a | 80 | 833 |
| 4b | 1.5 | 52 |
| 1b, naltrexone | 0.56 | 3.9 |

[a]Data taken from reference 2. [b][$^3$H]Naloxone ($\mu$ receptor assay). [c][$^3$H] Ethylketocyclazocine ($\kappa$ receptor assay).

TABLE 11

Inhibition by Antagonists of [$^{35}$S]GTPγS Binding in Guinea Pig Caudate Stimulated by DAMGO (mu), SNC80 (delta), and U69,593 (kappa) Selective Opioid Agonists[a]

| | Ki (nM ± SD) | | |
|---|---|---|---|
| Compd | $\mu$ (DAMGO)[a] | $\delta$ (SNC80)[b] | $\kappa$ (U69,593)[c] |
| 5b | 21.2 ± 2.30 | 750 ± 85.9 | 105 ± 10.9 |
| 5c | 0.338 ± 0.028 | 12.6 ± 1.01 | 1.34 ± 0.084 |
| 1b, naltrexone | 0.930 ± 0.21 | 19.3 ± 2.25 | 2.05 ± 0.21 |

[a]DAMGO [(D-Ala$^2$,MePhe$^4$,Gly-ol$^5$)enkephalin]. Agonist selective for mu opioid receptor. [b]SNC-80 ([(+)-4-[(αR)-α-(2S,5R)-4-allyl-2,5-dimethyl-1-piperazinyl)-3-methoxybenzyl]-N,N-diethylbenzamide). Agonist selective for delta opioid receptor. Agonist selective for delta opioid receptor. [c]U69, 593 (trans-3,4-dichloro-N-methyl[2-(1-pyrrolidinyl)cyclohexyl] benzeneacetamide). Agonist selective for kappa opioid receptor.

Elemental Analysis

| | Calcd. | | | Found | | |
|---|---|---|---|---|---|---|
| Compd | C | H | N | C | H | N |
| 9 C$_{17}$H$_{25}$NO | 78.72 | 9.71 | 5.40 | 78.79 | 9.75 | 5.34 |
| 5b C$_{16}$H$_{24}$ClNO | 68.19 | 8.53 | 4.91 | 68.25 | 8.53 | 5.03 |
| 5c C$_{23}$H$_{30}$ClNO | 74.27 | 8.13 | 3.77 | 74.16 | 8.12 | 3.71 |

X-Ray Crystallographic Data and Analysis for Compound 5b

TABLE S1

Crystal data and structure refinement for 5b.

| | |
|---|---|
| Empirical formula | C$_{16}$H$_{24}$ClNO |
| Formula weight | 281.81 |
| Temperature | 293(2)K |
| Wavelength | 1.54178 Å |
| Crystal system | Monoclinic |
| Space group | P2(1)/c |
| Unit cell dimensions | a = 14.183(1) Å $\alpha$ = 90°. |
| | b = 9.996(1) Å $\beta$ = 90.33(2)°. |
| | c = 11.126(1) Å $\gamma$ = 90°. |
| Volume | 1577.5(2) Å$^3$ |
| Z | 4 |
| Density (calculated) | 1.187 Mg/m$^3$ |
| Absorption coefficient | 2.072 mm$^{-1}$ |
| F(000) | 608 |
| Crystal size | 0.40 × 0.26 × 0.24 mm$^3$ |
| Theta range for data collection | 3.12 to 57.49°. |
| Index ranges | −15 <= h <= 3, −10 <= k <= 1, −12 <= l <= 12 |
| Reflections collected | 2651 |
| Independent reflections | 2154 [R(int) = 0.0312] |
| Absorption correction | Integration |
| Max. and min. transmission | 0.6449 and 0.5284 |
| Refinement method | Full-matrix least-squares on F$^2$ |
| Data/restraints/parameters | 2153/0/180 |
| Goodness-of-fit on F$^2$ | 1.047 |
| Final R indices [I > 2sigma(I)] | R1 = 0.0472, wR2 = 0.1367 |
| R indices (all data) | R1 = 0.0598, wR2 = 0.1493 |
| Largest diff. peak and hole | 0.213 and −0.228 e.Å$^{-3}$ |

TABLE S2

Atomic coordinates (×10$^4$) and equivalent isotropic displacement parameters (Å$^2$ × 10$^3$) for 5b. U(eq) is defined as one third of the trace of the orthogonalized U$^{ij}$ tensor.

| | x | y | z | U(eq) |
|---|---|---|---|---|
| Cl(1) | 6176(1) | 534(1) | 8837(1) | 56(1) |
| C(1) | 6136(2) | −4826(3) | 7545(2) | 44(1) |
| N(2) | 6354(2) | −5819(2) | 6563(2) | 45(1) |
| C(2) | 5733(3) | −7019(3) | 6587(3) | 64(1) |
| C(3) | 7374(2) | −6184(3) | 6510(3) | 54(1) |
| C(4) | 8010(2) | −4963(3) | 6522(3) | 49(1) |
| C(5) | 7760(2) | −3857(3) | 7430(3) | 40(1) |
| C(6) | 7948(2) | −4300(3) | 8752(3) | 48(1) |
| C(7) | 7345(2) | −5466(3) | 9198(3) | 58(1) |
| C(8) | 6319(2) | −5367(3) | 8813(2) | 56(1) |
| C(9) | 6690(2) | −3545(2) | 7321(2) | 39(1) |
| C(9A) | 6394(2) | −2839(3) | 6157(2) | 48(1) |
| C(10) | 8344(2) | −2595(3) | 7206(2) | 43(1) |
| C(11) | 8071(2) | −1398(3) | 7730(3) | 49(1) |
| O(12) | 8256(2) | 962(2) | 8052(3) | 79(1) |
| C(12) | 8549(2) | −214(3) | 7554(3) | 56(1) |
| C(13) | 9351(2) | −206(4) | 6853(3) | 68(1) |
| C(14) | 9646(2) | −1386(4) | 6351(3) | 72(1) |
| C(15) | 9160(2) | −2568(3) | 6503(3) | 60(1) |

TABLE S3

Bond lengths [Å] and angles [°] for 5b.

| | |
|---|---|
| C(1)-N(2) | 1.509(3) |
| C(1)-C(9) | 1.524(4) |
| C(1)-C(8) | 1.532(4) |
| N(2)-C(2) | 1.488(4) |
| N(2)-C(3) | 1.494(4) |
| C(3)-C(4) | 1.517(4) |
| C(4)-C(5) | 1.540(4) |
| C(5)-C(10) | 1.530(4) |
| C(5)-C(9) | 1.553(3) |
| C(5)-C(6) | 1.558(4) |
| C(6)-C(7) | 1.530(4) |
| C(7)-C(8) | 1.518(4) |
| C(9)-C(9A) | 1.533(3) |
| C(10)-C(11) | 1.387(4) |
| C(10)-C(15) | 1.401(4) |
| C(11)-C(12) | 1.378(4) |
| O(12)-C(12) | 1.365(4) |
| C(12)-C(13) | 1.383(5) |
| C(13)-C(14) | 1.371(5) |
| C(14)-C(15) | 1.379(5) |
| N(2)-C(1)-C(9) | 109.1(2) |
| N(2)-C(1)-C(8) | 113.6(2) |
| C(9)-C(1)-C(8) | 111.2(2) |
| C(2)-N(2)-C(3) | 112.2(2) |
| C(2)-N(2)-C(1) | 113.1(2) |
| C(3)-N(2)-C(1) | 113.1(2) |
| N(2)-C(3)-C(4) | 112.3(2) |
| C(3)-C(4)-C(5) | 116.4(2) |
| C(10)-C(5)-C(4) | 111.0(2) |
| C(10)-C(5)-C(9) | 110.5(2) |
| C(4)-C(5)-C(9) | 108.8(2) |
| C(10)-C(5)-C(6) | 107.4(2) |
| C(4)-C(5)-C(6) | 112.1(2) |
| C(9)-C(5)-C(6) | 107.0(2) |
| C(7)-C(6)-C(5) | 115.5(2) |
| C(8)-C(7)-C(6) | 113.3(2) |
| C(7)-C(8)-C(1) | 116.1(2) |
| C(1)-C(9)-C(9A) | 112.7(2) |
| C(1)-C(9)-C(5) | 108.9(2) |
| C(9A)-C(9)-C(5) | 114.9(2) |
| C(11)-C(10)-C(15) | 116.8(3) |
| C(11)-C(10)-C(5) | 119.4(2) |
| C(15)-C(10)-C(5) | 123.8(2) |
| C(12)-C(11)-C(10) | 122.9(3) |
| O(12)-C(12)-C(11) | 122.1(3) |
| O(12)-C(12)-C(13) | 118.5(3) |
| C(11)-C(12)-C(13) | 119.4(3) |
| C(14)-C(13)-C(12) | 118.6(3) |
| C(13)-C(14)-C(15) | 122.2(3) |
| C(14)-C(15)-C(10) | 120.0(3) |

TABLE S4

Anisotropic displacement parameters ($Å^2 \times 10^3$) for 5b. The anisotropic displacement factor exponent takes the form: $-2\pi^2 [h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| Cl(1) | 62(1) | 59(1) | 48(1) | 3(1) | -5(1) | 10(1) |
| C(1) | 47(2) | 39(2) | 45(2) | 1(1) | -1(1) | -1(1) |
| N(2) | 58(2) | 34(1) | 43(1) | 3(1) | -7(1) | -4(1) |
| C(2) | 88(2) | 42(2) | 62(2) | 5(2) | -8(2) | -21(2) |
| C(3) | 67(2) | 44(2) | 52(2) | -7(1) | -4(1) | 11(2) |
| C(4) | 52(2) | 47(2) | 50(2) | -7(1) | -1(1) | 9(1) |
| C(5) | 41(1) | 36(1) | 42(1) | -2(1) | -2(1) | 5(1) |
| C(6) | 50(2) | 48(2) | 45(2) | -1(1) | -9(1) | 7(1) |
| C(7) | 80(2) | 51(2) | 43(2) | 8(1) | -8(2) | -2(2) |
| C(8) | 70(2) | 53(2) | 45(2) | 4(1) | 4(1) | -16(2) |
| C(9) | 39(1) | 35(1) | 42(1) | 0(1) | -1(1) | -1(1) |
| C(9A) | 50(2) | 40(2) | 56(2) | 6(1) | -8(1) | 1(1) |
| C(10) | 36(1) | 48(2) | 45(2) | 2(1) | -2(1) | -2(1) |
| C(11) | 41(2) | 44(2) | 62(2) | -3(1) | 4(1) | -4(1) |
| O(12) | 73(2) | 40(1) | 124(2) | -6(1) | 8(2) | -10(1) |
| C(12) | 48(2) | 49(2) | 69(2) | 2(2) | -8(2) | -8(1) |
| C(13) | 54(2) | 65(2) | 85(2) | 7(2) | -2(2) | -22(2) |
| C(14) | 44(2) | 92(3) | 83(2) | -1(2) | 14(2) | -19(2) |
| C(15) | 45(2) | 68(2) | 68(2) | -9(2) | 5(2) | -2(2) |

TABLE S5

Hydrogen coordinates ($\times 10^4$) and isotropic displacement parameters ($Å^2 \times 10^3$) for 5b.

| | x | y | z | U(eq) |
|---|---|---|---|---|
| H(1A) | 5464(2) | 4606(3) | 7484(2) | 52 |
| H(2) | 6227(18) | -5389(28) | 5805(27) | 48(8) |
| H(2A) | 5086(3) | -6741(3) | 6621(3) | 97 |
| H(2B) | 5881(3) | -7550(3) | 7282(3) | 97 |
| H(2C) | 5832(3) | -7540(3) | 5874(3) | 97 |
| H(3A) | 7489(2) | -6694(3) | 5783(3) | 65 |
| H(3B) | 7531(2) | -6749(3) | 7191(3) | 65 |
| H(4A) | 8004(2) | -4574(3) | 5723(3) | 59 |
| H(4B) | 8649(2) | -5258(3) | 6687(3) | 59 |
| H(6A) | 8607(2) | -4549(3) | 8829(2) | 57 |
| H(6B) | 7843(2) | -3538(3) | 9274(2) | 57 |
| H(7A) | 7605(2) | -6297(3) | 8894(3) | 70 |
| H(7B) | 7378(2) | -5497(3) | 10069(3) | 70 |
| H(8A) | 5994(2) | -4795(3) | 9381(2) | 67 |
| H(8B) | 6040(2) | -6250(3) | 8870(2) | 67 |
| H(9A) | 6538(2) | -2934(2) | 7981(2) | 46 |
| H(9AA) | 6762(2) | -2041(3) | 6057(2) | 73 |
| H(9AB) | 5738(2) | -2608(3) | 6196(2) | 73 |
| H(9AC) | 6496(2) | -3425(3) | 5487(2) | 73 |
| H(11A) | 7544(2) | -1394(3) | 8222(3) | 59 |
| H(12) | 7646(36) | 906(46) | 8364(40) | 110(15) |
| H(13A) | 9683(2) | 583(4) | 6724(3) | 82 |
| H(14A) | 10192(2) | -1389(4) | 5893(3) | 87 |
| H(15A) | 9374(2) | -3347(3) | 6139(3) | 72 |

This Example is described in Thomas et al, *J. Med. Chem.*, V. 41, No. 21, 4143–4149 (1998) incorporated herein by reference, inclusive of the "Supporting Information Available" described at p. 4149.

Example 5

Synthesis of 9β-methyl-2-alkyl-7-oxo-5-arylmorphans

Summary

A convergent synthetic approach to 9β-methyl-2-alkyl-7-oxo-5-arylmorphans has been developed utilizing alkylation of the metalloenamine of 1,2,3,6-tetrahydro-4-aryl-1-alkylpyridines with 2-(chloromethyl)-3,5-dioxahex-1-ene (Okahara's reagent).

Chemistry

Figure 16:
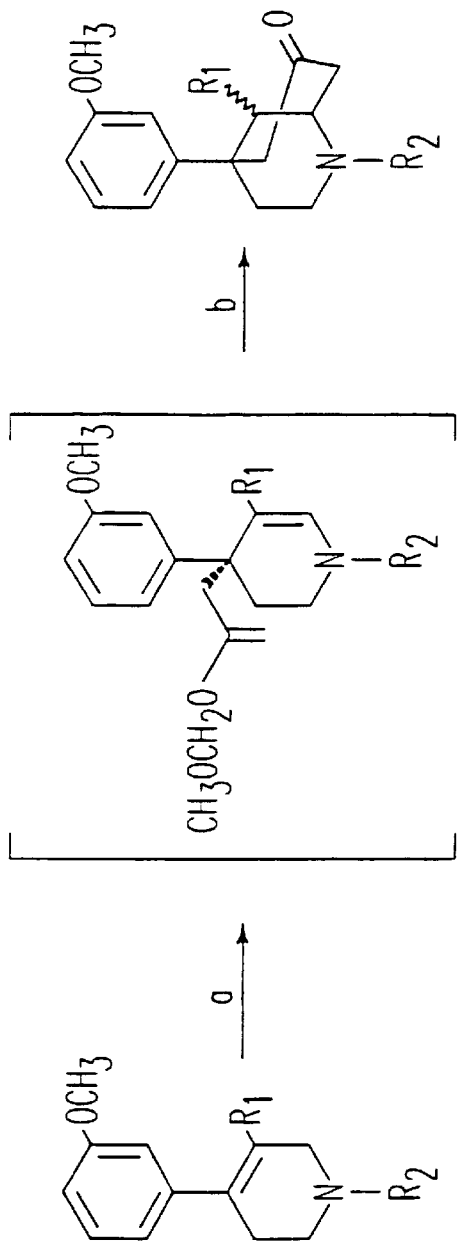
FIG. 16: Synthesis of compound (17) as described in Example 5.

Thus, treatment of the lithium salt of 15a with 18 provided 16a (not isolated) which cyclized on acidification with hydrochloric acid in tetrahydrofuran to give a 10:1 mixture of 17a and 17d as determined by $^1$H NMR analysis (FIG. 16). Separation by silica gel chromatography provided 43% of 17a. Proton assignments were made using a combination of HMQC, HMBC, and COSY. The 9βstereochemical assignments for 17a were made using NOESY techniques. In particular, the axial 9β-methyl group was observed to show an NOE interaction with the 4β proton.[1]

To expand this method to the ring unsubstituted derivatives and to explore potential limitations of the chemistry, compounds 17b (47%) and 17c (42%) were also prepared. It was shown earlier that differences in reactivities exist between unsubstituted and substituted systems, 15b,c and 15a. For example, s-BuLi is needed to effectively deprotonate 15a as opposed to 15b and 15c which require only n-BuLi.[2] This is a convenient route to the 7-oxophenylmorphan derivatives from either substituted or unsubstituted 4-phenyl-1,2,3,6-tetra-hydropyridines from intermediates which can be prepared in bulk and stored for long periods of time.

In summary, the 9β-methyl-7-oxo-5-arylmorphan 17a can be prepared in a convergent manner from tetrahydropyridine 15a by alkylation with 2-(chloromethyl)-3,5-dioxahex-1-ene 18 followed by cyclization under acidic conditions. This method provides the first reported access to the 9β-methyl substituted system with good control of the stereochemistry.

Application of the method to 15b and 15c provides a higher yielding route to the unsubstituted 7-oxophenylmorphan ring system and is amenable to large-scale synthesis.

REFERENCES AND NOTES

1. $^1$H NMR (CDCl$_3$) δ 0.92 (d, 3H, 9-CH$_3$), 1.76 (d, 1H, H4α), 2.23 (dd, 1H, H8), 2.33 (s, 3H, NCH$_3$), 2.37 (dd, 1H, H4β), 2.38 (dd, 1H, H3), 2.43 (d, 1H, H6), 2.50 (q, 1H, H9), 2.62 (d, 1H, H6), 2.72 (m, 1H, H3), 2.97 (d, 1H, H8), 3.10 (m, 1H, H1), 3.78 (s, 3H, OCH$_3$), 6.75 (dd, 1H, ArH), 6.87 (s, 1H, ArH), 6.92 (d, 1H, ArH), 7.25 (dd, 1H, ArH).
2. Barnett, C. J.; Copley-Merriman, C. R.; Maki, J. *J. Org. Chem.* 1989, 54, 4795–4800.

Supplementary Information

Melting points were determined on a Thomas-Hoover capillary tube apparatus and are not corrected. Elemental analyses were obtained by Atlantic Microlabs, Inc. and are within ±0.4% of the calculated values. $^1$H-NMR spectra were determined on a Bruker WM-250 spectrometer using tetramethylsilane as an internal standard. Radial chromatography was performed on a Harrison Research Chromatron model 7924T. All reactions were followed by thin-layer chromatography using Whatman silica gel 60 TLC plates and were visualized by UV or by charring using 5% phosphomolybdic acid in ethanol or by iodine staining. All solvents were reagent grade. In reactions, tetrahydrofuran and diethyl ether were dried over sodium benzophenone ketyl and distilled prior to use.

Note: The choice of piperidone in this synthesis is important in order to avoid the production of neurotoxic tetrahydropyridines such as 1-methyl-4-phenyl-1,2,3,6-tetrahydropyridine (MPTP). It has been demonstrated that the neurotoxic properties associated with MPTP or m-methoxy-MPTP are eliminated by any one of the following: N-substituents larger than methyl, piperidine ring substitution, and/or aryl substituents larger than methoxy.[1-3]

2,9-Dimethyl-5-(3-methoxyphenyl)-2-azabicyclo[3.3.1]nonan-7-one (17a): To a solution of 1500 mg (6.9 mmol) of tetrahydropyridine 5a[4] and TMEDA (2.1 mL, 13.8 mmol) in 30 mL of THF at 42° C. was added s-BuLi in cyclohexane (1.3 M, 8.9 mmol). After 1 h, 2-(chloromethyl)-3,5-dioxa-1-hexene 18 (1.32 g, 9.7 mmol) was added, and the color of the solution changed slowly from dark red to yellow. After being stirred for 1 h at −42° C. and kept 3 h at −23° C., the mixture was allowed to warm to 0° C. and then quenched with 1N HCl (20 mL). Diethyl ether (20 mL) was added, and the aqueous layer was extracted with ether (2x). The aqueous layer was adjusted to pH 10 and extracted with diethyl ether (3x). The combined ether layers were washed with water (10 mL), saturated NaHCO$_3$, brine, and dried over Na2SO$_4$. Evaporation of solvent afforded 1.31 g (60%) of crude 16a. The crude product was used directly in the next step without further purification. $^1$H NMR (CDCl$_3$) δ 7.27 (t, 1H, J=9.6 Hz), 7.02 (m, 2H), 6.72 (m, 1H), 5.83 (s, 1H), 4.93 (s, 2H), 3.81 (s, 3H), 3.43 (s, 3H), 2.70–2.40 (m, 8H), 2.52 (s, 3H), 1.61 (s, 3H). A solution of 500 mg of 16a in 3 mL of 6 M HCl and 25 mL of THF was stirred at room temperature for 72 h. The resulting brown mixture was neutralized with 10% NaOH (10 mL) until pH>9. The aqueous solution was extracted with diethyl ether (3x). The combined organic layers were washed with aqueous NaHCO$_3$ and brine. The organic phase was dried over Na$_2$SO$_4$ and concentrated under reduced pressure. The NMR shows that the ratio of 17a to 17d is about 10:1. Separation by chromatography [10% (80% chloroform, 18% methanol, 2% NH$_4$OH)/chloroform] gave 310 mg of 17a as a colorless oil (43% from 15a). $^1$H NMR (CDCl$_3$) δ 7.28 (t, 1H, J=9.5 Hz), 6.93 (m, 1H), 6.86 (m, 1H), 6.76 (dd, 1H, J=2.2, 9.7 Hz), 3.81 (s, 3H), 3.13 (m, 1H), 3.0 (d, 1H, J=20.5 Hz), 2.76 (m, 1H), 2.66–2.17 (m, 6H), 2.36 (s, 3H), 1.76 (m, 1H), 0.93 (d, 3H, J=8.2 Hz). $^{13}$C NMR (CDCl$_3$) 210.5, 159.6, 148.7, 129.4, 117.6, 112.2, 110.3, 61.7, 55.9, 55.0, 47.1, 42.8, 41.4, 39.6, 29.5, 13.8. Anal. Calcd. for C$_{17}$H$_{23}$NO$_2$. Found: C, 76.72; H, 8.62, N, 5.23.

2-Ethyl-5-(3-methoxyphenyl)-2-azabicyclo[3.3.1]nonan-7-one (17b): To a solution of 500 mg (2.3 mmol) of tetrahydropyridine 15b [1] and tetramethylethylene diamine (TMEDA) (0.69 mL, 4.6 mmol) in 15 mL of THF at 42° C. was added n-BuLi in hexanes (2.5M, 2.9 mmol). After 1 h, 2-(chloromethyl)-3,5-dioxa-1-hexene 18 (440 mg, 3.2 mmol) was added, and the color of the solution changed slowly from dark red to yellow. After being stirred for 1 h at −42° C. and kept 3 h at −23° C., the mixture was allowed to warm to 0° C. and then quenched with 1N HCl (10 mL). Diethyl ether (10 mL) was added, and the aqueous layer was extracted with ether (2x). The aqueous layer was adjusted to pH 10 and extracted with diethyl ether (3x). The combined ether layers were washed with water (10 mL), saturated NaHCO$_3$, brine, and dried over Na$_2$SO$_4$. Evaporation of solvent afforded 510 mg (70%) of crude 16b . The crude product was used directly in the next step without further purification. $^1$H NMR (CDCl$_3$) δ 7.20 (t, 1H, J=9.1 Hz), 6.97 (m, 2H), 6.67 (dd, 1H, J=1.9, 8.4 Hz), 6.03 (d, 1H, J=9.8 Hz), 4.74 (s, 2H), 4.69 (d, 1H, J=9.6 Hz), 3.79 (s, 3H), 3.26 (s, 3H), 2.86 (q, 2H, J=8.6 Hz), 2.80–2.39 (m, 6H), 2.12 (m, 2H), 1.02 (t, 3H, J=8.6 Hz). A solution of 510 mg of 16b in 3 mL of 6 M HCl and 25 mL of THF was stirred at room temperature for 72 h. The resulting brown mixture was neutralized with 10% NaOH (10 mL) until pH>9. The aqueous solution was extracted with diethyl ether (3x). The combined organic layers were washed with aqueous NaHCO$_3$ and brine. The organic phase was dried over Na$_2$SO$_4$ and concentrated under reduced pressure. Separation by chromatography [10% (80% chloroform, 18% methanol, 2% NH$_4$OH)/chloroform] gave 352 mg (80%, 47% from 15b) of 17b as colorless oil. $^1$H NMR (CDCl$_3$) δ 7.28 (t, 1H, J=9.6 Hz), 6.92 (m, 2H), 6.78 (dd, 1H, J=3.0, 9.7 Hz), 3.81 (s, 3H), 3.60 (m, 1H), 2.82 (m, 3H), 2.55 (q, 2H, J=8.6 Hz), 2.44–1.92 (m, 7H), 1.10 (t, 3H, J=8.6 Hz). $^{13}$C NMR (CDCl$_3$) 209.4, 158.7, 149.0, 128.5, 115.9, 110.2, 110.0. 54.1, 52.4, 52.2, 47.4, 44.4, 38.2, 37.6, 37.1, 36.7, 12.7. Anal. Calcd. for C$_{17}$H$_{23}$NO$_2$: C, 74.69; H, 8.48; N, 5.12. Found: C, 5 74.78; H, 8.60; N, 5.24.

2-Benzyl-5-(3-methoxyphenyl)-2-azabicyclo[3.3.1]nonan-7-one (17c): 3-Bromoanisole (50.0 g, 0.264 mol) was dissolved in 150 mL of THF and then chilled to −78° C.

n-Butyllithium (1.6M, 175 mL, 0.276 mol) was then added while maintaining the reaction temperature at −70° C. or below. After complete addition, the reaction mixture was stirred for an additional 60 min. 1-Benzyl4-piperidone in 150 mL of THF was then added at such a rate as to maintain the reaction temperature at −70° C. or below. The reaction was stirred at −70° C. for an additional 15 min, then the dry ice-acetone bath was removed, and the reaction was allowed to come to room temperature. Brine (400 mL) was added, and the organic layer was separated and washed with an additional 300 mL of brine. The organic layer was separated, dried ($K_2CO_3$), and concentrated in vacuo. 6N HCl (250 mL) was added to the oily residue which was then washed with EtOAc. The aqueous layer was separated, basified with 50% NaOH, and extracted with EtOAc. The EtOAc layer was separated, dried ($K_2CO_3$), and concentrated in vacuo to give 75.7 g of 4-(3-methoxyphenyl)-1-benzyl4-piperidinol as an orange oil. A sample was chromatographed on silica gel using hexane/EtOAc (7:3) mixtures as the eluent to afford a yellow oil which was dissolved in ether and treated with ethereal hydrochloric acid to give 4-(3-methoxyphenyl)-1-benzyl-4-piperidinol hydrochloride as a white solid (mp 195–197° C.). $^1$H NMR (CDCl$_3$) (free base) δ (ppm) 1.64–1.75 (m, 2H), 2.09–2.21 (m, 2H), 2.41–2.51 (m, 2H), 2.71–2.80 (m, 2H), 3.51 (s, 2H), 3.80 (s, 3H), 6.77–6.81 (m, 1H), 7.06–7.09 (m, 2H), 7.23–7.35 (m, 6H). Anal. Calcd for $C_{19}H_{23}NO_2$ HCl.1/2 $H_2O$: C, 66.56; H, 7.06; N, 4.09. Found: C, 66.41; H, 7.31; N, 4.33.

This material, 4-(3-methoxyphenyl)-1-benzyl-4-piperidinol (75.7 g, 0.25 mol), was dissolved in 400 mL of toluene, tosic acid (101.4 g, 0.53 mol) was added, and the mixture was heated under reflux in a Dean Stark trap for 90 min. The reaction mixture was cooled to room temperature, and water (400 mL) was added. The bottom layers were separated, made basic with 5N NaOH, and extracted with EtOAc. The EtOAc layer was separated, washed with brine, dried ($K_2CO_3$), and concentrated in vacuo to give 73.0 g of a red-orange oil. The oil was chromatographed on silica gel using hexane/EtOAc (4:1) mixtures as the eluent to afford 54.2 g of 1,2,3,6-tetrahydro-4-(3-methoxyphenyl)-1-benzylpyridine 15c (78%) as an orange oil. A sample of the free base was converted to its hydrochloride salt (ethereal HCl) to give 1,2,3,6-tetrahydro4-(3-methoxyphenyl)-1-benzylpyridine hydrochloride as a white solid (mp 196–196° C.). $^1$H NMR (CDCl$_3$) (free base) δ (ppm) 2.54–2.57 (br m, 2H), 2.68–2.73 (m, 2H), 3.14–3.18 (m, 2H), 3.63 (s, 2H), 3.78 (s, 3H), 6.04–6.07 (m, 1H), 6.79 (dd, 1H), 6.91–7.00 (m, 2H), 7.19–7.39 (m, 6H). Anal. Calcd. for $C_{19}H_{2}$, NO.HCl.1/4$H_2$0: C, 71.46; H, 6.79; N, 4.39. Found: C, 71.63; H, 6.97; N, 4.42.

1,2,3,6-Tetrahydro-4-(3-methoxyphenyl)-1-benzylpyridine 15c (5.0 g, 0.018 mol) was dissolved in 70 mL of THF and chilled to −78° C. in a dry ice-acetone bath. N-Butyllithium (1.6M, 12.0 mL, 0.0193 mol) was added to the reaction mixture at a rate that would maintain the temperature at −70° C. or below. After complete addition, the reaction was stirred for an additional 15 min, and the dry ice bath was replaced with a salt-ice bath. When the temperature rose to −15° C., 2-(chloromethyl)-3,5-dioxahex-1-ene 18 (3.2 g, 0.023 mol) in 40 mL of THF was added while keeping the reaction temperature at −10° C. or below and stirring for an additional 15 min at −15° C. The bath was removed, and the reaction was stirred at room temperature for an additional 17 h. The reaction was quenched with 30 mL of brine, the organic layer was separated, washed with 2×100 mL of brine, separated, dried ($K_2CO_3$), and concentrated in vacuo to get 6.8 g of an orange oil. This was dissolved in 100 mL of THF, and 20 mL of 6N HCl was added. This reaction was stirred at room temperature overnight. The reaction mixture was neutralized with aqueous NaHCO$_3$, added 100 mL of EtOAc, and separated the organic layer. The organic layer was washed with 10% NaHCO$_3$, brine, then separated, dried($K_2CO_3$), and concentrated in vacuo to give 4.8 g of 17c as a red oil. The oil was chromatographed on silica gel using hexane/EtOAc (65:35) mixtures, as the eluent, to yield an oil which crystallized upon addition of ether to give 2.5 g (42%) of 5-(3-methoxyphenyl)-2-benzyl-2-azabicyclo[3.3.1]nonan-7-one 17c as a beige solid (mp 108–109° C.). $^1$H NMR (CDCl$_3$) δ (ppm) 1.88–1.91 (m, 2H), 2.12–2.21 (m, 2H), 2.31–2.49 (m, 3H), 2.75–2.99 (m, 3H), 3.49 (br m, 1H), 3.60–3.72 (q, 2H), 3.80 (s, 3H), 6.75–6.80 (m, 1H), 6.88–6.96 (m, 2H), 7.25–7.34 (m, 6H). $^{13}$C NMR (CDCl$_3$) δ 210.4, 159.8, 150.2, 138.7, 129.5, 128.6, 128.3, 127.0, 117.0, 111.3, 111.0, 59.0, 55.2, 53.7, 53.3, 45.5, 39.2, 38.7, 38.0, 37.7. Anal. Calcd. for $C_{22}H_{25}NO_2$: C, 78.77; H, 7.51; N, 4.18. Found: C, 78.76; H, 7.59; N, 4.20.

REFERENCES

[1] Zimmerman D M, Cantrell B E, Reel J K, Hemrick-Luecke S K, Fuller R W. J. Med. Chem. 1986;29:1517–1520.
[2] Fuller R W. 1986.
[3] Fries D S, de Vries J, Hazelhoff B, Horn A S. J. Med. Chem. 1986;29:424.
[4] Barnett C J, Copley-Merriman C R, Maki J. J. Org. Chem. 1989;54:4795–4800.

This Example is described in Thomas et al, *Tetrahedron Letters*, V. 39, 7001–7004 (1998), incorporated herein by reference.

Example 6

Selective Delta Opioid Receptor Agonists
Chemistry

Figure 17:
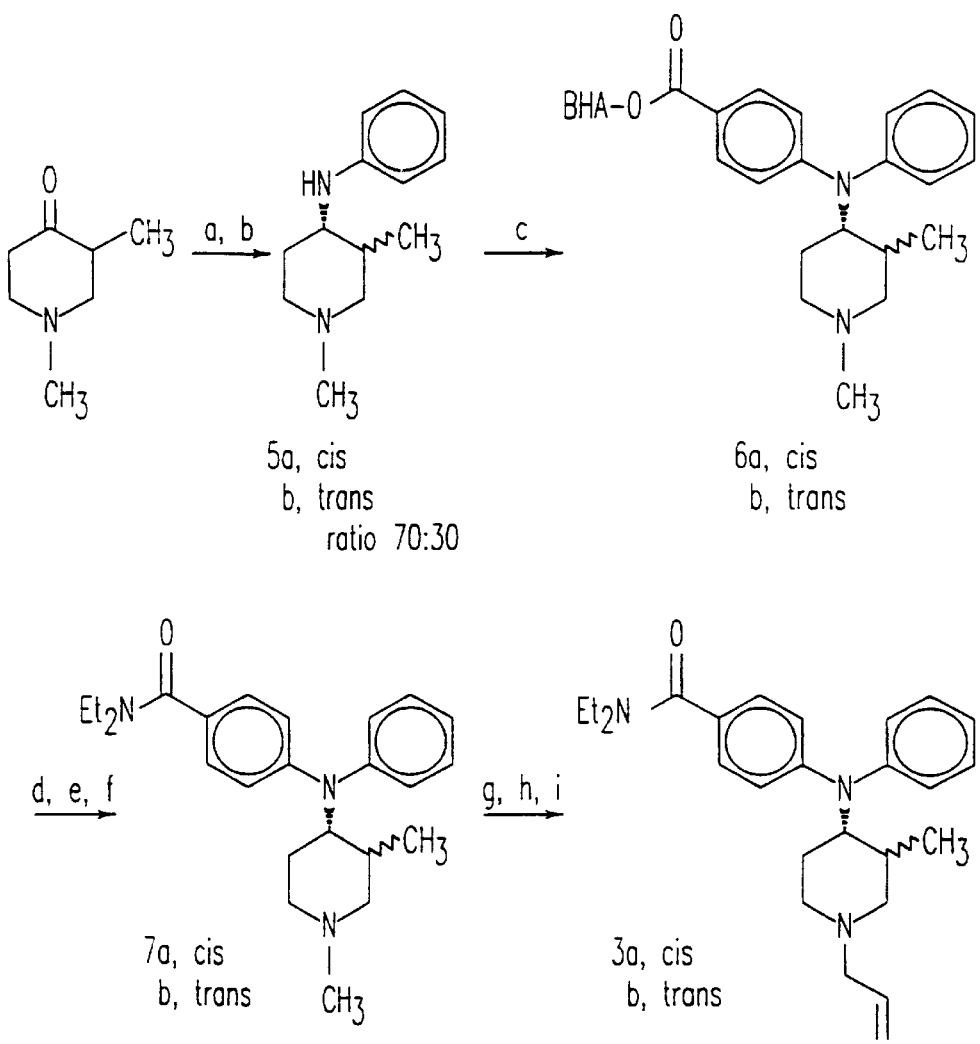
FIG. 17: Synthesis of compound (3) as described in Example 6.

Preparation of 3a,b began with reductive amination of 1,3-dimethyl4-piperidone with aniline using titanium (IV) isopropoxide[1] which gave 5a,b as a mixture of cis and trans diastereomers in 75% yield in a ratio of 70:30 (FIG. 17). These were separated by column chromatography and carried forward independently. These intermediates were then coupled to the butylated hydroxyanisole (BHA) ester of 4-fluorobenzoic acid to give (6a,b) in 91% and 68% yields.[2] Removal of the BHA group was accomplished by transesterification with refluxing sodium methoxide in toluene/N-methylpyrrolidinone followed by saponification of the methyl ester. The zwitterionic intermediates were isolated as HCl salts and converted directly into diethylamides using benzotriazol-1-yl-oxy-tris-(dimethylamino) phosphonium hexafluorophosphate (BOP a.k.a. Castro's reagent), diethylamine, and triethylamine in a tetrahydrofuran (THF) slurry to give 7a and 7b in 90% and 59% yields, respectively. Conversion to the N-allyl group was accomplished by treating 7a,b with phenyl chloroformate followed by hydrolysis of the resulting carbamates with potassium hydroxide in isopropyl alcohol. N-Alkylation with allyl bromide then gave 3a,b in 40% and 20% yield, respectively. Stereochemical assignments for 3a were made using NOESY spectra and vicinal coupling constants. Proton and carbon assignments were made using a combination of COSY and HETCORR spectra. A large coupling constant (J=13.0 Hz) between H5 and H4 indicated a diaxial arrangement between these protons showing that the 4-diarylamine is in the equatorial position. The NOESY spectrum contained a strong interaction between 5H-axial and the 3-methyl showing that the methyl group is also axial. The axial equatorial relationship between the methyl and the 4-diarylamine group established the cis relative stereochemistry for 3a.

Biological Activity

The binding affinities of the compounds for the $\mu$, $\delta$, and $\kappa$ opioid receptors were determined using competitive binding assays following previously reported procedures.[3] The results are listed in Table 12.

Results and Discussion

The radioligand binding data for the compounds 3a,b along with comparative data for BW373U86 (1) and the two enantiomers of cis-3-methylfentanyl 4 are shown in Table 12. Compound 3a (the cis isomer) is more potent and more selective for the $\delta$ opioid receptor relative to both the $\mu$ and $\kappa$ opioid receptors than 3b (the trans isomer). This difference in selectivity is due to a significantly lower affinity of the trans isomer for the $\delta$ receptor relative to the $\mu$ or $\kappa$ opioid receptors. The 11.9 nM Ki values for 3a combined with the 1212 nM Ki value at the $\mu$ receptor compare favorably to the

REFERENCES (1) Mattson, R. J.; Pham, K. M.; Leuck, D. J.; Cowen, K. A. An improved method for reductive alkylation of amines using titanium(IV) isopropoxide and sodium cyanoborohydride. *J. Org. Chem.* 1990, 55, 2552–2554.

(2) Hattori, T.; Satoh, T.; Miyano, S. Convenient synthesis of triarylamines via ester-mediated nucleophilic aromatic substitution. *Synthesis* 1995, 514–518.

(3) Thomas, J. B.; Zheng, X.; Mascarella, S. W.; Rothman, R. B.; Dersch, C. M.; Partilla, J. S.; Flippen-Anderson, J. L.; George, C. F.; Cantrell, B. E.; Zimmerman, D. M.; Carroll, F. I. N-Substituted 9β-methyl-5-(3-hydroxyphenyl)morphans are opioid receptor pure antagonists. *J. Med. Chem.* 1998,41(21),4143–4149.

(4) Xu, H.; Kim, C.-H.; Zhu, Y. C.; Weber, R. J.; Rice, K. C.; Rothman, R. B. (+)-cis-Methylfentanyl and its analogs bind pseudoirreversibly to the mu opioid binding site: Evidence for pseudoallosteric modulation. *Neuropharmacology* 1991, 30, 455–462.

TABLE 12

Radioligand Binding Results at the $\mu$, $\delta$, and $\pi$ Opioid Receptors for (±)-4-[(N-Allyl-3-methyl-4-piperidinyl)-phenylamino]N,N-diethylbenzamides

| | Ki (nM ± SD) | | | |
|---|---|---|---|---|
| Compd | $\mu$ [3H]DAMGOa | $\delta$ [3H]DADLEb | $\kappa$ [3H]U69,593c | $\mu/\delta$ |
| 1, BW373U86 | 36 ± 3.4 | 0.91 ± 0.05 | NA | 40 |
| 3a, (±)-cis-isomer | 1212 ± 132 | 11.9 ± 0.9 | 3284 ± 299 | 102 |
| 3b, (±)-trans-isomer | 1589 ± 86 | 126 ± 5 | 8695 ± 978 | 13 |
| 4a, (3S,4R)-isomer d | 30.6 ± 5.13 | >1000 | NA | 0.03 |
| 4b, (3R,4S)-isomer d | 0.020 ± 0.005 | 77.3 ± 6.7 | 57.4 ± 6.1 | 0.0003 | aÊ[3H]DAMGO [(D-Ala2,MePhe4,Gly-ol5)enkephalin]. Tritiated ligand selective for $\mu$ opioid receptor. bÊ[3H]DADLE [(D-Ala2,D-Leu5)enkephalin]. Tritiated ligand selective for δ opioid receptor. cÊ[3H]U69,593 {[3H](5α,7α,8β)-(–)-N-methyl-N-[7-(1-pyrrolidinyl)-1-oxaspiro[4,5]dec-8-yl]benzeneacetamide}. Tritiated ligand selective for κ opioid receptor. d Data taken from reference 4. In this experiment, $\mu$ sites were labeled with [3H]FOXY ([3H]6β-fluoro-6-desoxyoxymorphone).

Ki values for 1 (BW373U86) particularly when one considers that 3a is racemic and does not possess all the structural features present in 1, namely the 3'-hydroxy group on the aromatic ring and a methyl group comparable to the piperazine 2-methyl group.

A comparison of the binding data of 3a to that of cis-3-methylfentanyl, particularly the more potent 3R,4S-isomer 4b, is even more striking than the comparison of 3a to 1. Compound 4b gave a 3900-fold selectivity for the $\mu$ receptor relative to the $\delta$ receptor, whereas 3a possesses a 102-fold $\delta$ selectivity relative to the $\mu$ receptor. This results from a isevenfold increase in affinity at the $\delta$ receptor (11.9 nM vs. 77.3 nM) and a >60,000-fold loss in affinity at the $\mu$ receptor. Thus changing the propanamido and phenethyl groups present in 4b to the 4-diethylcarboamidophenyl and allyl in 3a converts a highly $\mu$-selective fentanyl analog to a $\delta$-selective ligand. It is highly likely that the gain in $\delta$-receptor potency is due to the change of the propanamido group of 4 to the diethylcarboxamidophenyl group in 3a. The loss is $\mu$-receptor potency may be due to both changes. Regardless of the reason for the $\delta$ opioid receptor selectivity, compound 3a represents a novel ligand for the $\delta$ opioid receptor.

TABLE 13

| | Elemental Analyses | | |
|---|---|---|---|
| Compound | % Calculated (C %, H %, N %) | % Found (C %, H %, N %) | Melting point ° C. |
| 7a | 66.42, 8.36, 9.68 | 66.20, 8.31, 9.76 | 193–194 |
| 7b | 65.73, 8.39, 9.58 | 65.69, 8.33, 9.62 | 199–201 |
| 3a | 69.93, 8.24, 9.41 | 70.06, 8.30, 9.10 | 221–225.5 |
| 3b | 69.93, 8.24, 9.41 | 69.66, 8.31, 9.31 | 177–178 |

Experimental (±)-(3RS,4SR)-4-Phenylamino-1,3-dimethylpiperidine (5a) and (±)-(2RS,3RS)-4-phenylamino-1,3-dimethylpiperidine (5b)

1,3-Dimethyl-4-piperidone (11.77 g, 92.68 mmol), aniline (8.5 mL, 93.4 mmol), and titanium isopropoxide (35 mL, 117.7 mmol) were heated at 55° C. for 20 h under a nitrogen atmosphere. The reaction mixture was allowed to cool and diluted with ethanol (100 mL). Sodium borohydride (5.0 g, 131.6 mmol) was then added, and the reduction was allowed to proceed at room temperature for 4 h. The reaction was quenched by addition of water, filtered over celite, and the filtrate was washed with ethanol. After evaporation of the solvent under reduced pressure, the white residue was taken up in ethyl acetate and again filtered over celite. After evaporation of the solvent under reduced pressure and chromatography on silica gel using ethyl acetate in hexanes (20:80), a 70:30 mixture of diastereomers (5a and 5b) (13.80 g, 73%) was obtained. Further separation by chromatography using the same system afforded first 5a (8.46 g) as a yellow oil, tentatively assigned a cis relative stereochemistry, and then 5b (2.04 g) as a white solid. 1H NMR 5a (CDCl$_3$) δ 0.98 (d, 3H, J=6.9 Hz), 1.67D1.89 (m, 2H), 2.03–2.58 (m, 4H), 2.18 (s, 3H), 3.41D3.68 (m, 2H), 6.60 (dd, 2H, J=0.9 Hz, J=8.6 Hz), 6.67 (dd, 1H, J=0.9 Hz, J=7.3 Hz), 7.15 (t, 2H, J=7.3 Hz). 1H NMR 5b (CDCl$_3$) δ 0.98 (d, 3H, J=6.3 Hz), 1.19–1.48 (m, 1H), 1.58–1.62 (m, 1H), 1.77 (t, 1H, J=11.0 Hz), 1.96–2.15 (m, 2H), 2.27 (s, 3H), 2.78–2.93 (m, 3H), 3.27–3.41 (m, 1H), 6.57 (dd, 2H, J=1.0 Hz, J=8.6 Hz), 6.66 (dd, 1H, J=1.0 Hz, J=7.3 Hz), 7.12 (t, 2H, J=7.3 Hz).

(±)-2,6-Di-tert-butyl4-methoxyphenyl-4-[N-{(3RS,4SR)-N,3-dimethyl4-piperidinyl}-phenylamino]benzoate (6a)

(±)-(3RS,4SR)-4-Phenylamino-1,3-dimethylpiperidine (5a) (3.41 g, 16.72 mmol) was dissolved in dry tetrahydrofuran (THF, 13 mL) and dry hexamethylphosphoramide (HMPA, 5 mL), and cooled to 42° C. A 2.5 M solution of n-butyllithium in hexanes (7.7 mL, 19.25 mol) was slowly added, and the reaction mixture was kept at 0° C. for 1 h. The reaction mixture was cannulated into a solution of (2,6-di-tert-butyl-4-methoxyphenyl)-4-fluorobenzoate (6.0 g, 16.76 mmol) in dry THF (13 mL) and dry HMPA (5 mL) at room temperature then heated to 45–50° C. for 5 h. The reaction mixture was cooled then quenched with a solution of NH$_4$Cl and diluted with ether. The aqueous layer was made basic (pH=14) with NaOH 25%, extracted with ether (200 mL), and the ethereal layer was washed with water three times. After drying with MgSO$_4$ and evaporation of the solvents under reduced pressure, a crude brown oil was afforded. Chromatography on silica gel using ethyl acetate in hexanes (20:80) gave 6a (8.20 g, 91%) as a yellow solid: 1H NMR (CDCl$_3$) δ 1.21 (d, 3H, J=6.9 Hz), 1.31 (s, 18H), 1.53–1.71 (m, 2H), 1.89–1.97 (m, 1H), 2.04 (s, 3H), 2.03–2.32 (m, 1H), 2.59–2.88 (m, 3H), 3.81 (s, 3H), 4.00–4.06 (m, 1H), 6.58 (d, 2H, J=9.1 Hz), 6.89 (s, 2H), 7.22 (d, 2H, J=8.2 Hz), 7.33 (d, 2H, J=7.2 Hz), 7.41 (t, 1H, J=7.2 Hz), 7.97 (d, 2H, J=9.0 Hz).

(±)2,6-Di-tert-butyl4-methoxyphenyl-4-[N-{(3RS,4RS)-N,3-dimethyl-4-piperidinyl}phenylamino]benzoate (6b)

(±)-(2RS,3RS)4-Phenylamino-1,3-dimethylpiperidine (5b) (2.65 g, 12.99 mmol) was treated with a 2.5 M solution of n-butyllithium in hexanes (6 mL, 15 mol) in dry THF (10 mL) and dry HMPA (4 mL) and coupled with (2,6-di-tert-butyl4-methoxyphenyl)4-fluorobenzoate (4.65 g, 12.99 mmol) in dry THF (10 mL) and dry HMPA (4 mL) as before. Purification afforded 6b (4.80 g, 68%) as a yellow solid: 1H NMR (CDCl$_3$) δ 1.07 (d, 3H, J=5.6 Hz), 1.31 (s, 18H), 1.63–2.15 (m, 5H), 2.25 (s, 3H), 2.85–2.97 (m, 2H), 3.68–3.78 (m, 1H), 3.81 (s, 3H), 6.63 (d, 2H,J=9.1 Hz), 6.88 (s, 2H), 7.19 (d, 2H,J=7.1 Hz), 7.33 (t, 1H, J=7.1 Hz), 7.44 (t, 2H, J=7.7 Hz), 7.95 (d, 2H, J=9.1 Hz).

(±)4-[N-{(3RS,4SR)-N,3-Dimethyl-4-piperidinyl}phenylamino]-N,N-diethylbenzamide (7a)

(±)-2,6-Di-tert-butyl-4-methoxyphenyl4-[N-{(3RS,4SR)-N,3-dimethyl4-piperidinyl}phenylamino]benzoate (6a) (6.5 g, 11.99 mmol) in toluene (150 mL) and N-methylpyrrolidinone (NMP, 40 mL) was added to freshly prepared sodium methoxide (120 mmol) and heated at reflux for 4 h. After evaporation of the toluene under reduced pressure, the residue was dissolved in a mixture of MeOH and H$_2$0 (12:1, 150 mL) and heated at reflux for 1 h. After evaporation of the alcohol, the residue was taken up in water (400 mL) and extracted with hexanes (2×100 mL). The aqueous layer was made acidic (pH=1) with 10% HCl, saturated with NaCl, and extracted with a mixture of CH$_2$Cl$_2$ and THF (3:1, 5:200 mL). After drying over Na$_2$SO$_4$, the solvents were evaporated under reduced pressure. This was then treated with diethylamine (1.2 mL), benzotriazol-1-yl-oxy-tris-(dimethylamino)phosphonium hexafluorophosphate (BOP a.k.a. Castro's reagent) (5.0 g, 11.31 mmol)), and triethylamine (4.2 mL) in THF (100 mL) for 30 min. The reaction mixture was next diluted with ether (300 mL), washed with water (2×75 mL), saturated NaHCO$_3$ (75 mL), and dried over Na$_2$SO$_4$ providing a black oil following evaporation of the solvents under reduced pressure. Chromatography on silica gel using hexanes/ethyl acetate/ethanol/triethylamine (60:40:2:2) afforded 7a (4.10 g, 90%) as a yellow liquid. This was converted to the hydrochloride salt using 1N HCl in ether. $^1$H NMR (CD$_3$OD) δ 1.07–1.38 (m, 12H), 1.42D1.61 (m, 1H), 1.68–1.92 (m, 1H), 2.86 (s, 3H), 3.03D3.21 (m, 1H), 3.27D3.60 (m, 6H), 4.30D4.48 (m, 1H), 6.80 (d, 2H, J=8.3 Hz), 7.14 (d, 2H, J=7.7 Hz), 7.26 (t, 3H, J=7.5 Hz), 7.40 (t, 2H, J=7.4 Hz); $^{13}$C NMR (CD$_3$OD) δ 12.2, 25.6, 30.4, 44.5, 55.7, 56.0, 60.2, 119.4, 127.4, 128.8, 130.7, 130.8, 146.1, 150.8, 173.8. Anal. (C$_{24}$H$_{34}$ClN$_3$O.H$_2$O): C, H, N.

(±)4-[N-{(3RS,4RS)-N,3-Dimethyl4-piperidinyl}phenylamino]-N,N-diethylbenzamide (7b)

(±)-2,6-Di-tert-butyl4-methoxyphenyl4-[N-{(3RS,4RS)-N,3-dimethyl4-piperidinyl}phenylarino]benzoate (6b) (7.38 g, 13.62 mmol) was transesterified with sodium methoxide (135 mmol) in toluene (150 mL) and NMP (40 mL) and then hydrolyzed with MeOH and H$_2$O (12:1, 165 mL) as before. The resulting acid was dissolved in THF (200 mL) with triethylamine (5 mL), diethylamine (2 mL), and BOP reagent (6.1 g, 13.80 mmol) as above. Work-up and chromatography on silica gel as above afforded 7b (3.02 g, 59%) as a yellow liquid. Conversion to the hydrochloride salt was done with 1 N HCl in ether. $^1$H NMR (CD$_3$OD) δ 1.10–1.25 (m, 12H), 1.76–2.28 (s, 3H), 2.99 (t, 1H, J=12.5 Hz), 3.12–3.29 (m, 1H), 3.31–3.58 (m, 7H), 4.12–4.29 (m, 1H), 6.78 (d, 2H, J=8.8 Hz), 7.18 (d, 2H, J=7.3 Hz), 7.22 (d, 2H, J=8.8 Hz), 7.33 (t, 1H, J=7.4 Hz), 7.48 (t, 2H, J=7.5 Hz); $^{13}$C NMR (CD$_3$OD) δ 16.1, 29.0, 35.3, 43.8, 55.3, 58.7, 60.7, 116.9, 127.3, 127.8, 129.1, 130.7, 131.2, 144.0, 152.0, 173.9. Anal. (C$_{24}$H$_{34}$ClN$_3$O.1.25H$_2$O): C, H, N.

(±)-4-[N-{(3RS,4SR)-N-Allyl-3-methyl-4-piperidinyl}phenylamino]-N,N-diethyl-benzamide (3a).

(±)-4-[N-{(3RS,4SR)-N,3-Dimethyl-4-piperidinyl}phenylamino]-N,N-diethyl-benzamide (7a) (4.1 g, 10.82 mmol) was treated with phenyl chloroformate (1.25 mL, 11.13 mmol) in 1,2-dichloroethane (35 mL) at room temperature for 24 h. The reaction was quenched with water and NaOH 30% then extracted with CHCl$_3$. After drying over Na$_2$SO$_4$ and evaporation of the solvents under reduced pressure, the crude product was chromatographed on silica gel to give a mixture of starting material and product which was then treated with methanol (100 mL), water (60 mL), isopropanol (50 mL), and NaOH 50% (30 mL) at reflux for 5 h. The alcohols were evaporated under reduced pressure, and the aqueous layer was extracted with CHCl$_3$/THF (3:1). After drying with Na$_2$SO$_4$, the solvents were evaporated under reduced pressure. Chromatography on silica gel using hexanes/ethyl acetate/ethanol/triethylamine (50:50:3:3) afforded starting material (6a), (548 mg, 13%), as a yellow oil followed by the N-demethylated material (924 mg, 30%) as a yellow oil using ethanol/triethylamine (80:20) as eluent. The latter material was dissolved in ethanol (40 mL) and treated with allyl bromide (220 μL, 2.54 mmol) and K₂CO₃ (1.0 g, 7.24 mmol) at room temperature for 24 h. After evaporation of the ethanol under reduced pressure, the residue was chromatographed on silica gel using hexanes/ethyl acetate/ethanol/triethylamine (50:50:3:3) to give 3a (950 mg, 93%) as a yellow oil. This was converted to the hydrochloride as previously described: $^1$H NMR ($\delta_4$-MeOH) 1.18 (m, 6H), 1.23 (d, 3H, J=7.4 Hz), 1.54 (d, 1H, J=13.0 Hz), 1.81 (ddd, 1H, J=13.0 Hz, 13.0 Hz, 11.0 Hz), 2.91 (m, 1H), 3.09 (dd, 1H, J=13.0 Hz, 13.0 Hz), 3.44 (m, 7H), 3.75 (d, 1H, 7.4 Hz), 4.38 (d, 1H, J=13.5 Hz), 5.59 (d, 1H, J=9.9 Hz), 5.60 (d, 1H, J=17.0 Hz), 6.00 (ddd, 1H, J=17.0 Hz, 17.0 Hz, 7.4 Hz), 6.79 (d, 2H, J=8.5 Hz), 7.14 (d, 2H J=8.0 Hz), 7.23 (d, 2H, J=8.5 Hz), 7.28 (dd, 1H, J=8.0 Hz, 8.0 Hz), 7.40 (dd, 2H, J=8.0 Hz, 8.0Hz). $^{13}$C NMR (d4-MeOH) 11.3, 13.2 (broad), 24.5, 29.3, 45.0 (broad), 52.4, 55.2, 56.7, 59.6, 118.3, 125.9, 126.4, 126.6, 127.7, 129.7, 145.0, 149.8, 172.7. Anal. ($C_{26}H_{36}ClN_3O.0.25H_2O$): C, H, N.

(±)4-[N-{(3RS,4RS)-N-Allyl-3-methyl-4-piperidinyl}phenylamino]-N,N-diethyl-benzamide (3b).

(±)-4-[N-{(3RS,4RS)-N,3-Dimethyl-4-piperidinyl}phenylamino]-N,N-diethyl-benzamide (7b) (502 mg, 1.32 mmol) was treated with phenyl chloroformate (170 μL, 1.51 mmol) in 1,2-dichloroethane (4 mL) at room temperature for 24 h. The product was worked-up as above, and chromatography on silica gel using hexanes/ethyl acetate/ethanol/triethylamine (75:25:1:1) afforded first the phenylcarbamate as a white solid followed by the starting material (117 mg, 23%) as a yellow liquid. The carbamate was treated with methanol (20 mL), water (15 mL), isopropanol (10 mL), and NaOH 50% (5 mL) and worked-up as above to give the crude N-demthylated intermediate as a yellow oil. This was dissolved in ethanol (5 mL) and treated with allyl bromide (100 μL, 1.15 mmol) and K₂CO₃ (500 mg, 3.62 mmol) for 16 h at room temperature. Work-up and purification as above afforded 3b (70 mg, 15% overall) as a yellow oil. This was converted to the hydrochloride salt as previously described: $^1$H NMR (CD₃OD) δ 1.10–1.26 (m, 9H), 1.741.96 (m, 1H), 1.98–2.29 (m, 2H), 2.88–3.01 (m, 1H), 3.10–3.22 (m, 1H), 3.35–3.61 (m, 7H), 3.73 (d, 2H, J=7.3 Hz), 4.20 (dt, 1H, J=3.4 Hz, J=11.5 Hz), 5.55 (s, 1H), 5.61 (d, 1H, J=5.4 Hz), 5.85–6.03 (m, 1H), 6.78 (d, 2H, J=8.8 Hz), 7.19 (d, 2H, J=7.8 Hz), 7.23 (d, 2H, J=8.8 Hz), 7.34 (t, 1H, J=7.4 Hz), 7.51 (t, 2H, J=7.6 Hz); $^{13}$C NMR (CD₃OD) δ 11.9, 13.9, 16.2, 28.9, 35.2, 52.9, 58.3, 59.1, 60.1, 117.0, 126.8, 127.6, 127.8, 129.0, 130.7, 131.2, 144.1, 151.8, 173.9. Anal. ($C_{26}H_{36}ClN_3O.0.25H_2O$): C, H, N.

Example 7

N-alkyl-4β-methyl-5-phenylmorphans

Summary

A convergent, highly stereoselective synthetic approach to N-alkyl-4p-methyl-5-phenylmorphans has been developed utilizing alkylation of the metalloenamine of N-alkyl-1,2,3,6-tetrahydro-4-phenylpyridines with 2-(chloromethyl)-3,5-dioxahex-1-ene (Okahara's reagent) followed by Clemmensen reduction.

Chemistry

Figure 18:
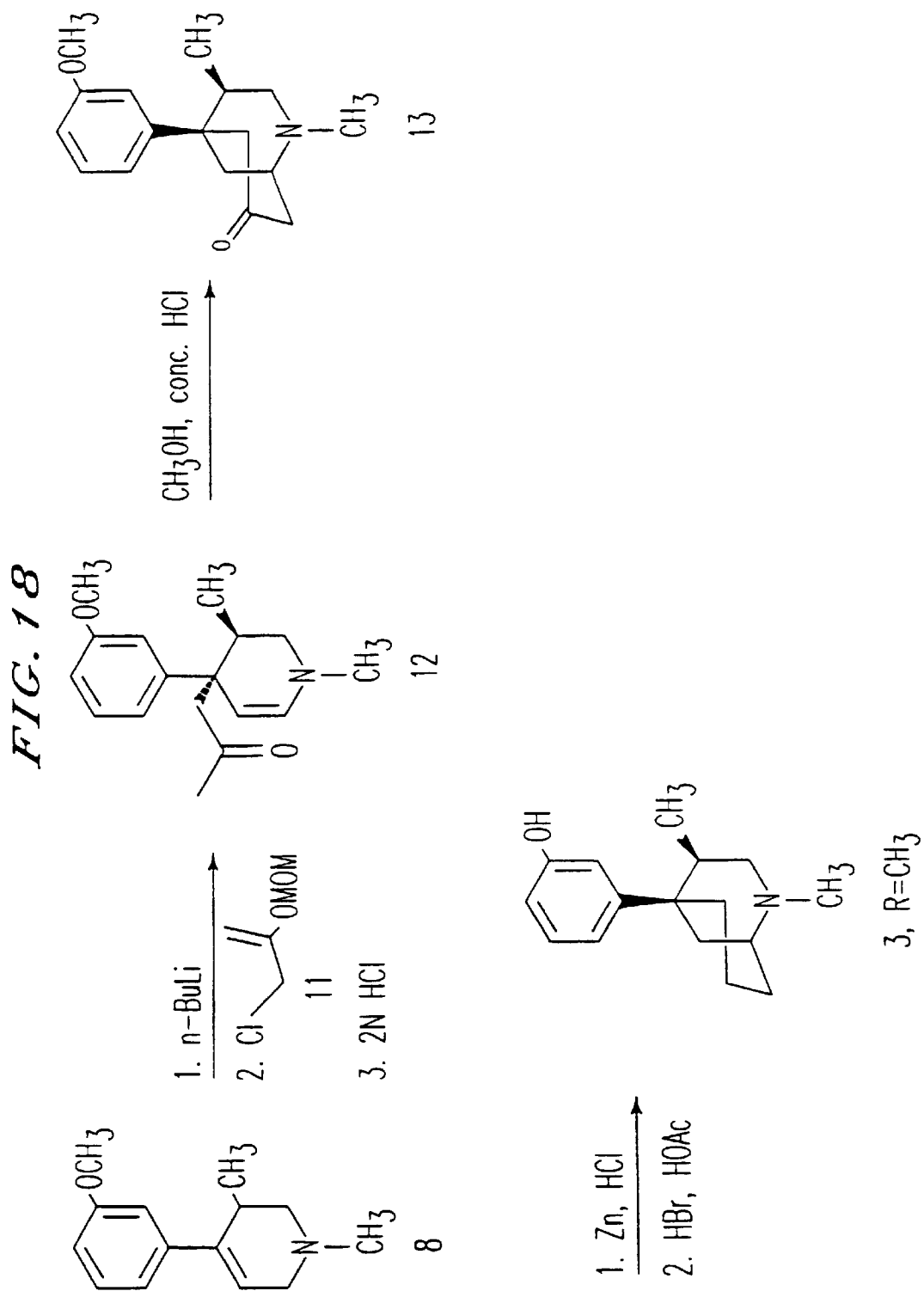
FIG. 18: Synthesis of 4β-5-phenylmorphans as described in Example 7.

4β-methyl-(3-hydroxyphenyl)morphans were stereoselectively synthesized as shown in FIG. 18. Alkylation of 8[1] with 2-(chloromethyl)-3,5-dioxohex-1-ene (Okahara's reagent)[2] followed by hydrolysis of the methoxymethyl protecting group (FIG. 18) gives enamine 12. In the alkylation reaction, the methyl group apparently exerts a powerful directing effect since enamine 12 is the sole product. Cyclization under acidic conditions occurs regiospecifically on carbon 1 (phenylmorphan numbering) due to the specific migration of the double bond during the alkylation reaction. Furthermore, since the oxidation state of carbon 7 does not change following cyclization, no hydride shift occurs and the stereogenic center of carbon 4 is preserved providing 2,4β-dimethyl-7-oxo-5-(3-methoxyphenyl)morphan (13) as a single diastereomer. Clemmensen reduction[3] and deprotection of the phenol[4] then completes the synthesis of 2,4β-dimethyl-5-(3-hydroxyphenyl)morphan (3, R=CH₃) in 48% overall yield from 8. The stereochemical assignments for 3 (R=CH₃) were made using NOESY spectra of a sealed degassed sample obtained with mixing time of 1.500 sec and an interpulse delay of 4 sec.[5] A strong interaction between the 4-methyl group and the 9β and 3β protons established the 4β-stereochemistry.

A requirement for significant quantities of 3 and its analogs for in vivo testing coupled with the usefulness of intermediates similar to 13 in the preparation of delta opioid receptor selective agonists,[6,7] suggested improving the overall yield of the alkylation/ cyclization sequence. Experimentation with a variety of conditions revealed that addition of the metalloenamine of 8 to a solution of Okahara's reagent, rather than the reverse, gave much higher yields in the metalloenamine alkylation. In combination with an extractive workup to remove formaldehyde (formed by hydrolysis of the methoxymethyl group) and cyclization conditions similar to those defined by Bonjoch et al.,[8] the overall yield of the alkylation/cyclization sequence for 13 was significantly improved (75% for this work vs. 30% using the one-pot procedure).[9]

In summary, this example provides a highly diastereoselective synthetic approach to the N-alkyl-4δ-methyl-5-(3-hydroxyphenyl)morphan system as well as providing a higher yielding route to the useful 7-oxo-5-(3-methoxyphenyl)morphan opioid intermediates.

REFERENCES AND NOTES

1. Werner, J. A.; Cerbone, L. R.; Frank, S. A.; Ward, J. A.; Labib, P.; Tharp-Taylor, R. W.; Ryan, C. W. *J. Org. Chem.* 1996, 61, 587–597.
2. Gu, X.-P.; Nishida, N.; Ikeda, I.; Okahara, M. *J. Org. Chem.* 1987, 52, 3192–3196.
3. Bosch, J.; Bonjoch, J. *Heterocycles* 1980, 14, 505.
4. Rice, K. C. *J. Med. Chem.* 1977, 20, 164–165.
5. Proton assignments for 3 were made using a combination of COSY and HETCORR spectra. $^1$H NMR (d4-MeOH) δ 0.782 (d, 3H, J=7.5 Hz), 1.65 (m, 1H), 1.78 (m, 1H), 1.85 (m, 1H), 2.02 (d, 1H, J=15 Hz), 2.08 (m, 1H), 2.24 (m, 1H), 2.29 ( m, 1H), 2.46 (q, 1H, J=7.5 Hz), 2.54 (d, 1H, J=15.0 Hz), 2.92 (s, 3H), 3.26 (d, 1H, J=13.6 Hz), 3.70 (m, 1H), 3.86 (dd, 1H, J=13.6 Hz, 5.3 Hz), 6.67 (m, 1H), 7.15 (t, 3H, J=7.9 Hz).
6. Bertha, C. M.; Flippen-Anderson, J. L.; Rothman, R. B.; Porreca, F.; Davis, P.; Xu, H.; Becketts, K.; Cha, X.-Y.; Rice, K. C. *J. Med. Chem.* 1995, 38, 1523–1537.
7. Bertha, C. M.; Ellis, M.; Flippen-Anderson, J. L.; Porreca, F.; Rothman, R. B.; Davis, P.; Xu, H.; Becketts, K.; Rice, K. C. *J. Med. Chem.* 1996, 39, 2081–2086.
8. Bonjoch, J.; Casamitjana, N.; Gracia, J.; Bosch, J. *Tetrahedron Lett.* 1989, 30, 5655–5658.
9. General Procedure for Alkylation/Cyclization Sequence: (CAUTION: Read reference 4 and references cited therein for information on N-methyl-4-phenyl-1,2,3,6-tetrahydropyridine, MPTP and its derivatives.) The appropriate tetrahydropyridine derivative (1 eq) is dissolved in THF (20 mL/g) and cooled to −10° C. n-Butyl lithium (1.6M in hexanes) is slowly added until a red color is maintained followed by an addition of 1.1 eq. This material is stirred for 1 h at −10° C. and then cannulated quickly into a solution of Okahara's reagent (distilled to high purity) in THF (15 mL/g, 1.1 eq) at −78° C. followed by stirring for 2 h. The temperature should be kept below −30° C. during cannulation. This material is then poured into 2N HCl and extracted twice with ethyl ether. The aqueous layer is allowed to stand for 15 min followed by addition of 50% NaOH to pH 14 and extraction (3×) with ethyl ether. The ether is then washed (1N NaOH, $H_2O$) and the solvent removed under vacuum. The resulting residue of product and water is dissolved in MeOH (30 mL/g) and nitrogen is bubbled through the solution for 5 min. To this is added concentrated HCl (2 mL/g), and the mixture is allowed to stand at room temperature until the reaction is complete as indicated by TLC (up to 7 days). TLC condition: $SiO_2$; elution with 50% (80% $CHCl_3$:18% $CH_3OH$:2% $NH_4OH$) in $CHCl_3$. Detection: 5% phosphomolybdic acid in ethanol. All compounds gave satisfactory $^1H$ and $^{13}C$ NMR and mass spectra.

This Example is described in Thomas et al, *Tetrahedron Letters*, Vol. 40, pp. 403–406 (1999), incorporated herein by reference.

Obviously, numerous modifications and variations of the present invention are possible in light of the above teachings. It is therefore to be understood that within the scope of the appended claims, the invention may be practiced otherwise than as specifically described herein.

All references cited above are incorporated into this application by reference in their entirety unless noted otherwise.

What is claimed as new and is desired to be secured by Letters Patent of the United States is:

1. A compound represented by formula (I):

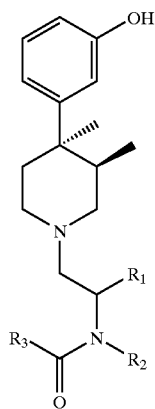

(I)

wherein $R_1$ is hydrogen, an alkyl group, an aryl group, or an aralkyl group;

$R_2$ is hydrogen, an alkyl group, an aryl group, or an alkaryl group; and $R_3$ is

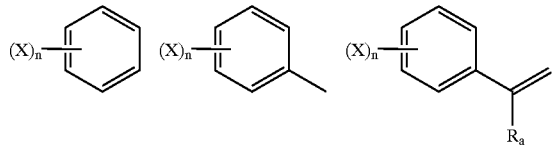

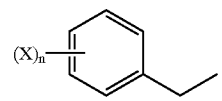

each X is, independently, halogen, —OH, —OR, an alkyl group, an aryl group, —$NH_2$, —NHR, —$N(R)_2$, —$CF_3$, —CN or —$C(O)NH_2$, —C(O)NHR, or —$C(O)N(R)_2$;

each R is, independently, an alkyl group, an aryl group or an alkaryl group, wherein when X is —$N(R)_2$ the R groups may, together, form a cyclic alkyl group;

n is 0 or an integer from 1 to 5; and $R_a$ is hydrogen or an alkyl group, or a pharmaceutically acceptable salt thereof.

2. The compound of claim 1, wherein $R_1$ is hydrogen, a $C_{1-4}$ alkyl group, a phenyl group, or an aralkyl group;

$R_2$ is hydrogen or a $C_{1-4}$ alkyl group; and n is 0, 1, 2, 3 or 4.

3. The compound of claim 2, wherein $R_1$ is hydrogen or a $C_{1-4}$ alkyl group; and n is 0, 1, 2, 3 or 4.

4. The compound of claim 3, wherein $R_1$ is hydrogen or a $C_{1-3}$ alkyl group;

$R_2$ is hydrogen or a methyl group;

n is 1, 2, or 3, and at least one X is —OH, —$OCH_3$ or —F.

5. The compound of claim 4, wherein at least one X is —OH.

6. A method of binding opioid receptors, comprising administering an effective amount of the compound of claim 1 to a mammalian subject in need thereof.

* * * * *

UNITED STATES PATENT AND TRADEMARK OFFICE
CERTIFICATE OF CORRECTION

PATENT NO.    : 6,593,348 B2
DATED         : July 15, 2003
INVENTOR(S)   : Frank I. Carroll et al.

It is certified that error appears in the above-identified patent and that said Letters Patent is hereby corrected as shown below:

<u>Title page</u>
Item [54], "OPIATE COMPOUNDS, METHODS OF MAKING METHODS OF USE" should read -- NOVEL OPIATE COMPOUNDS, METHODS OF MAKING AND METHOD OF USE --.

<u>Column 5,</u>
Lines 54-56, "g, $R_1=CH_3$, $R_2$ and $R_3=H$, $R_4=CH_3$" should read
-- f, $R_1=CH_2C_3H_5$, $R_2=H$, $R_4=H$
   h, $R_1=CH_3$, $R_2$ and $R_3=H$, $R_4=CH_3$ --.

<u>Column 6,</u>
Line 28, 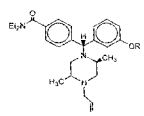

should read -- 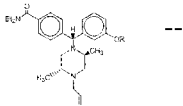 --

<u>Column 11,</u>
Line 11, "z is 0 an integer" should read -- z is 0 or an integer --.

<u>Column 16,</u>
Line 45, "antiartiritic agents" should read -- antiarthritic agents --.

<u>Column 24,</u>
Line 22, "-4(3-" should read -- -4-(3- --;
Line 54, "phenylglycine" should read -- phenylglycine[17] --.

<u>Column 25,</u>
Line 67, "1.28 (s, 3H)" should read -- 1.28 (s, 3H), --.

<u>Column 26,</u>
Line 20, "3.30 (m, 1H)" should read -- 3.30 (m, 2H) --;
Line 57, "bydroxyphenyl)" should read -- hydroxyphenyl) --

<u>Column 27,</u>
Line 29, "J=12.3 (s, 3H)," should read -- J-12.3 Hz), 1.23 (s, 3H), --.
Line 60, "2.29. (" should read -- 2.29 ( --.

UNITED STATES PATENT AND TRADEMARK OFFICE
CERTIFICATE OF CORRECTION

PATENT NO. : 6,593,348 B2
DATED : July 15, 2003
INVENTOR(S) : Frank I. Carroll et al.

It is certified that error appears in the above-identified patent and that said Letters Patent is hereby corrected as shown below:

Column 32,
Line 42, "αi-pr" should read -- αi-Pr --.

Column 34,
Line 48, "Benzoylbenoic Acid" should read -- Benzoylbenzoic Acid --.
Line 59, "Flurobenzoic Acid" should read -- Fluorobenzoic --.

Column 35,
Line 40, "Acd" should read -- Acid --.

Column 36,
Line 11, "dinotro" should read -- dinitro --.

Column 39,
Line 66, "-3R, 4R)" should read -- -(3R, 4R) --.

Column 40,
Line 66, "Odemethylation" should read -- O-demethylation --.

Column 42,
Line 12, "4,4a,5,    10" should read -- 4,4a,5,10 --;
Line 61, "diochloroxylene" should read -- dichloroxylene --;
Line 66, "to filtered into" should read -- filtered into --.

Column 45,
Line 21, "RTI4614-4" should read -- RTI-4614-4 --;
Line 51, "cyclohexyl)" should read -- cyclohexyl] --.

Column 46,
Line 33, "hydoxyphenyl)" should read -- hydroxyphenyl) --.

Column 47,
Line 57, "(m-methoxypenyl)" should read -- (m-methoxyphenyl) --.

Column 48,
Line 28, "443.0," should read -- 43.0, --.

UNITED STATES PATENT AND TRADEMARK OFFICE
CERTIFICATE OF CORRECTION

PATENT NO.   : 6,593,348 B2
DATED        : July 15, 2003
INVENTOR(S)  : Frank I. Carroll et al.

It is certified that error appears in the above-identified patent and that said Letters Patent is hereby corrected as shown below:

Column 49,
Line 13, "colorless is oil" should read -- colorless oil --;
Line 24, "for r 1 h" should read -- for 1 h --.

Column 50,
Line 32, "(m, 4h." should read -- (m, 4h). --;
Line 39, "dimethyl4a" should read -- dimethyl-4a --.

Column 51,
Line 51, "dimethyl4" should read -- dimethyl-4 --.

Column 52,
Line 37, "10 FM" should read -- $10\,\mu M$ --;
Line 41, "dimethyl4" should read -- dimethyl-4 --.

Column 53,
Lines 5, 12, 25 and 30, "dimethy14-'" should read -- dimethyl-4- --;
Line 23, "9, β-" should read -- 9β- --.

Column 54,
Line 11, "(100%)" should read -- (~ 100%) --.

Column 55,
Line 5, "C1$_6$" should read -- C$_{16}$ --.

Column 56,
Line 24, "1 mg/nL" should read -- 1 mg/mL --;
Lines 55-56, ", pH 7.4). [$^3$H]" should read as two separate paragraphs as follows
-- , pH 7.4).
[$^3$ H] --.

Column 57,
Line 52, "[$^{35}$]" should read -- [$^{35}$S] --;
Line 67, "SHELXS" should read -- SHELXL.[11] --.

Column 58,
Line 1, "SHELXS" should read -- SHELXL.[11] --;
Line 6, "A" should read -- Å --;
Lines 54 and 59, "Rothrman" should read -- Rothman --.

UNITED STATES PATENT AND TRADEMARK OFFICE
CERTIFICATE OF CORRECTION

PATENT NO. : 6,593,348 B2
DATED : July 15, 2003
INVENTOR(S) : Frank I. Carroll et al.

It is certified that error appears in the above-identified patent and that said Letters Patent is hereby corrected as shown below:

Column 62,
Line 62, "9βstereochemical" should read -- 9β stereochemical --.

Column 64,
Line 2, "(60%)" should read -- (~60%) --;
Line 29, "40° C" should read -- -40°C --;
Line 41, "(70%)" should read -- (~ 70%) --;
Line 64, "C, 5 74.78" should read -- C, 74.78 --.

Column 65,
Lines 4 and 17, "1-Benzyl4-" should read -- 1-Benzyl-4- --;
Line 24, "5 (ppm)" should read -- δ(ppm) --;
Line 48, "$C_{19}H_2$," should read -- $C_{19}H_{21}$ --.

Column 66,
Line 40, "dimethyl4-" should read -- dimethyl-4- -- .

Column 67,
Line 56, "isevenfold" should read -- sevenfold --;
Line 64, "us" should read -- in --.

Column 68,
Line 23, "π" should read -- κ --.

Column 69,
Lines 19, 44 and 50 "butyl4-" should read -- butyl-4- --;
Lines 20 and 61, "dimethyl4-" should read -- dimethyl-4- --;
Line 24, "42°C" should read -- -42°C --;
Line 58, "(±)4-" should read -- (±)-4- --;
Line 60, "butyl4-methoxyphenyl4" should read -- butyl-4-methoxyphenyl-4 --;

Column 70,
Line 5, "5:200 mL" should read -- 5′ 200 mL --;
Line 25, "Dimethyl4-" should read -- Dimethyl-4- --;
Line 27, "butyl4-methoxyphenyl4" should read -- butyl-4-methoxyphenyl-4 --;
Line 28, "dimethy14-" should read -- dimethyl-4- --;
Line 28, "phenylarino]" should read -- phenylamino] --.

UNITED STATES PATENT AND TRADEMARK OFFICE
CERTIFICATE OF CORRECTION

PATENT NO. : 6,593,348 B2
DATED : July 15, 2003
INVENTOR(S) : Frank I. Carroll et al.

It is certified that error appears in the above-identified patent and that said Letters Patent is hereby corrected as shown below:

Column 71,
Line 14, "2H J=8.0 Hz" should read -- 2H, J=8.0 Hz --;
Line 34, "demthylated" should read -- demethylated --;
Line 56, "-4p-" should read -- -4β- --.

Column 72,
Line 33, "-4δ-" should read -- -4β- --.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,593,348 B2
DATED : July 15, 2003
INVENTOR(S) : Frank I. Carroll et al.

It is certified that error appears in the above-identified patent and that said Letters Patent is hereby corrected as shown below:

<u>Column 64,</u>
Line 29, "-42ºC" should read -- -42ºC --.

Signed and Sealed this

Fifth Day of October, 2004

JON W. DUDAS
*Director of the United States Patent and Trademark Office*